US012685537B2

(12) United States Patent
Shi et al.

(10) Patent No.: US 12,685,537 B2
(45) Date of Patent: Jul. 21, 2026

(54) END EFFECTOR INSTRUMENT

(71) Applicant: HANGZHOU AGS MEDTECH CO., LTD., Hangzhou (CN)

(72) Inventors: Baiming Shi, Hangzhou (CN); Jing Xi, Hangzhou (CN)

(73) Assignee: HANGZHOU AGS MEDTECH CO., LTD., Hangzhou (CN)

( * ) Notice: Subject to any disclaimer, the term of this patent is extended or adjusted under 35 U.S.C. 154(b) by 748 days.

(21) Appl. No.: 17/755,973

(22) PCT Filed: Nov. 12, 2020

(86) PCT No.: PCT/CN2020/128479
§ 371 (c)(1),
(2) Date: May 13, 2022

(87) PCT Pub. No.: WO2021/093824
PCT Pub. Date: May 20, 2021

(65) Prior Publication Data
US 2022/0387041 A1 Dec. 8, 2022

(30) Foreign Application Priority Data

| Nov. 13, 2019 | (CN) | 201911107241.5 |
| Apr. 24, 2020 | (CN) | 202010330106.3 |
| Jul. 23, 2020 | (CN) | 202010716427.7 |

(51) Int. Cl.
*A61B 17/128* (2006.01)
*A61B 17/122* (2006.01)
A61B 17/00 (2006.01)

(52) U.S. Cl.
CPC ...... *A61B 17/1285* (2013.01); *A61B 17/1222* (2013.01); *A61B 17/1227* (2013.01); *A61B 2017/00477* (2013.01)

(58) Field of Classification Search
CPC ................ A61B 17/0057; A61B 17/122–1285
See application file for complete search history.

(56) References Cited

U.S. PATENT DOCUMENTS

| 4,791,707 A | 12/1988 | Tucker |
| 6,814,742 B2 | 11/2004 | Kimura et al. |

(Continued)

FOREIGN PATENT DOCUMENTS

| CN | 102204838 A | 10/2011 |
| CN | 202477780 U | 10/2012 |

(Continued)

OTHER PUBLICATIONS

The Extended European Search Report in European Application No. 20888473.4 mailed on Oct. 31, 2022, 8 pages.

(Continued)

*Primary Examiner* — Elizabeth Houston
*Assistant Examiner* — Jonathan A Hollm
(74) *Attorney, Agent, or Firm* — Metis IP LLC

(57) ABSTRACT

Some embodiments of the present disclosure may provide an end effector instrument. The end effector instrument may include: an end effector device, the end effector device comprising an effector portion configured to perform a specified operation, and a delivery device connected to the end effector device, the delivery device being configured to deliver the end effector device to a target region where the specified operation is to be performed. The delivery device may include an operation portion. The operation portion may be configured to drive the effector portion to perform the specified operation.

19 Claims, 52 Drawing Sheets

(56) References Cited

U.S. PATENT DOCUMENTS

| | | | |
|---|---|---|---|
| 10,856,883 B2 * | 12/2020 | Maekubo | A61B 1/00 |
| 2005/0143767 A1 | 6/2005 | Kimura et al. | |
| 2007/0112359 A1 * | 5/2007 | Kimura | A61B 17/1222 |
| | | | 606/142 |
| 2008/0140089 A1 * | 6/2008 | Kogiso | A61B 17/1285 |
| | | | 606/142 |
| 2010/0217292 A1 | 8/2010 | Kimura et al. | |
| 2011/0245855 A1 * | 10/2011 | Matsuoka | A61B 17/122 |
| | | | 606/157 |
| 2012/0065646 A1 | 3/2012 | Phillips-Hungerford et al. | |
| 2014/0088616 A1 | 3/2014 | Clerc et al. | |
| 2017/0020531 A1 * | 1/2017 | Naveed | A61B 17/1285 |
| 2017/0086824 A1 | 3/2017 | Khan | |
| 2017/0296197 A1 | 10/2017 | Tsueda et al. | |
| 2019/0133598 A1 | 5/2019 | Uesaka et al. | |
| 2019/0223875 A1 * | 7/2019 | Saenz Villalobos | A61B 17/122 |
| 2020/0060685 A1 | 2/2020 | Han et al. | |

FOREIGN PATENT DOCUMENTS

| | | |
|---|---|---|
| CN | 103315792 A | 9/2013 |
| CN | 108784773 A | 11/2018 |
| JP | 2015043858 A | 3/2015 |

OTHER PUBLICATIONS

International Search Report in PCT/CN2020/128479 mailed on Feb. 18, 2021, 11 pages.
Written Opinion in PCT/CN2020/128479 mailed on Feb. 18, 2021, 10 pages.

* cited by examiner

Opening of an assembly groove

Narrow section

702

721

Wide section

Bottom of
an assembly groove

701

763B

763A

1000

1100

END EFFECTOR INSTRUMENT

CROSS-REFERENCE TO RELATED APPLICATIONS

This application is a U.S. national stage under 35 U.S.C. § 371 of International Application No. PCT/CN2020/128479, filed on Nov. 12, 2020, which claims priority to Chinese Patent Application No. 201911107241.5, filed on Nov. 13, 2019, Chinese Patent Application No. 202010330106.3, filed on Apr. 24, 2020, and Chinese Patent Application No. 202010716427.7, filed on Jul. 23, 2020, the contents of each of which are hereby incorporated by reference.

TECHNICAL FIELD

The present disclosure relates to medical instruments, and more particularly, relates to an end effector instrument.

BACKGROUND

At present, in minimally invasive surgery, an end effector device such as a hemostatic clip, ligation clip, etc., is often used under endoscopy. The end effector device may clamp human tissue to achieve the function of surgical hemostasis or ligation. In order to deliver the end effector device to human tissue for operation, it is usually necessary to assemble the end effector device with a delivery device to form an end effector instrument. However, the commonly used end effector device has a complicated structure after being closed, and the production cost is high. Moreover, an assembly of the end effector device and the delivery device usually needs to be done manually, which is inefficient.

Therefore, it is necessary to provide an end effector instrument with a simple structure and easy assembly to reduce manual operations and improve the efficiency and accuracy of the assembly of a delivery device and an end effector device.

SUMMARY

Some embodiments of the present disclosure may provide an end effector instrument. The end effector instrument may include: an end effector device, the end effector device comprising an effector portion configured to perform a specified operation; and a delivery device connected to the end effector device, the delivery device being configured to deliver the end effector device to a target region where the specified operation is to be performed. The delivery device may include an operation portion. The operation portion may be configured to drive the effector portion to perform the specified operation.

In some embodiments, the end effector device may further include an accommodation portion. The accommodation portion may be configured to partially accommodate the effector portion. The delivery device may include a delivery pipe. The accommodation portion may be releasably connected to the delivery pipe.

In some embodiments, the accommodation portion may include a first connecting portion. The delivery pipe may include a second connecting portion. The second connecting portion may be configured to connect the first connecting portion to establish a connection between the delivery device and the end effector device.

In some embodiments, the accommodation portion may include an inner pipe and an outer pipe. At least a portion of the outer pipe may fit snugly over the inner pipe. The first connecting portion may be located on the inner pipe.

In some embodiments, the first connecting portion may include a limiting convex. The second connecting portion may include a limiting concave. The end effector device and the delivery device may be configured such that: when the limiting convex extends into the limiting concave, the end effector device is connected to the delivery device; and when the limiting convex retracts from the limiting concave, the end effector device is disconnected from the delivery device.

In some embodiments, the limiting convex and the accommodation portion may be integrally formed.

In some embodiments, the operation portion may include a shaft positioned within the delivery pipe. An end of the shaft may enter into or retract from the accommodation portion. When the end of the shaft enters into the accommodation portion, the limiting convex may be compressed by a connecting end to enter into the limiting concave. When the end of the shaft retracts from the accommodation portion, the limiting convex may retract from the limiting concave.

In some embodiments, one end of the shaft may include a connecting end. An outer diameter of the connecting end may exceed an inner diameter of the limiting convex.

In some embodiments, the effector portion may include a lock connecting portion. The accommodation portion may include a locking portion. The locking portion may be configured to connect the lock connecting portion. When the locking portion connects the lock connecting portion, the effector portion and the accommodation portion may be fixed relative to each other.

In some embodiments, the accommodation portion may include a guiding groove located along an axial direction. The lock connecting portion may be configured to slide within the guiding groove.

In some embodiments, the accommodation portion may include an inner pipe and an outer pipe. The locking portion may be located on the outer pipe. The guiding groove may be configured on the inner pipe.

In some embodiments, the locking portion may include an elastic piece. One end of the elastic piece may be fixedly connected to the accommodation portion, and another end of the elastic piece may extend into an interior of the accommodation portion. Alternatively, the locking portion may include an elastic piece. One end of the elastic piece may be fixedly connected to the outer pipe, and another end of the elastic piece may extend into an interior of the inner pipe.

In some embodiments, an end of the guiding groove away from the effector portion may have a positioning convex. A distance between the positioning convex and the effector portion may exceed a distance between the locking portion and the effector portion.

In some embodiments, a retaining portion may be located on the positioning convex. The retaining portion may include a fixed end and a free end. The fixed end of the retaining portion may be fixedly connected to the positioning convex. The free end of the retaining portion may face an interior of the guiding groove.

In some embodiments, the effector portion includes a clip. The clip may include a first clip arm, a second clip arm, and a connecting pin. The first clip arm and the second clip arm may be connected through the connecting pin. The lock connecting portion may be formed by one end or both ends of the connecting pin.

In some embodiments, the clip may also include an elastic ring. The elastic ring may fit snugly over the connecting pin. The elastic ring may be located between the first clip arm and the second clip arm.

In some embodiments, an end of the first clip arm close to the connecting pin may have a first bending portion that bends towards the second clip arm. The first bending portion may have a first hole. One end of the second clip arm close to the connecting pin may have a second bending portion that bends towards the first clip arm. the second bending portion may have a second hole. The first hole and the second hole may at least partially overlap.

In some embodiments, the shaft may include a large-diameter portion and a small-diameter portion. The small-diameter portion of the shaft may be fixedly connected to the connecting end. The large-diameter portion of the shaft may be fixedly connected to the small-diameter portion of the shaft. A diameter of the large-diameter portion of the shaft may exceed a diameter of the small-diameter portion of the shaft.

In some embodiments, a first hole and a second hole may at least partially overlap and communicate to form a connecting hole. The diameter of the large-diameter portion of the shaft may exceed a diameter of an inner diameter of the connecting hole. The diameter of the small-diameter portion of the shaft may be smaller than the inner diameter of the connecting hole.

In some embodiments, the end effector instrument may further include: an assembly device configured to assemble the end effector device and the delivery device to establish a connection between the end effector device and the delivery device.

In some embodiments, the assembly device may include an assembly box configured to fix the end effector device and the delivery device when the end effector device and the delivery device are assembled.

In some embodiments, the assembly box may include: an accommodation portion configured to accommodate the end effector device; an assembly groove configured to accommodate the delivery device to achieve an assembly of the delivery device and the end effector device; and a joint portion configured to fix the delivery device in the assembly groove.

In some embodiments, the joint portion may include a first portion and a second portion. The first portion of the joint portion may extend beyond an outer surface of the assembly groove. After the first portion of the joint portion is pressed, the second portion of the joint portion may enter into an interior of the assembly groove.

In some embodiments, the assembly device may further include an assembly tool. The assembly tool may include at least one groove. The assembly box may be configured to enter into or retract from the at least one groove.

In some embodiments, one of the at least one groove of the assembly tool may include a first channel. A height of the first channel may be smaller than or equal to a height of the joint portion. When the joint portion enters into the first channel, the first channel may press the first portion of the joint portion.

In some embodiments, the groove may further include a second channel. the second channel may be in communication with the first channel. The second channel may be located at an entrance end of the first channel. A height of the second channel may gradually decrease along a direction from the entrance end to the first channel.

In some embodiments, the groove may further include a third channel. The third channel is in communication with the first channel. The third channel may be located at an exit end of the first channel. A height of the third channel may exceed a height of the first channel.

In some embodiments, a convex portion may be located outside the assembly box, the convex portion being elastic. The convex portion may be in a compressed state when the convex portion is positioned within the first channel. The convex portion may be in an original state when the convex portion is positioned within the third channel.

In some embodiments, the third channel may be configured with an elastic component. The elastic component may be configured to apply a bias pressure to the assembly box along a first direction so as to cause the assembly box to retract from the third channel.

In some embodiments, the end effector device may include an expanding window. The assembly box may include an operating window and an expanding portion; the operating window may be in communication with the expanding window. The expanding portion may be configured to extend into an interior of the effector device through the operation window and the expanding window to facilitate establishing a connection between the end effector device and the delivery device.

In some embodiments, the assembly groove may include a groove slot and a limiting slot. The groove slot may be located at a side of the assembly groove. The limiting slot may be in communication with the groove slot. A width of the limiting slot may be smaller than a width of the assembly groove.

In some embodiments, the assembly box may include a limiting portion. The limiting portion may be configured to limit a relative movement between the delivery device and the assembly box.

In some embodiments, the assembly box may include a housing. The limiting portion of the assembly box may be located on the housing. The delivery device may include a delivery pipe. The limiting portion of the assembly box may be configured to limit a relative movement between the delivery pipe and the housing.

In some embodiments, the limiting portion of the assembly box may include at least one of a groove body, a limiting channel, or a buckle.

In some embodiments, the limiting portion of the assembly box may be configured with at least one convex point.

Some embodiments of the present disclosure may also provide an assembly and operation method of an end effector instrument in any embodiments of the present disclosure. The assembly and operation method may include: controlling the assembly box to enter into the at least one groove of the assembly tool; controlling the delivery pipe of the delivery device to enter into the assembly groove to achieve a first assembly with the accommodation portion of the end effector device; controlling the assembly box and the delivery pipe to continue to move towards an interior of the at least one groove of the assembly tool to axially fix the delivery pipe in the assembly groove; controlling a shaft of the delivery device to move towards the end effector device to achieve a second assembly with the clip of the effector portion; and retracting the assembled end effector device and the delivery device from the assembly box.

In some embodiments, the controlling the assembly box to enter into the at least one groove of the assembly tool may include: controlling the convex portion of the assembly box to enter into the first channel through the second channel; controlling the convex portion of the assembly box to enter into the third channel through the first channel and to obtain first feedback information; and in response to the first feedback information, stopping moving the assembly box.

In some embodiments, the third channel may include the elastic component. The controlling the assembly box to enter into the at least one groove of the assembly tool may include: controlling the convex portion of the assembly box to enter into the first channel from the second channel; controlling the convex portion to enter into the third channel from the first channel and to obtain third feedback information; and in response to the third feedback information, stopping moving the assembly box.

In some embodiments, the controlling the assembly box and the delivery pipe to continue to move towards the interior of the at least one groove of the assembly tool to axially fix the delivery pipe in the assembly groove may include: controlling the joint portion of the assembly box to enter into the first channel; controlling the first channel to press the first portion of the joint portion, such that the second portion of the joint portion enters into the assembly groove; and controlling the second portion of the joint portion to press the delivery pipe, such that the delivery pipe is axially fixed in the assembly groove.

In some embodiments, the controlling the shaft of the delivery device to move towards the end effector device to achieve the second assembly with the clip of the effector portion may include: controlling a connecting end of the shaft to enter into the accommodation portion, such that the limiting convex of the accommodation portion extends into the limiting concave of the delivery pipe to establish a connection between the accommodation portion and the delivery pipe; and controlling a large-diameter portion of the shaft to extend into a connecting hole of the clip of the effector portion to establish a connection between the shaft and the clip.

In some embodiments, the retracting the assembled end effector device and the delivery device from the assembly box may include: driving the assembly box to move from the interior of the at least one groove of the assembly tool to an exterior of the at least one groove, and obtaining second feedback information; and retracting the end effector device and the delivery device from the assembly groove based on the second feedback information.

In some embodiments, the retracting the assembled end effector device and the delivery device from the assembly box may include: driving the assembly box to move from the interior of the at least one groove to an exterior of the at least one groove, and obtaining fourth feedback information; and retracting the end effector device and the delivery device from the assembly groove based on the fourth feedback information.

BRIEF DESCRIPTION OF THE DRAWINGS

The present disclosure is further described in terms of exemplary embodiments. These exemplary embodiments are described in detail with reference to the drawings. These embodiments are non-limiting, in which like reference numerals represent similar structures throughout the several views of the drawings, and wherein.

6

Figure 3:
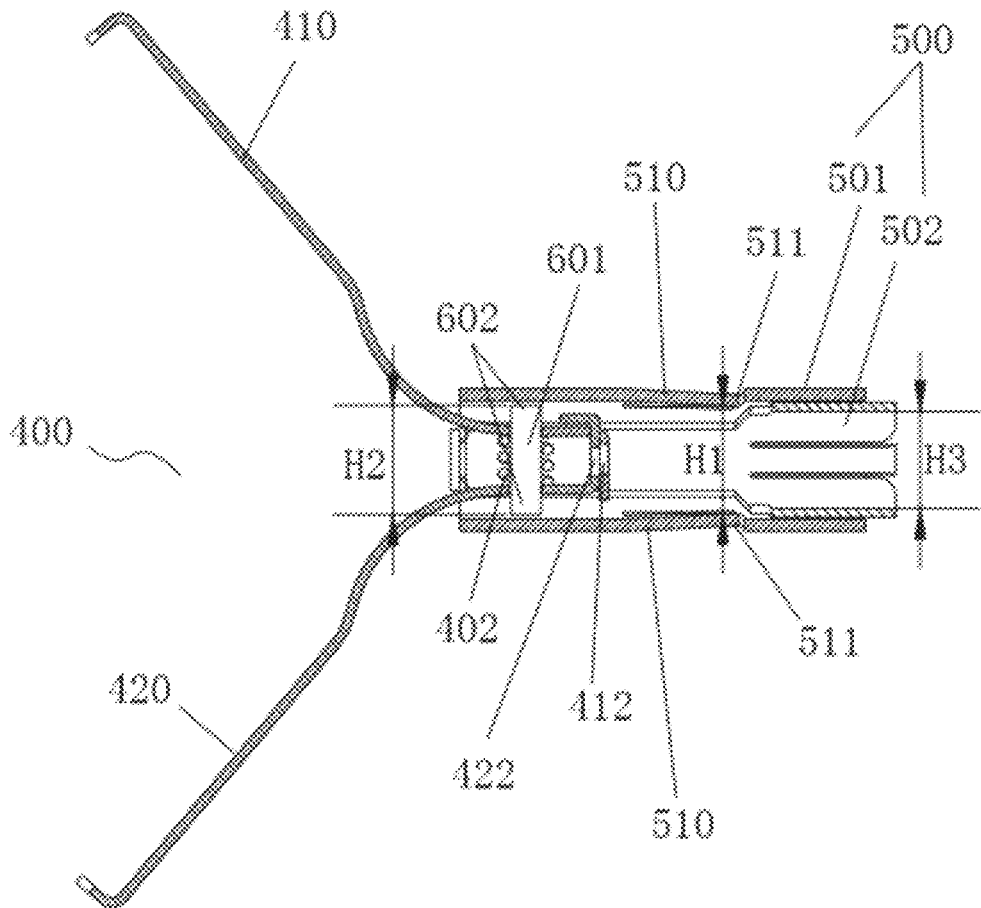
Figure 4:
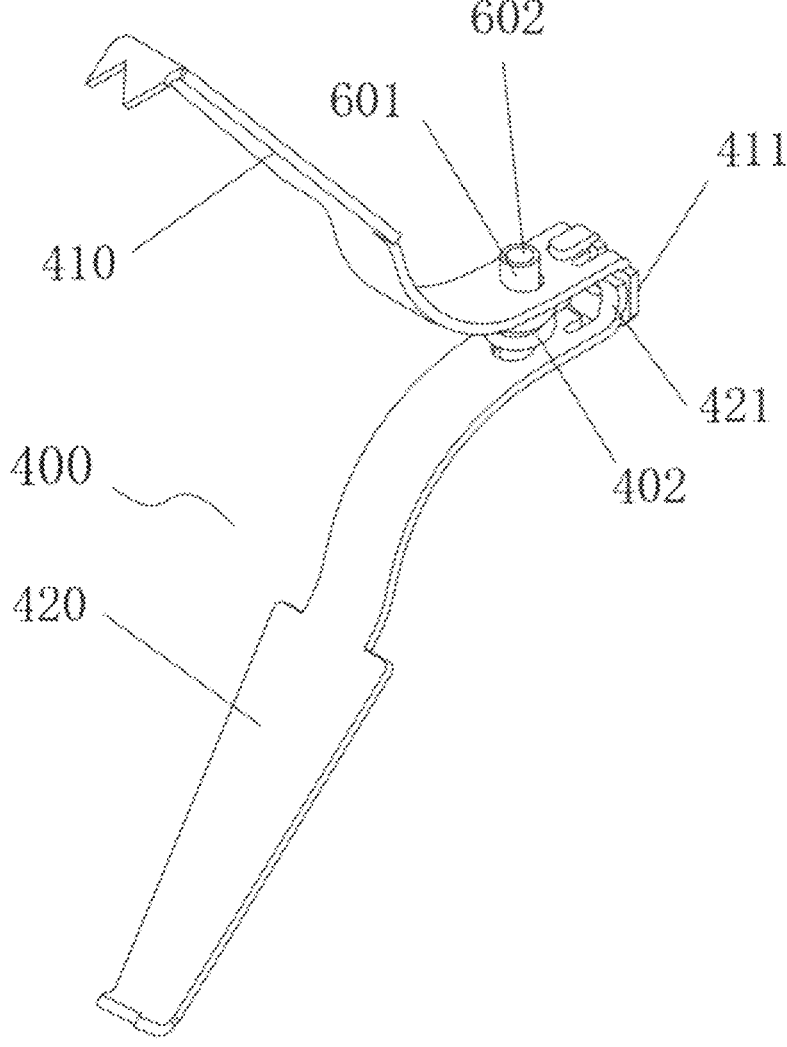
Figure 5:
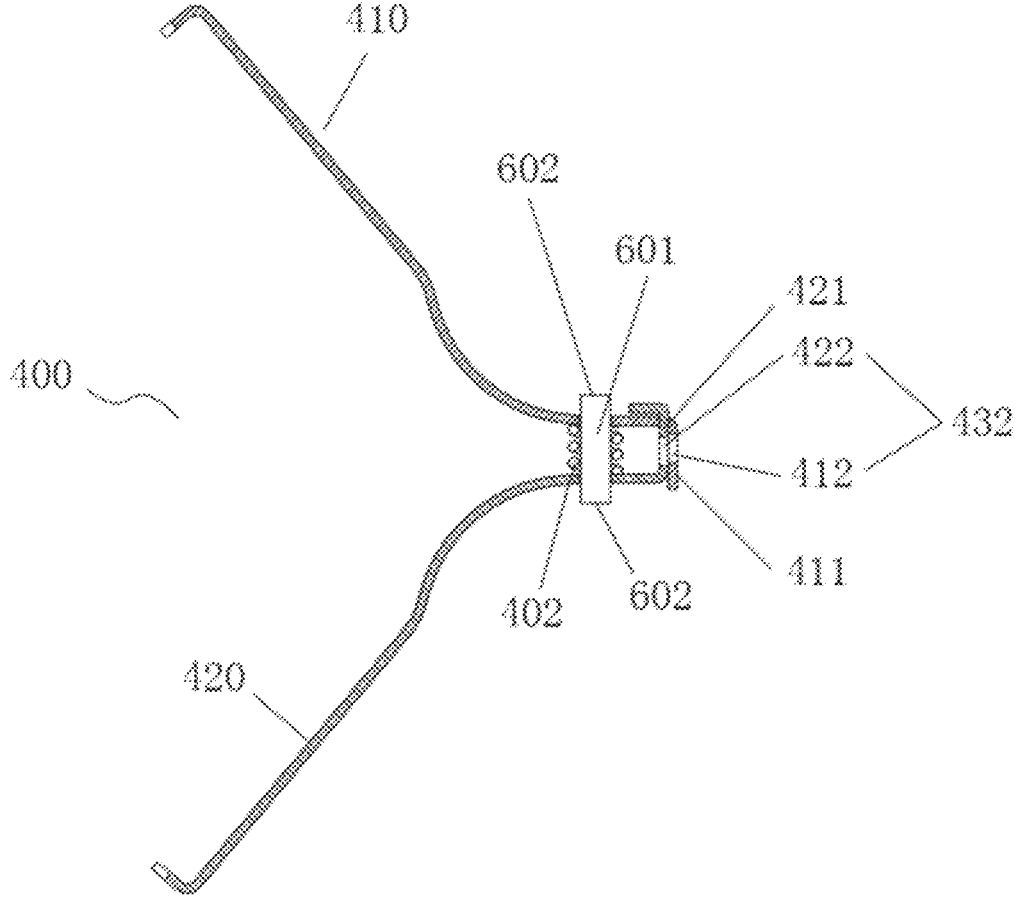
Figure 6:
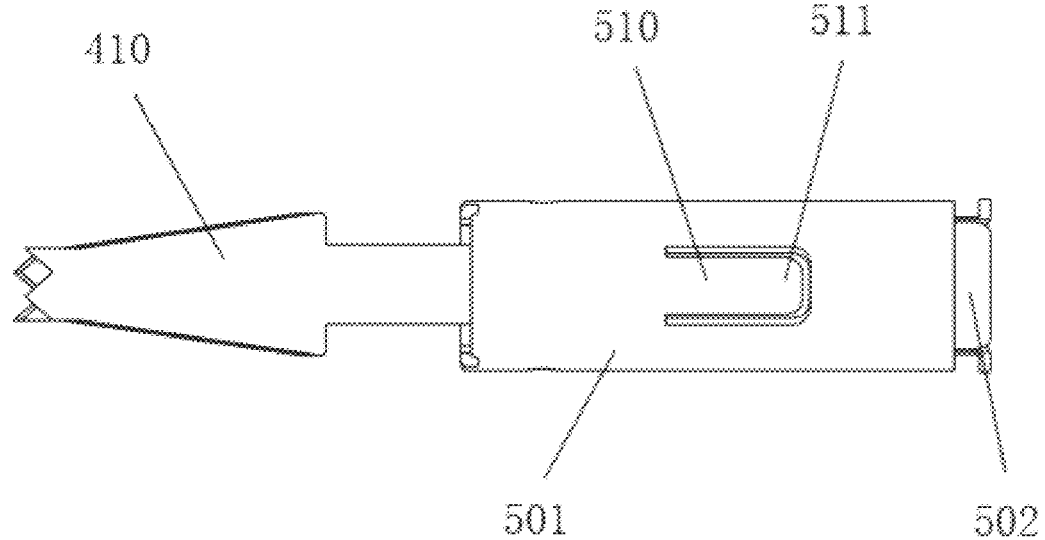
Figure 7:
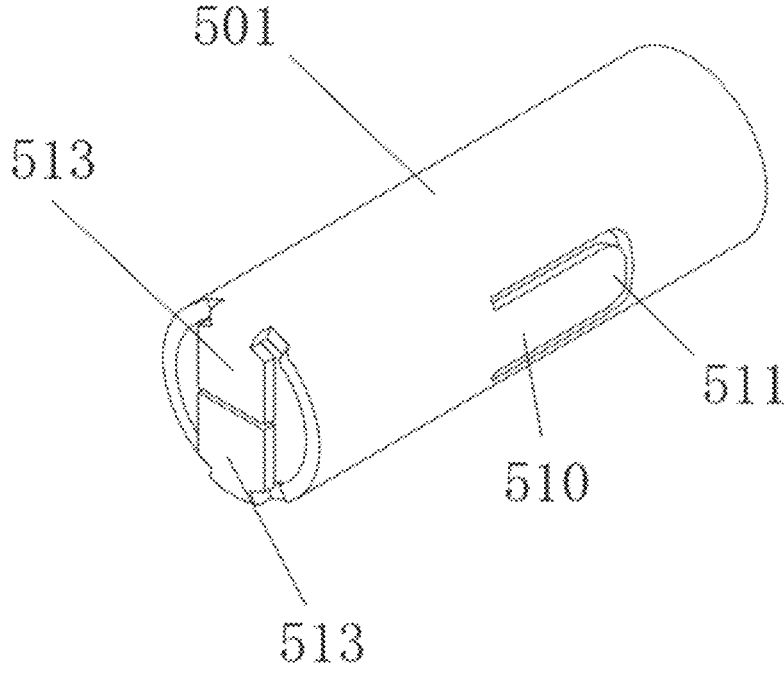
Figure 8:
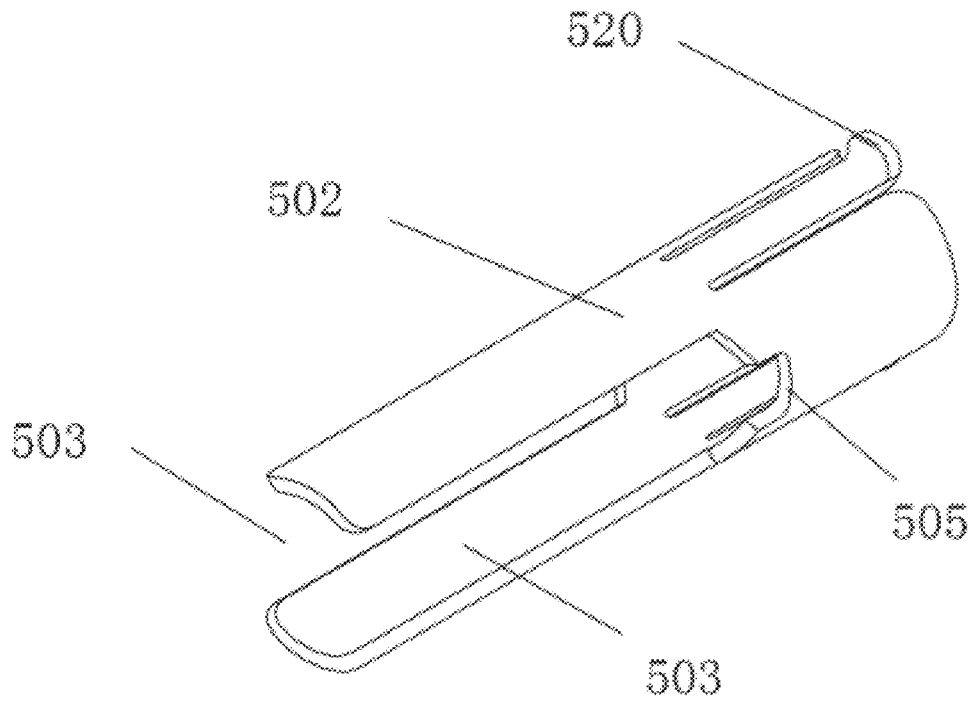
Figure 9:
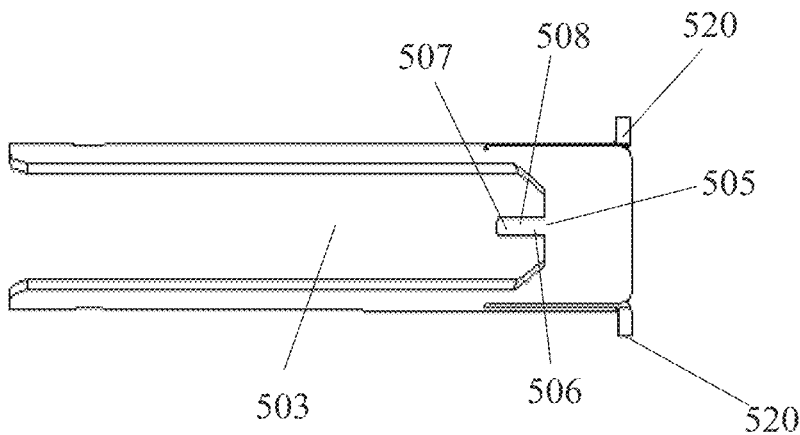
Figure 10:
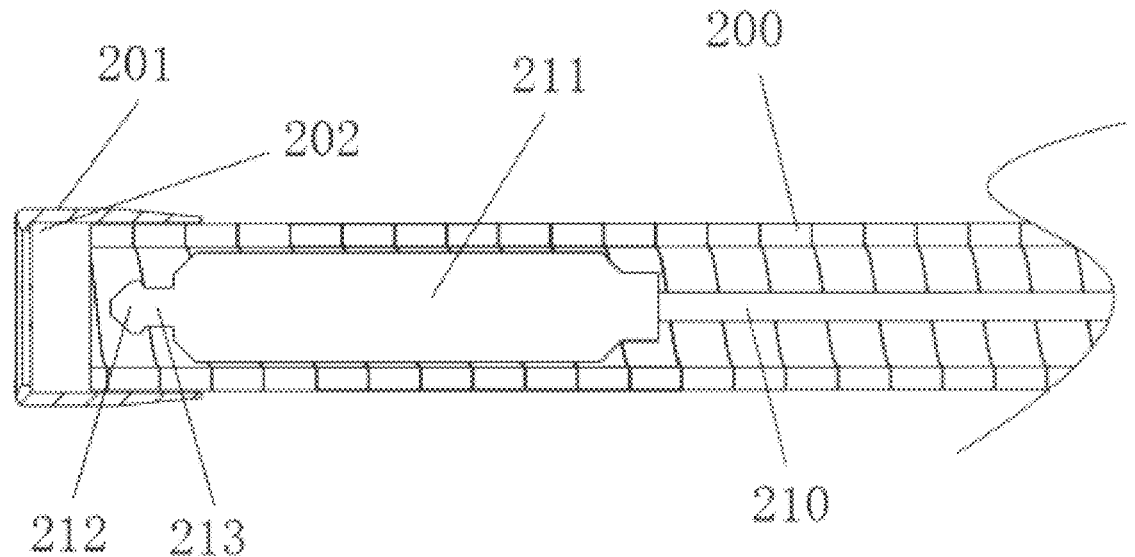
Figure 11:
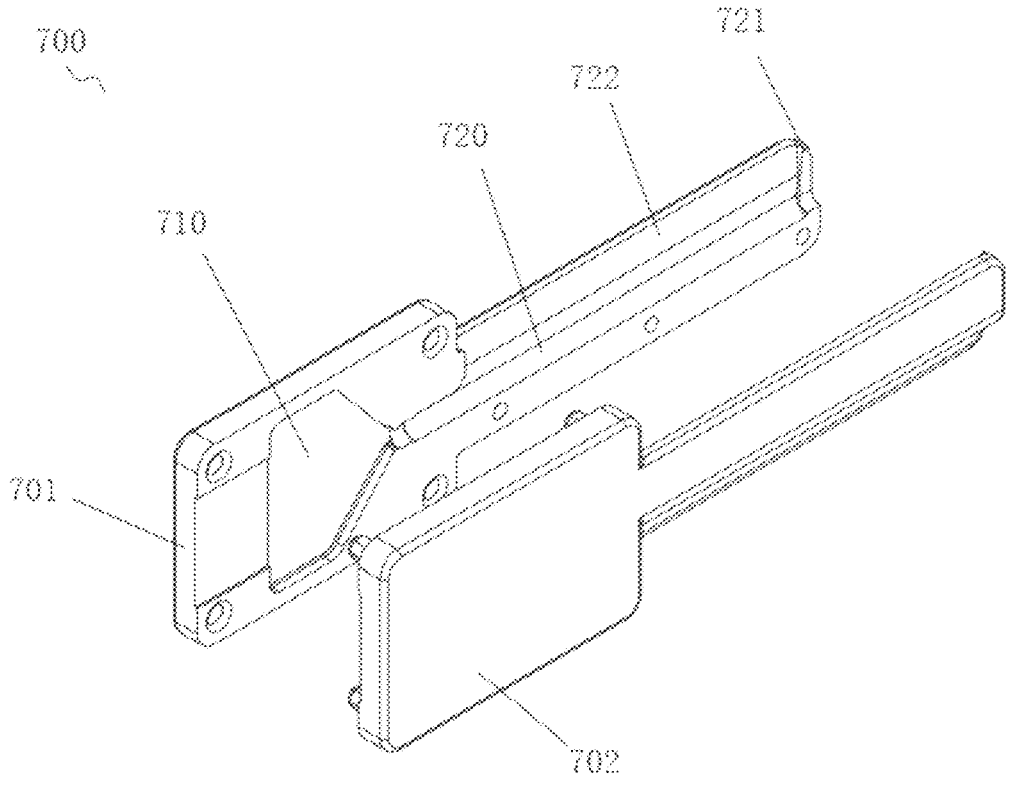
Figure 12:
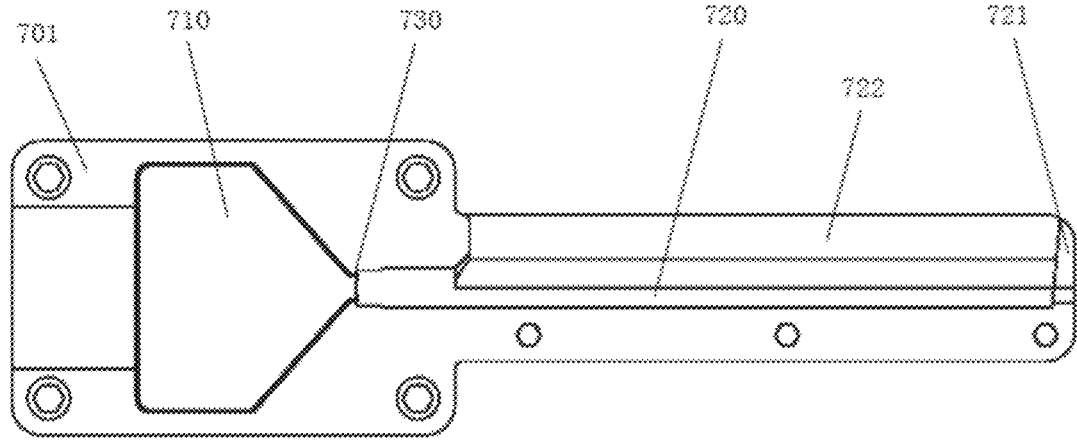
Figure 13:
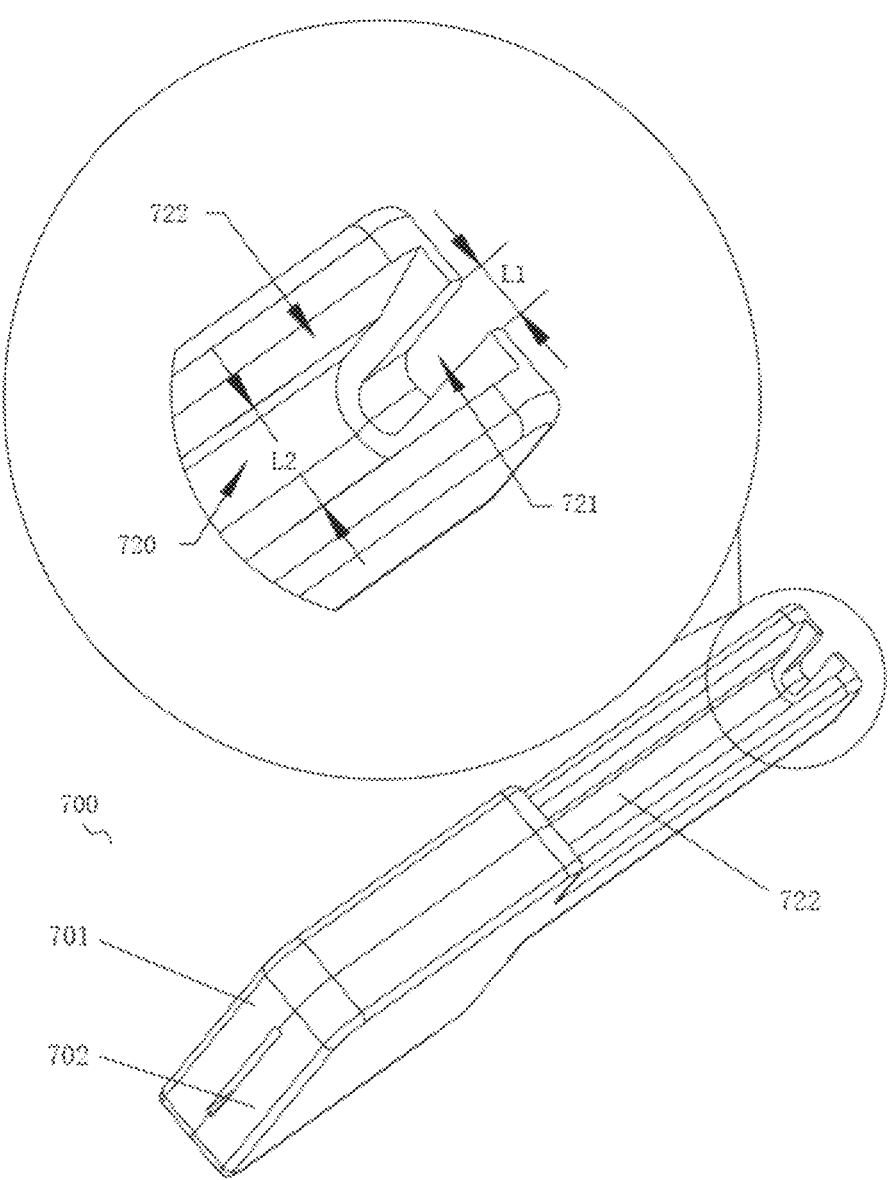
Figure 14:
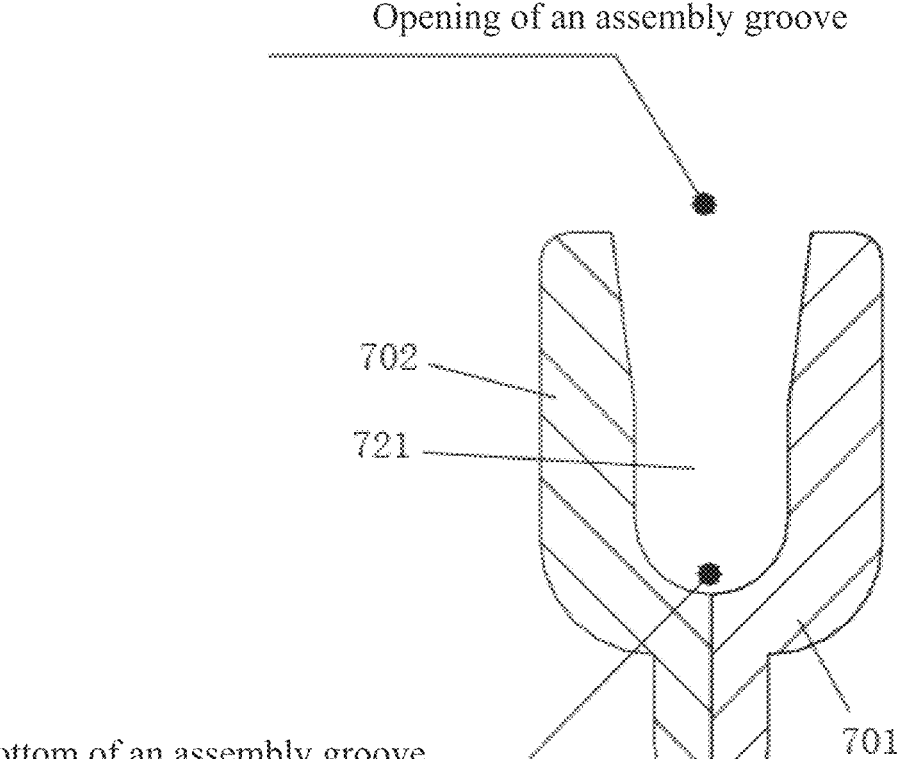
Figure 15:
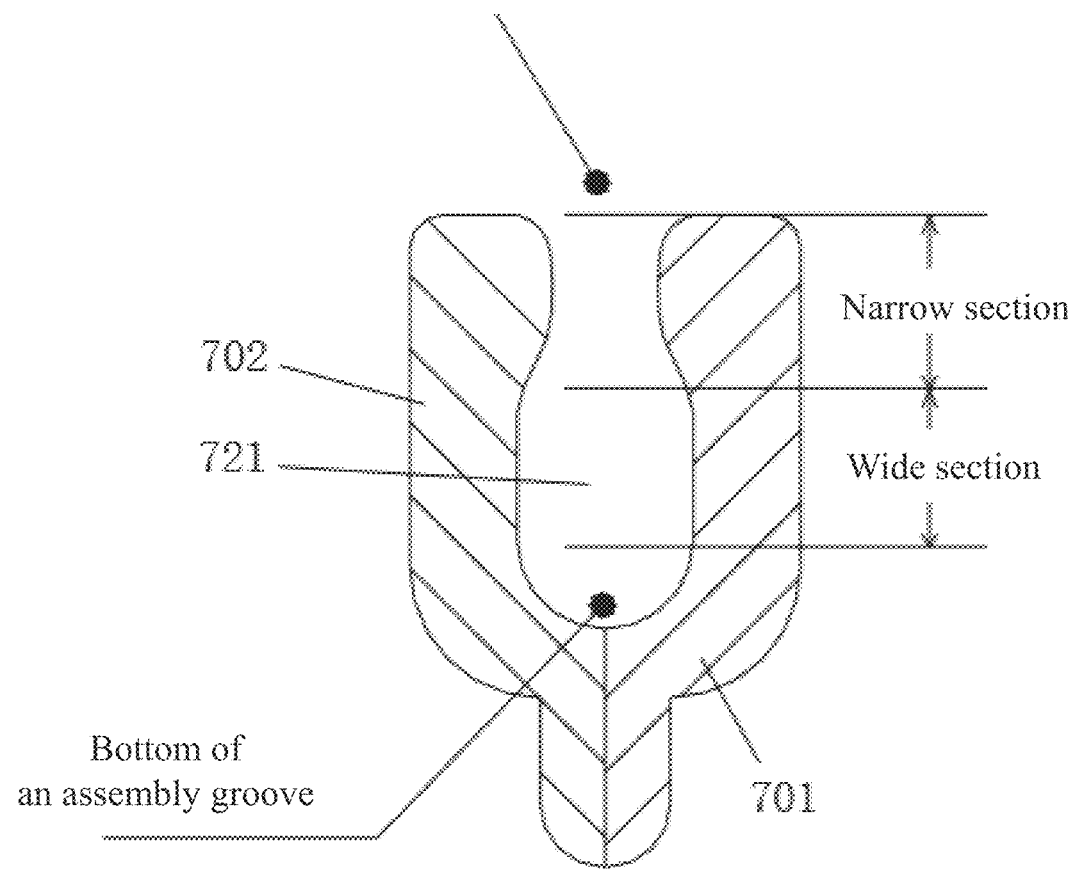
Figure 16:
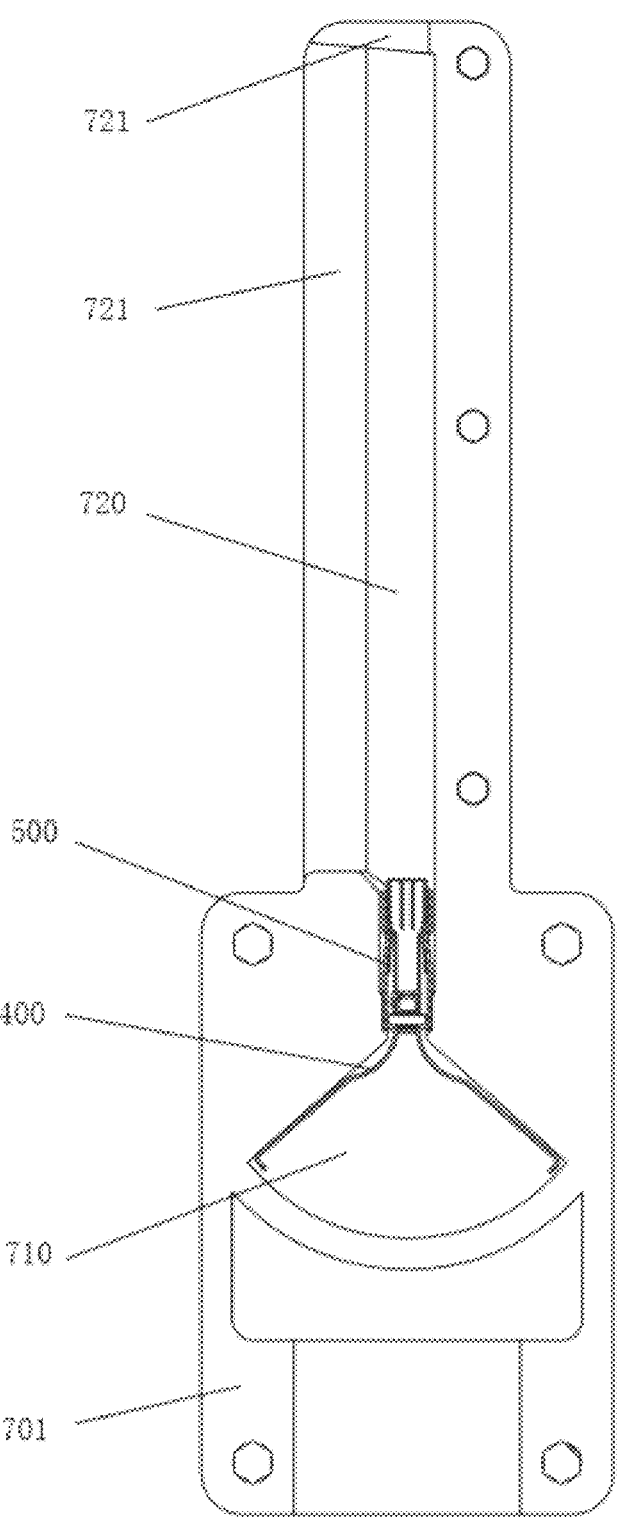
Figure 17:
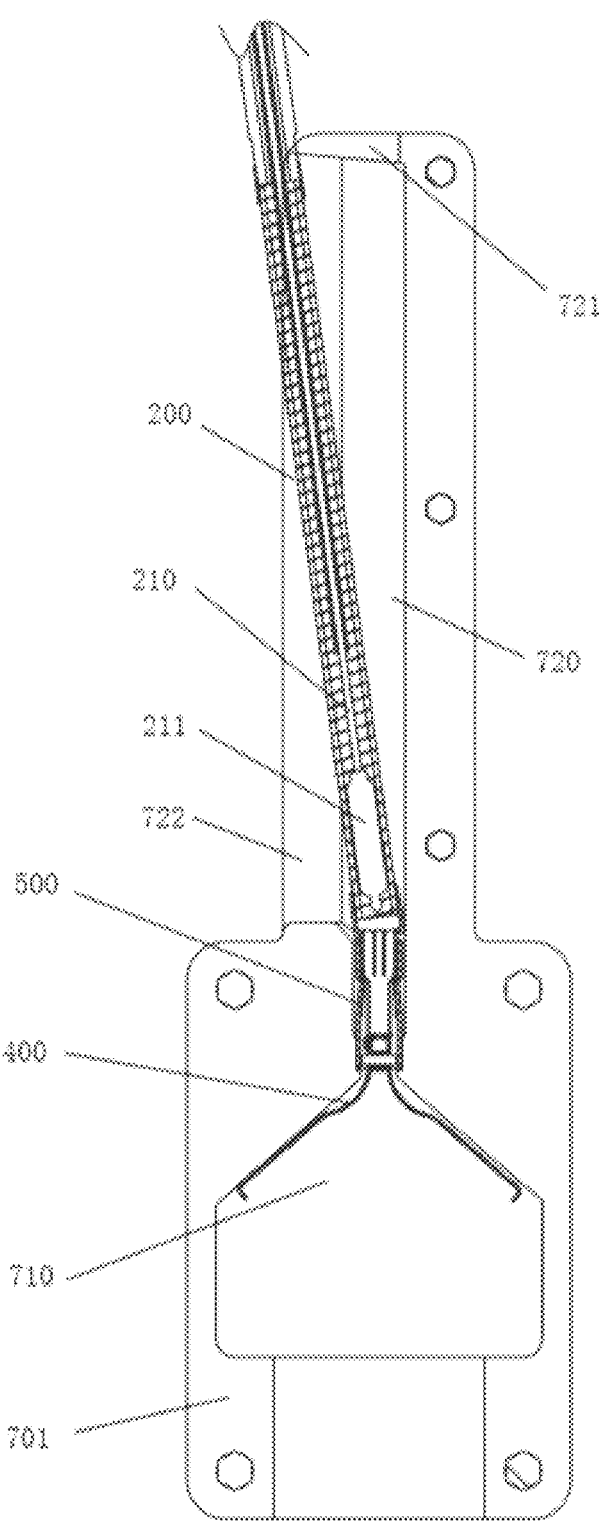
Figure 18:
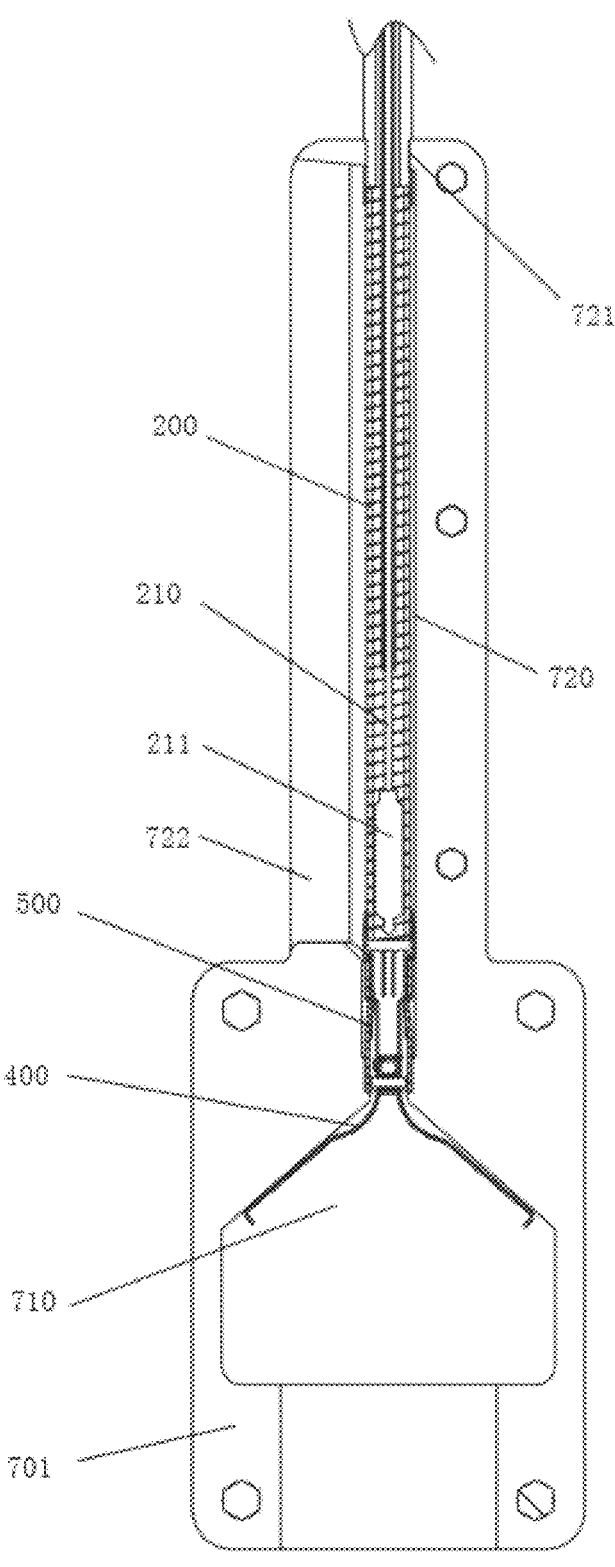
Figure 19:
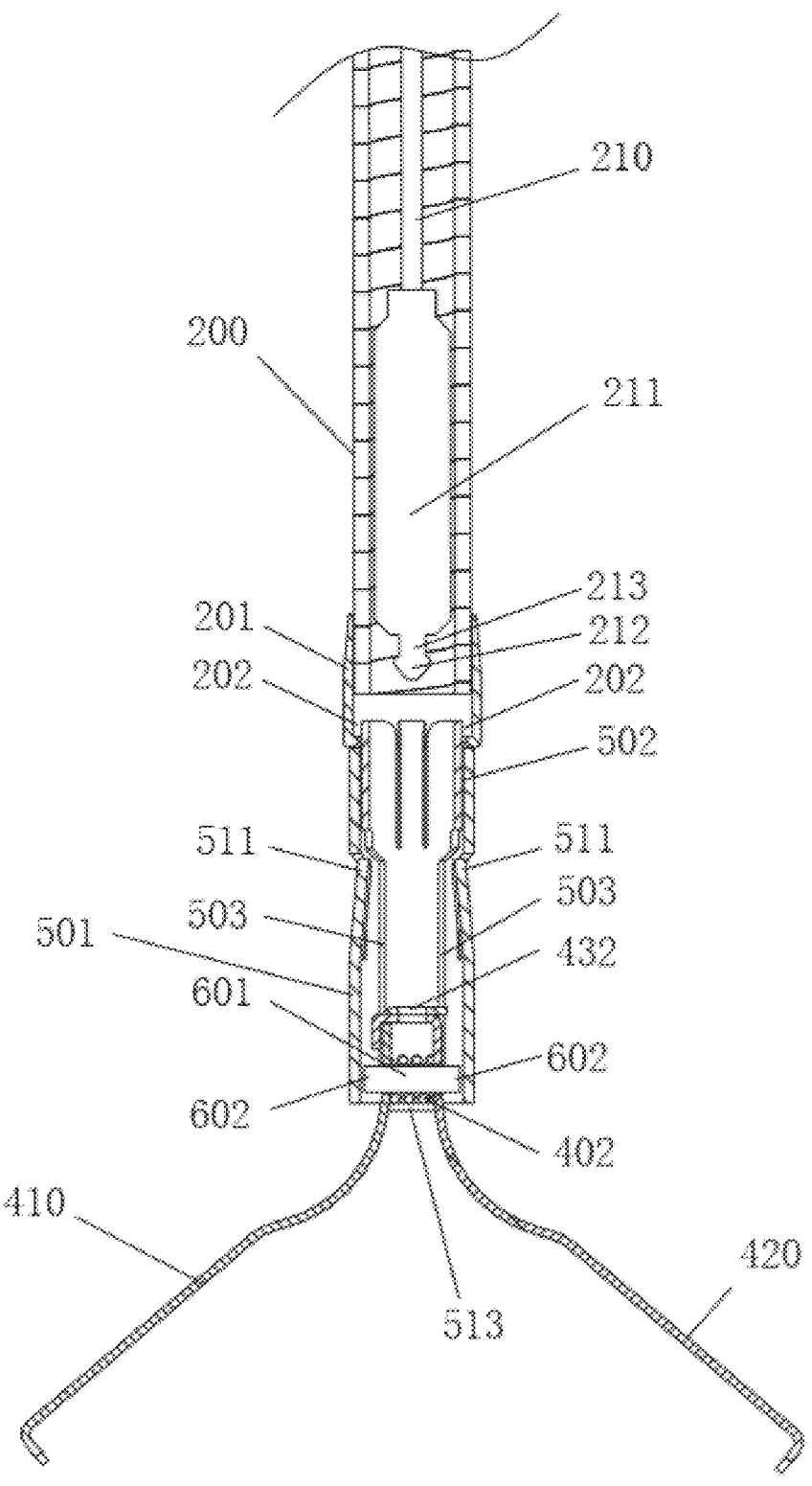
Figure 20:
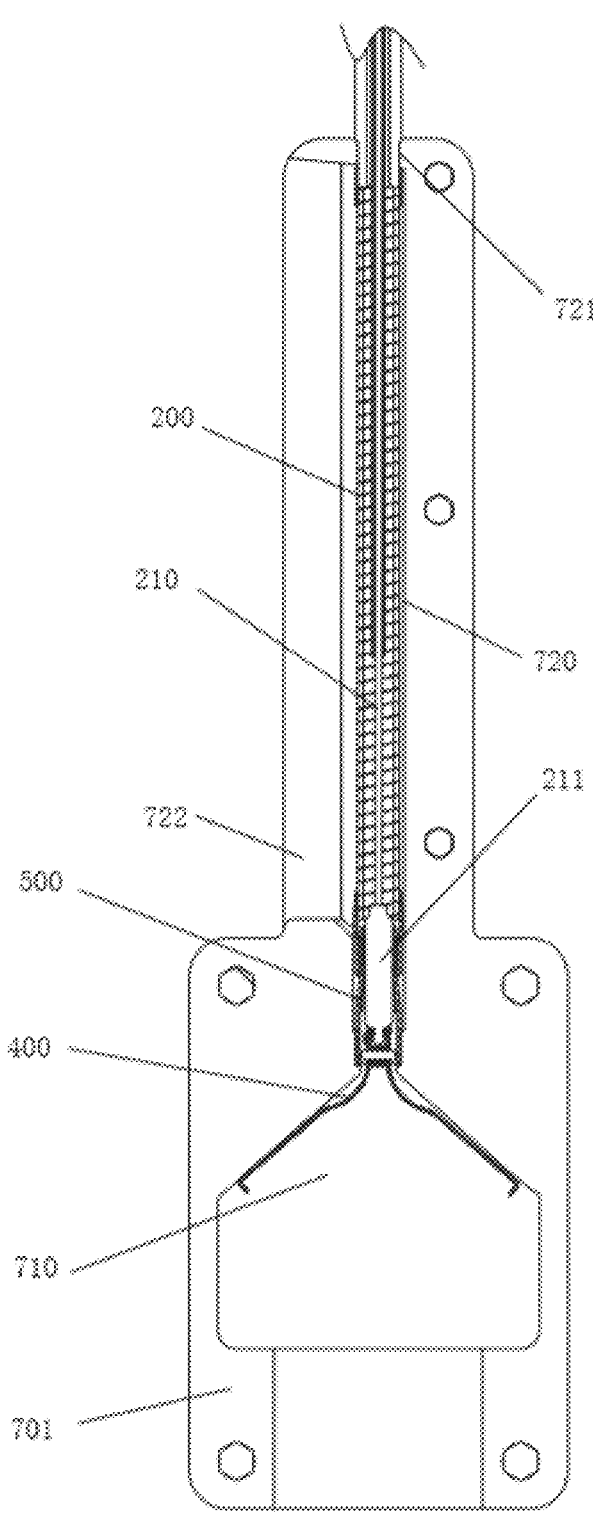
Figure 21:
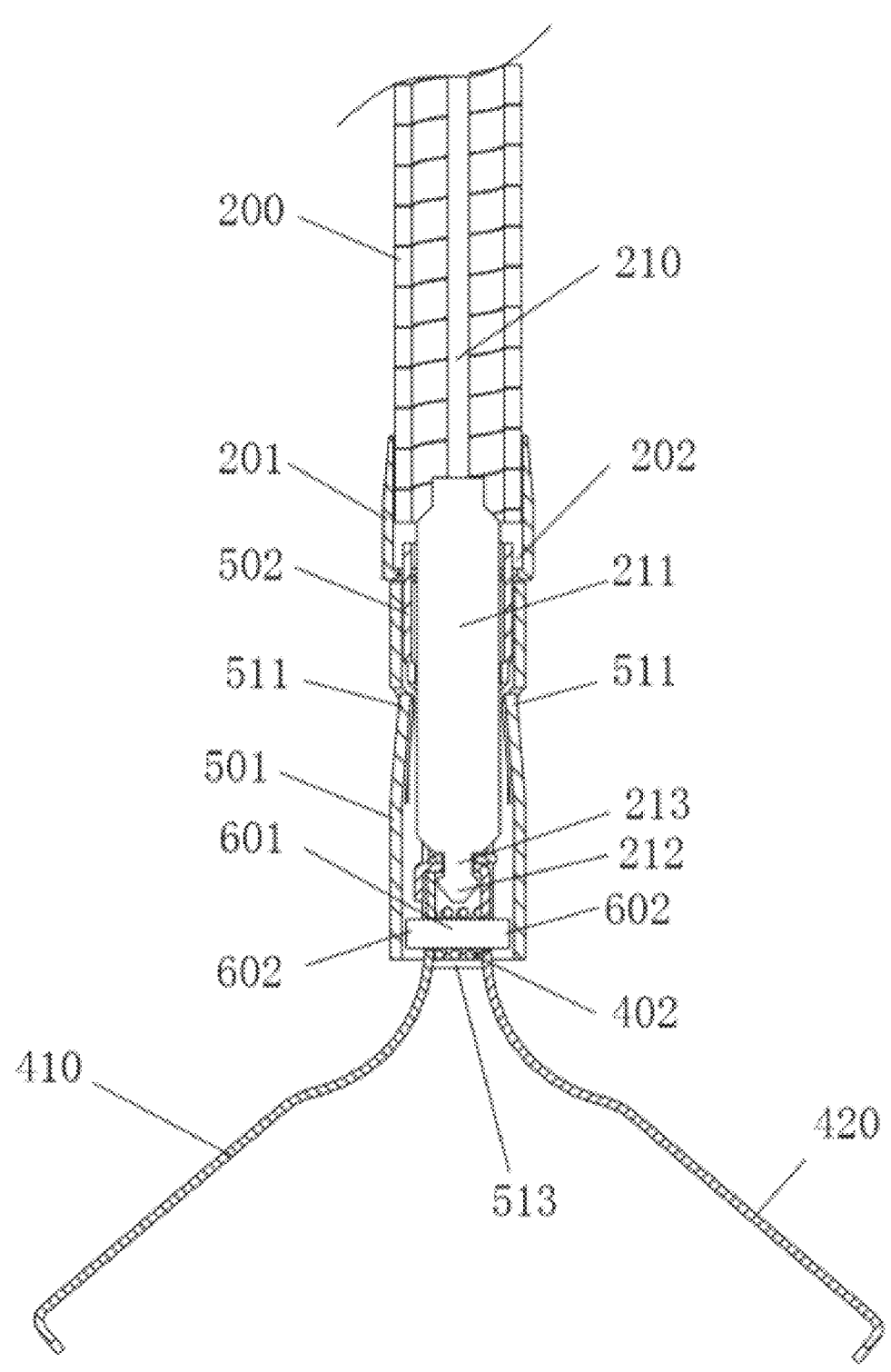
Figure 22:
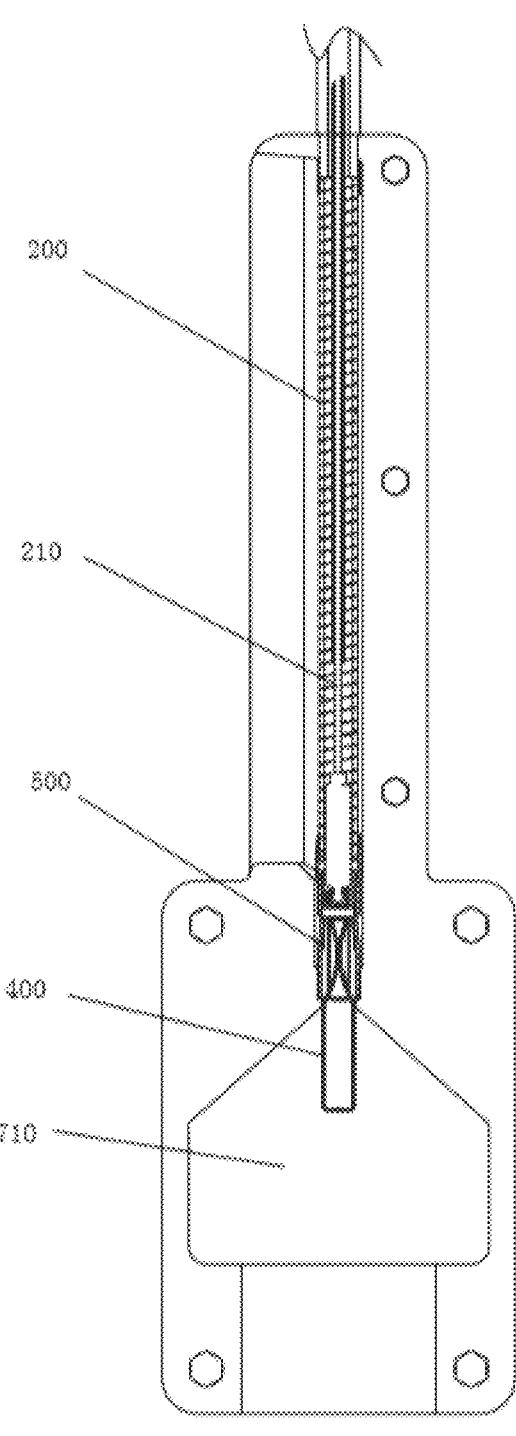
Figure 23:
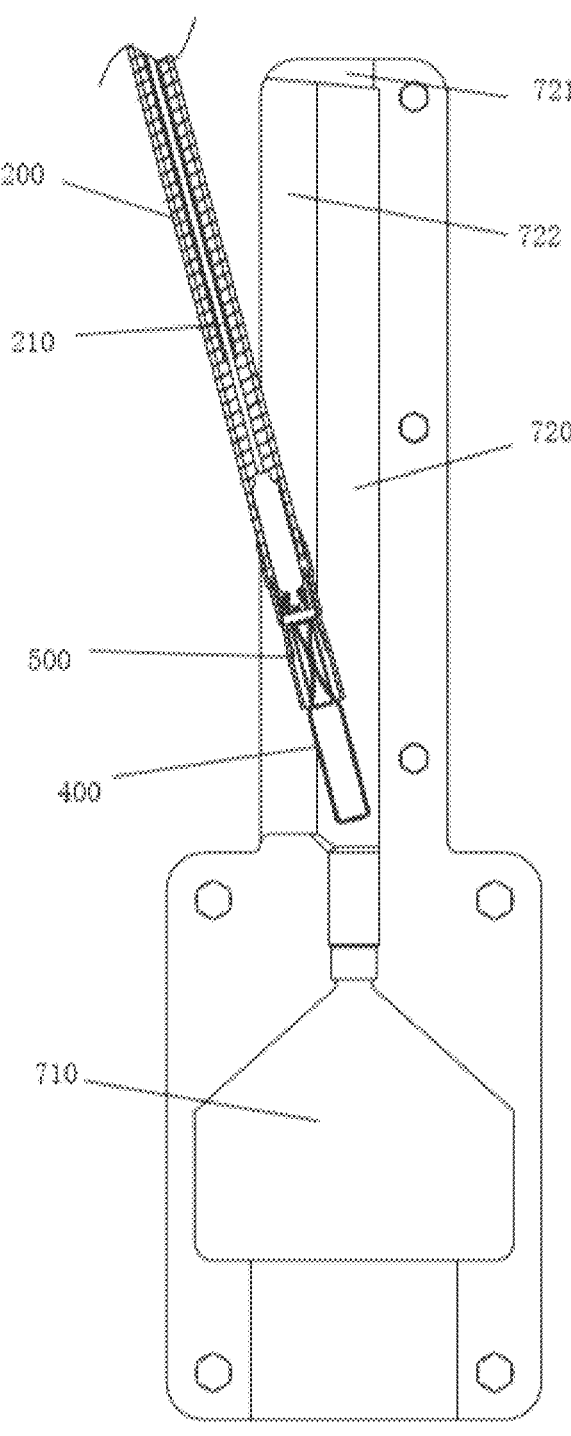
Figure 24:
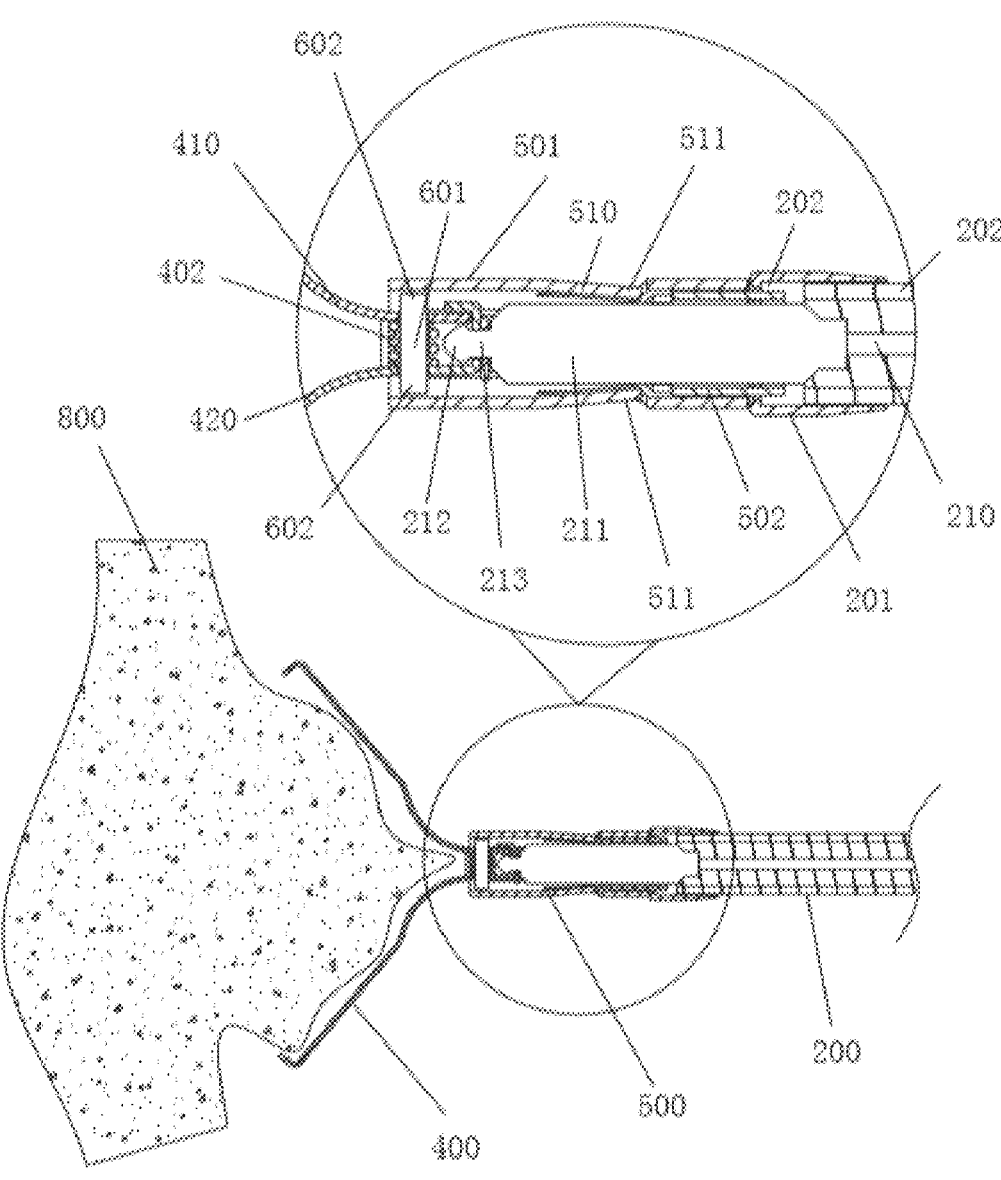
Figure 25:
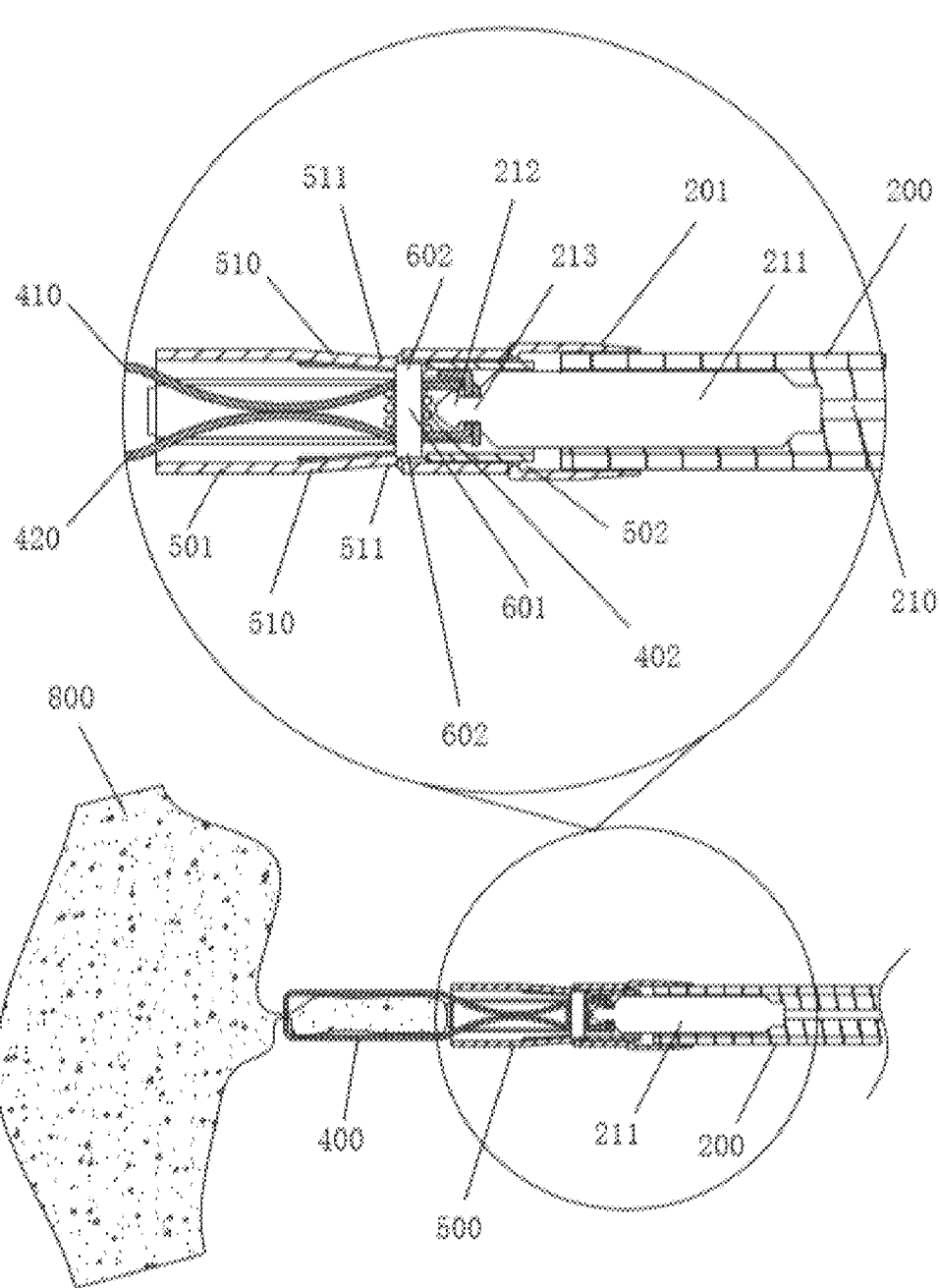
Figure 26:
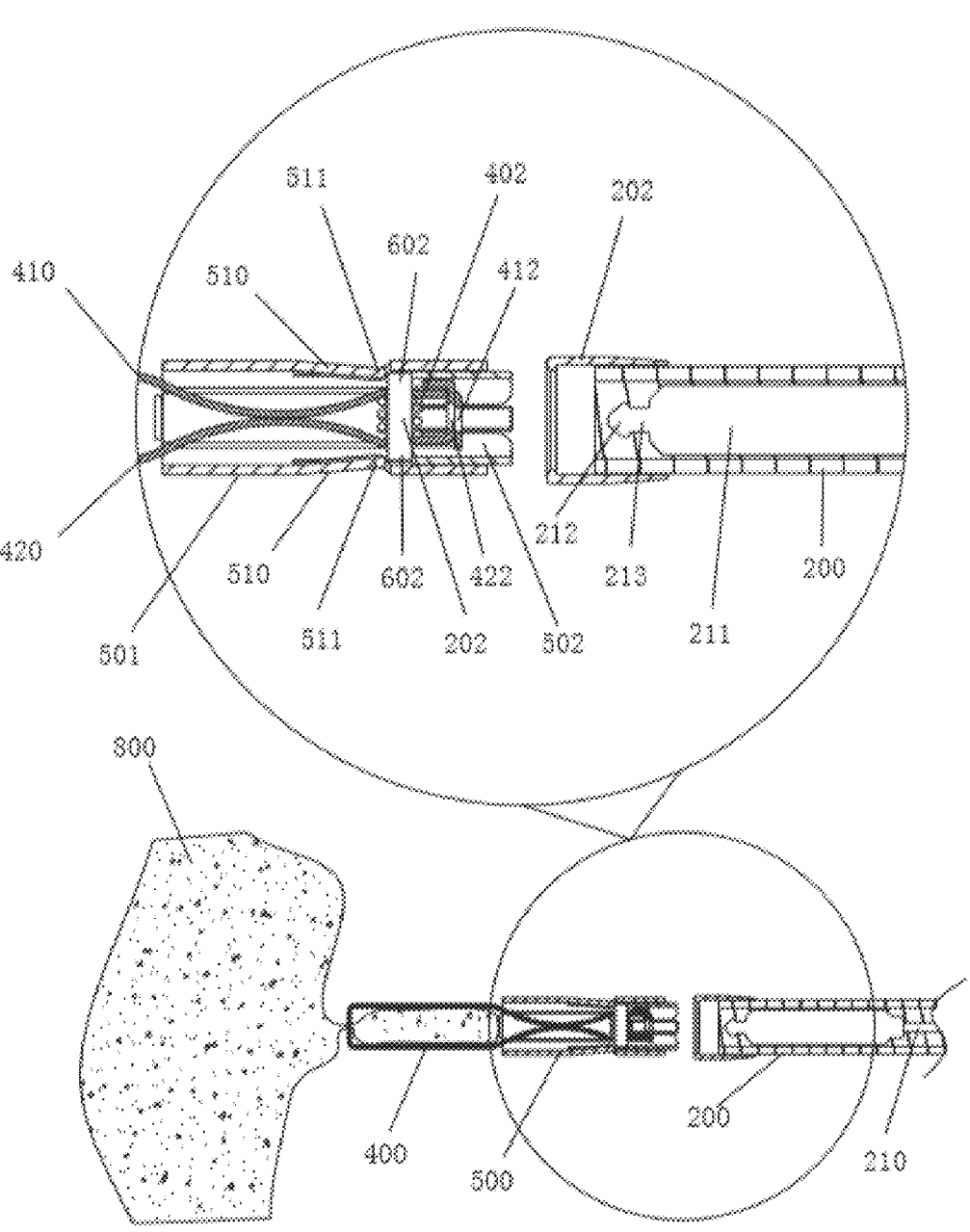
Figure 27:
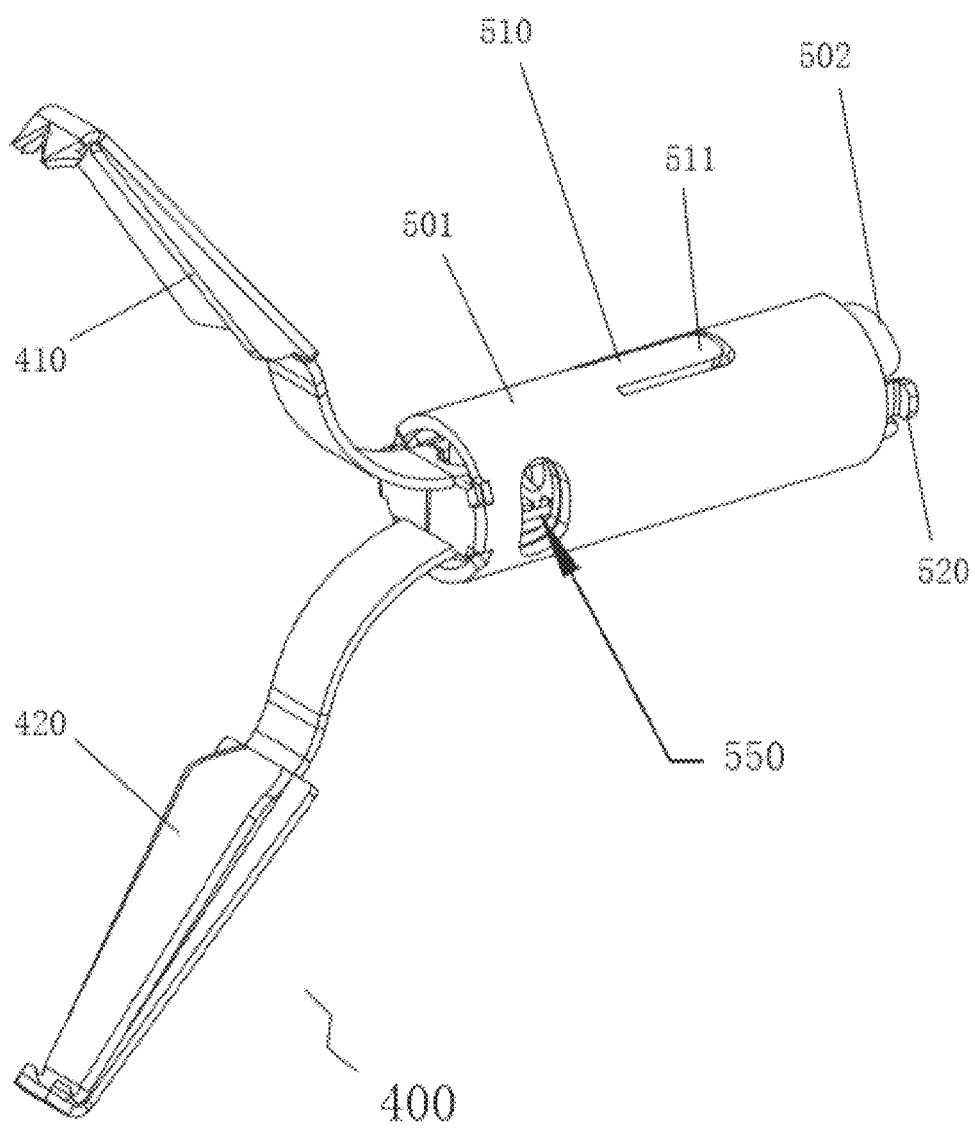
Figure 28:
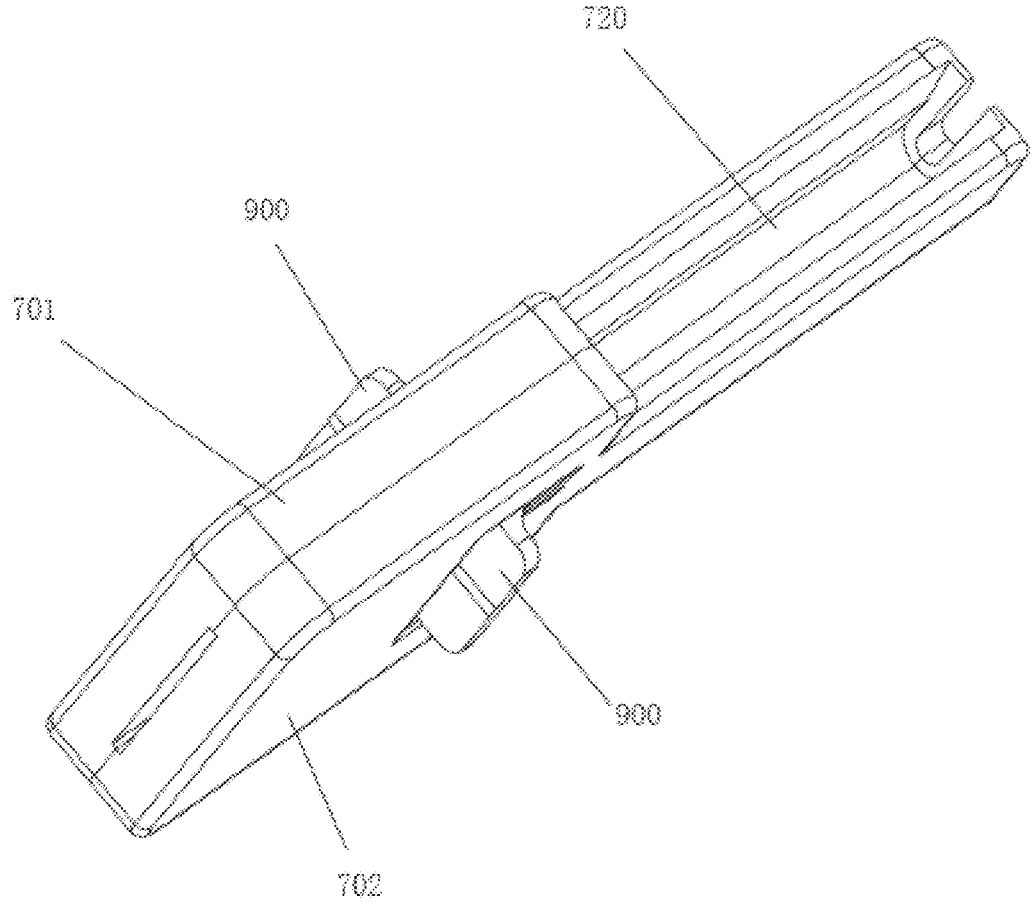
Figure 29:
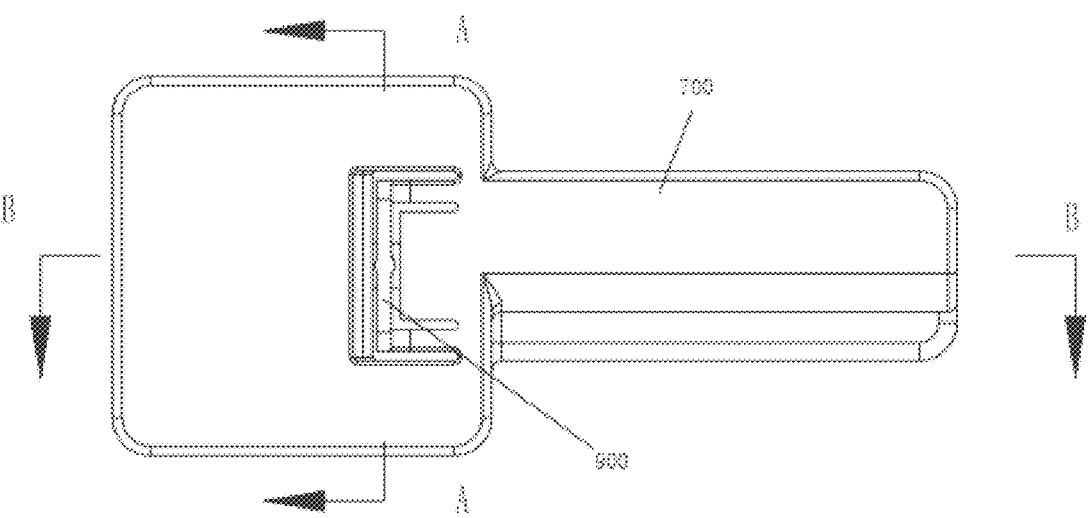
Figure 30:
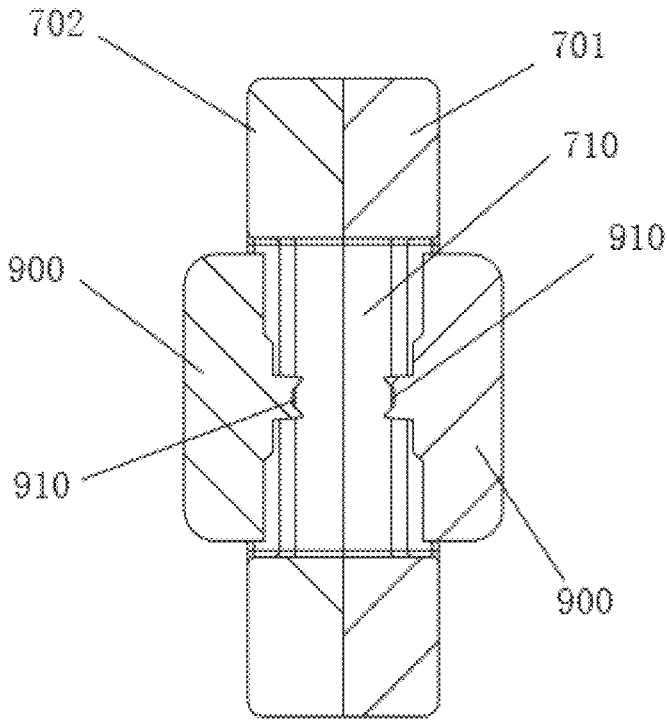
Figure 31:
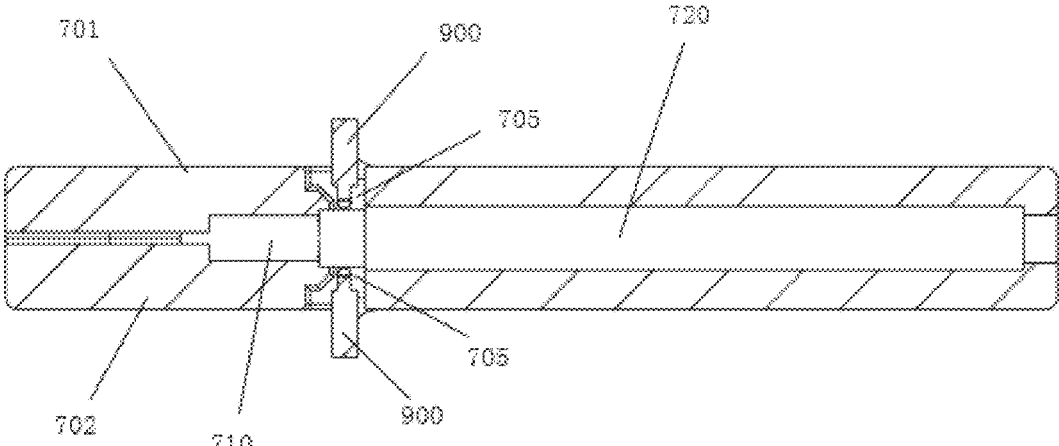
Figure 32:
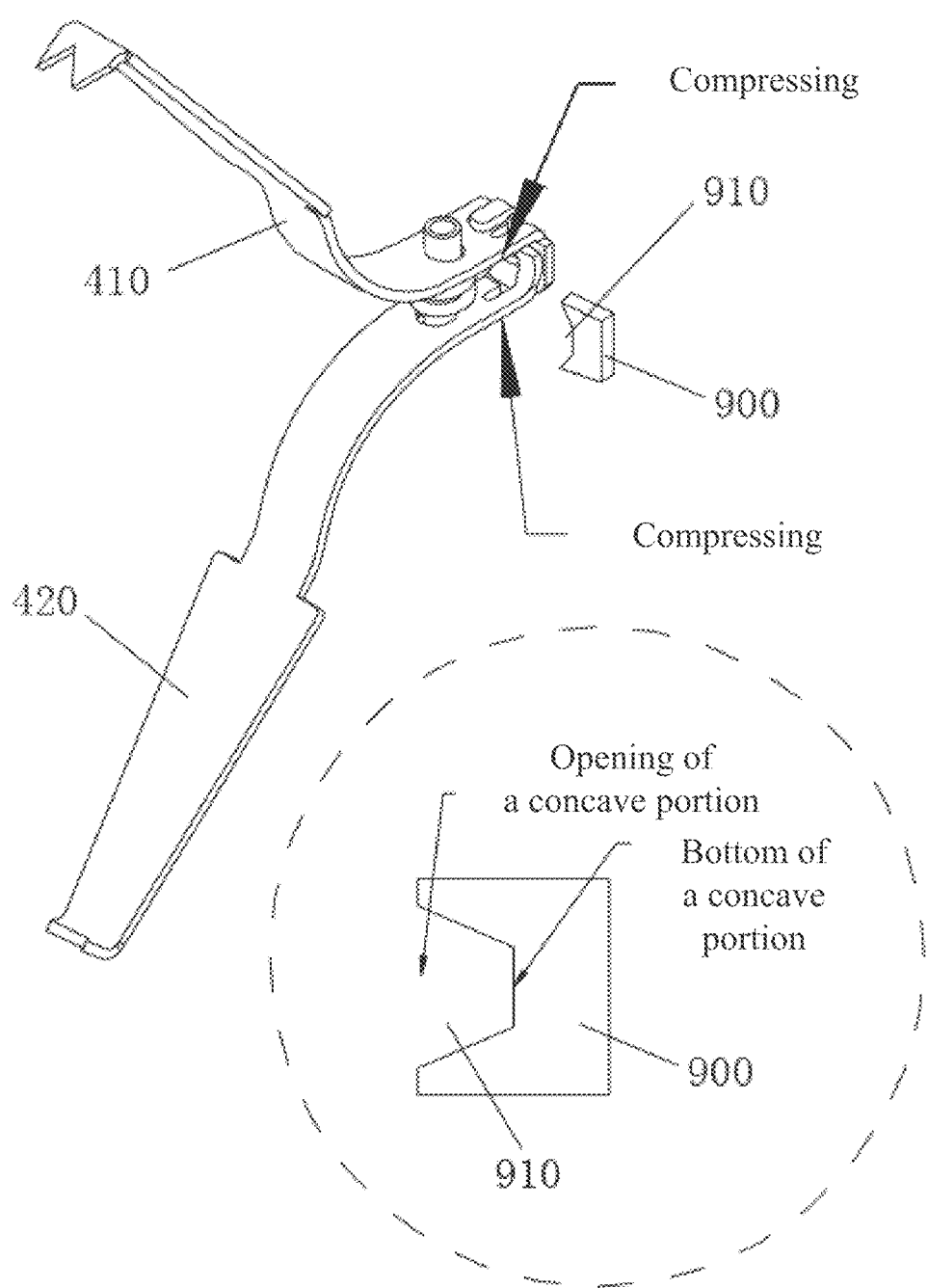
Figure 33:
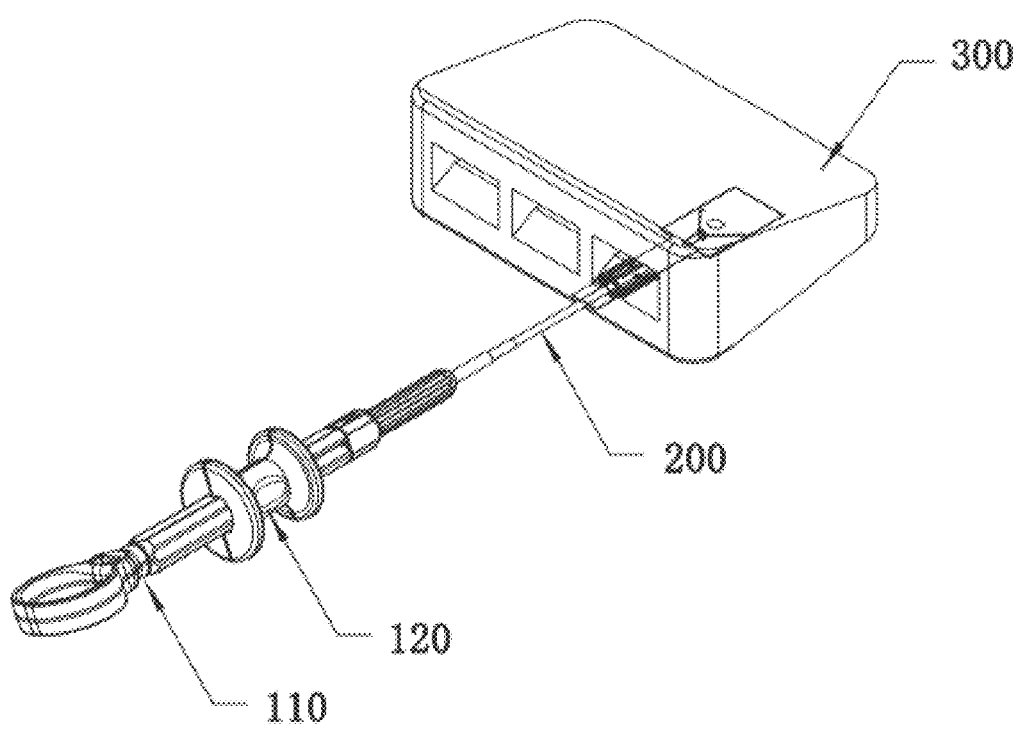
Figure 34:
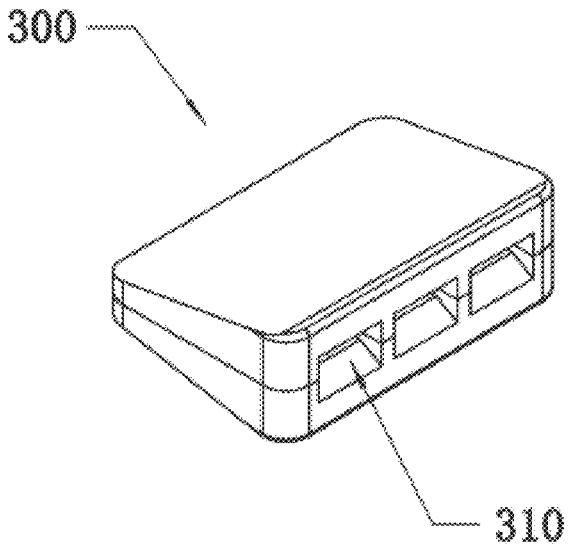
Figure 35:
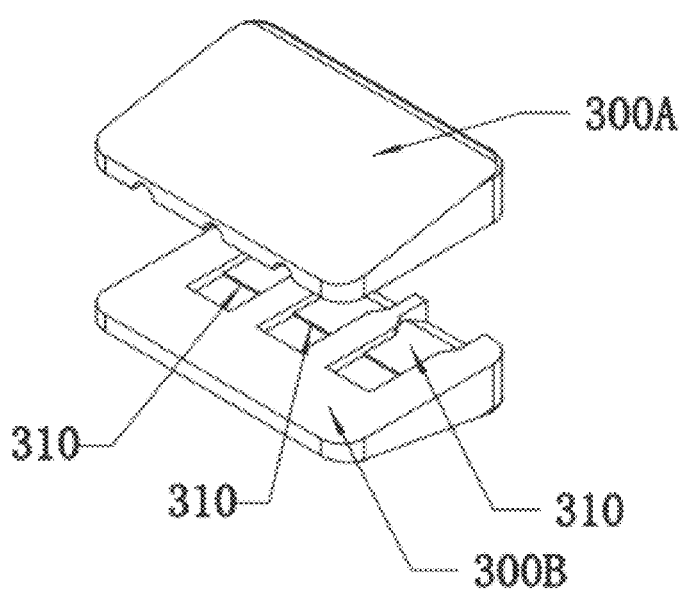
Figure 36:
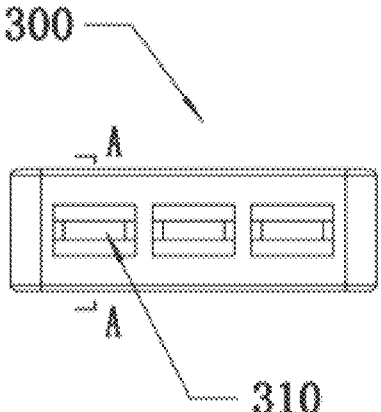
Figure 37:
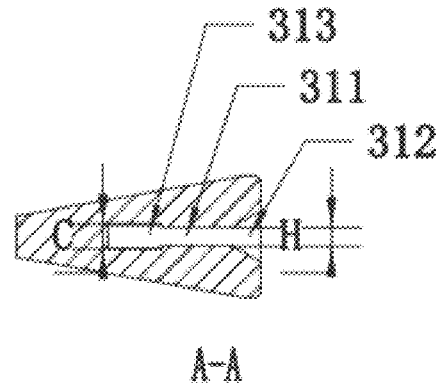
Figure 38:
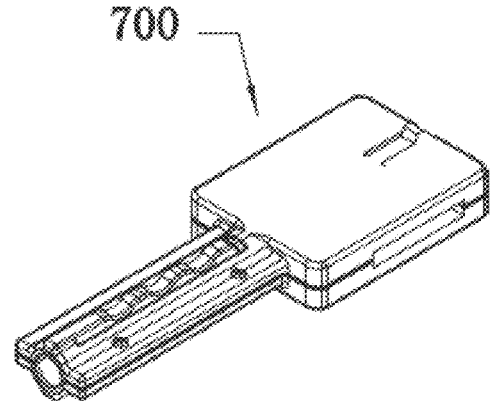
Figure 39:
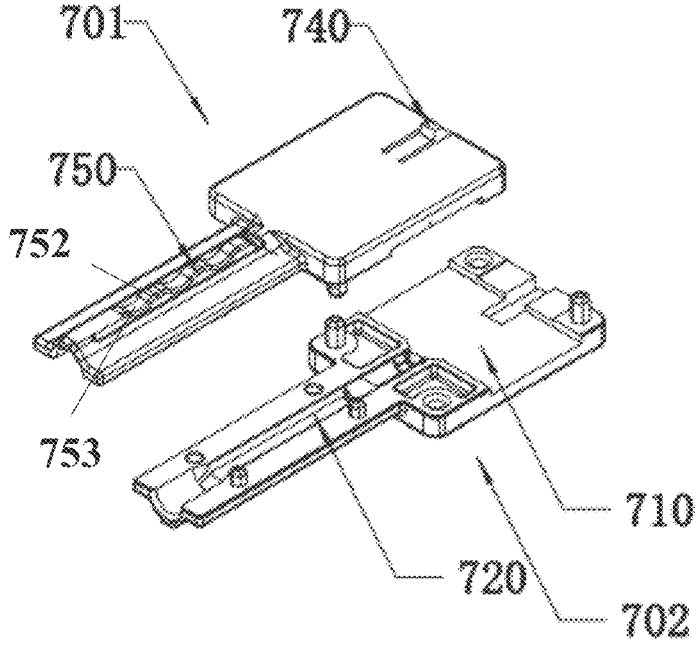
Figure 40:
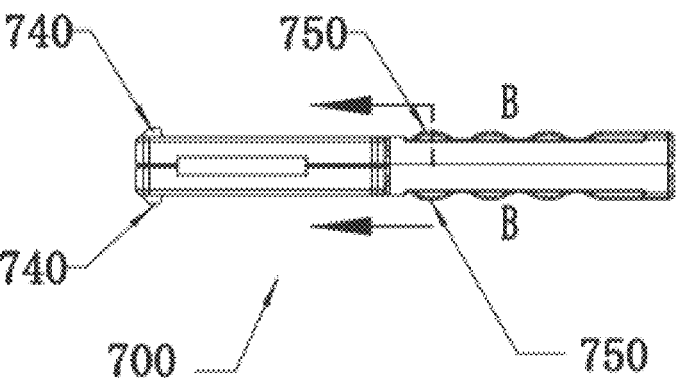
Figure 41:
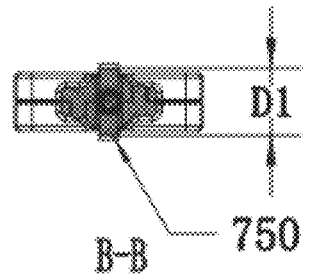
Figure 42:
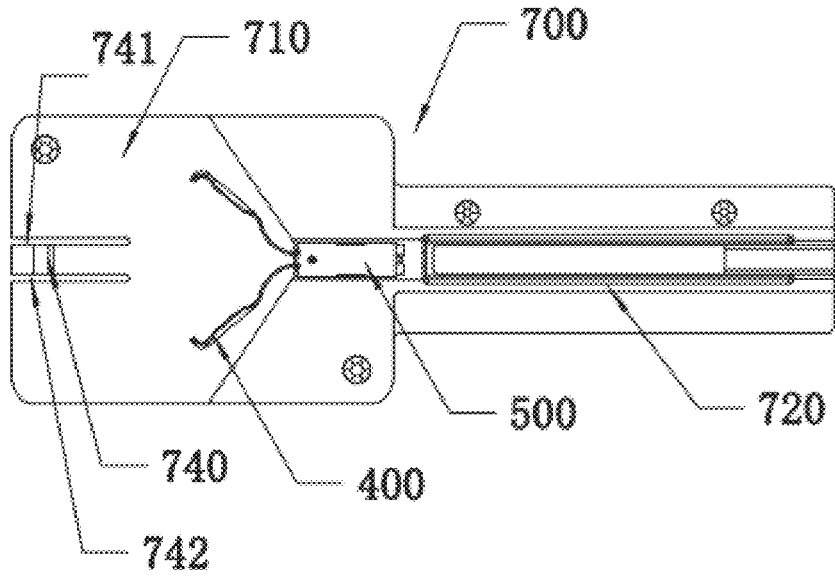
Figure 43:
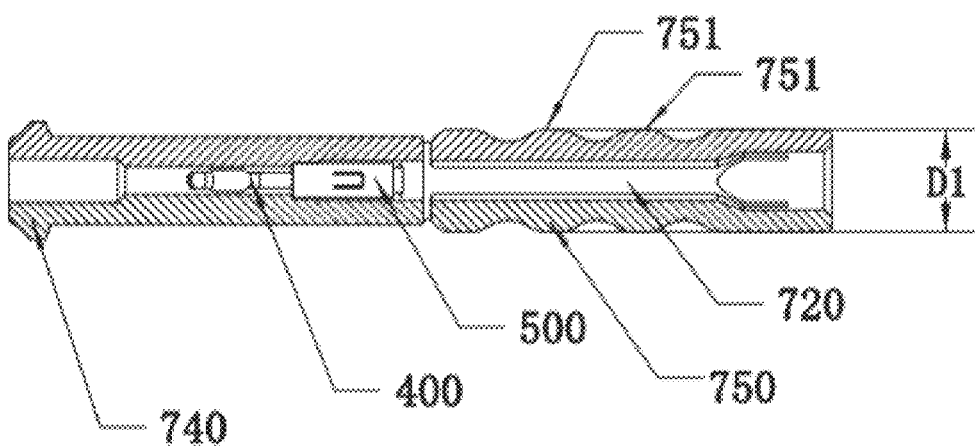
Figure 44:
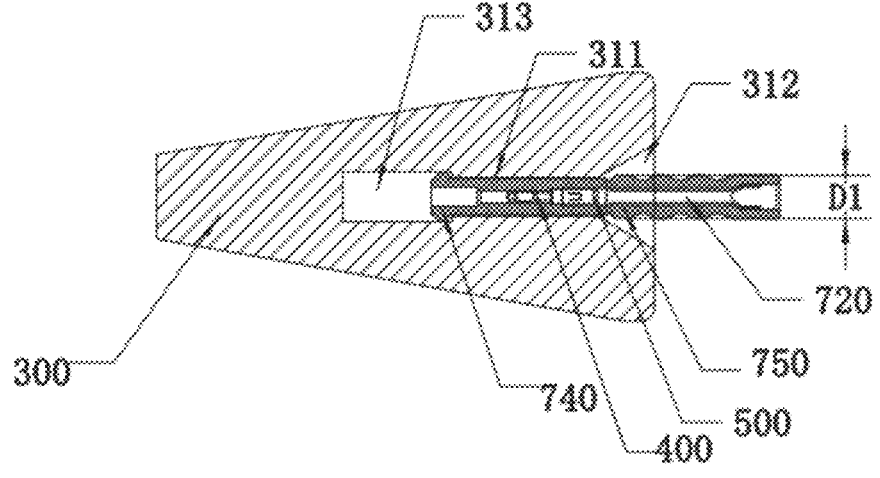
Figure 45:
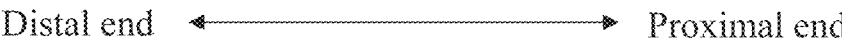
Figure 45:
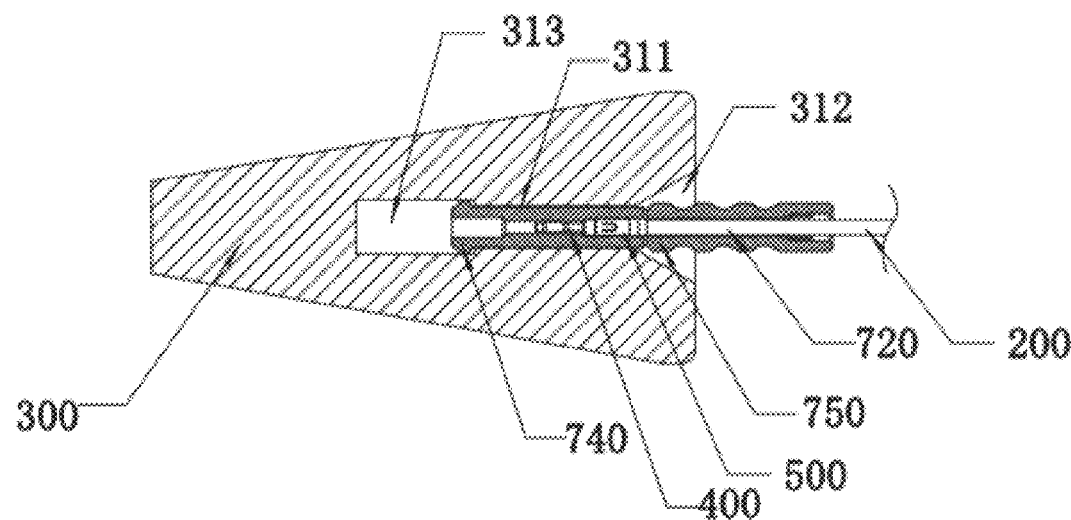
Figure 46:
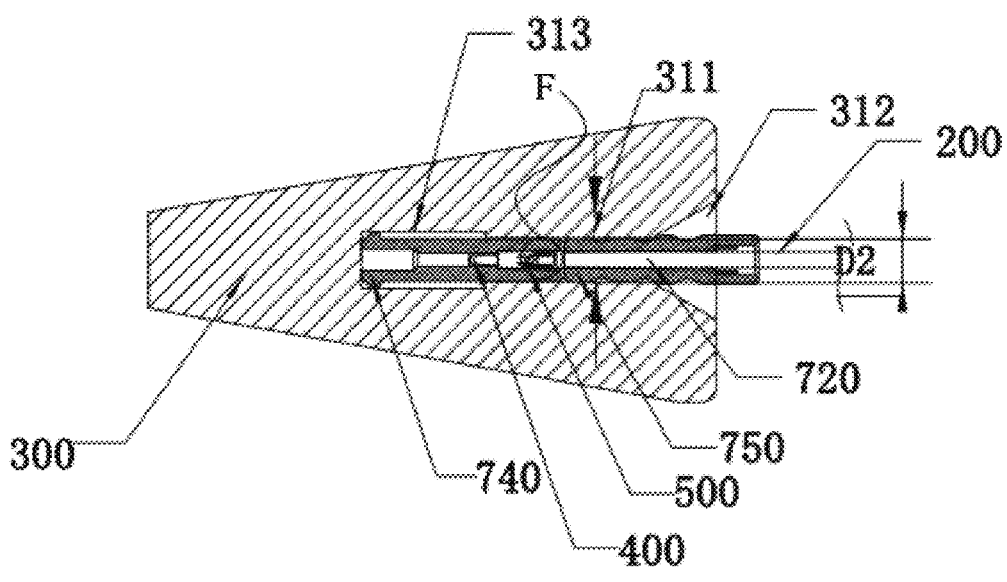
Figure 47:
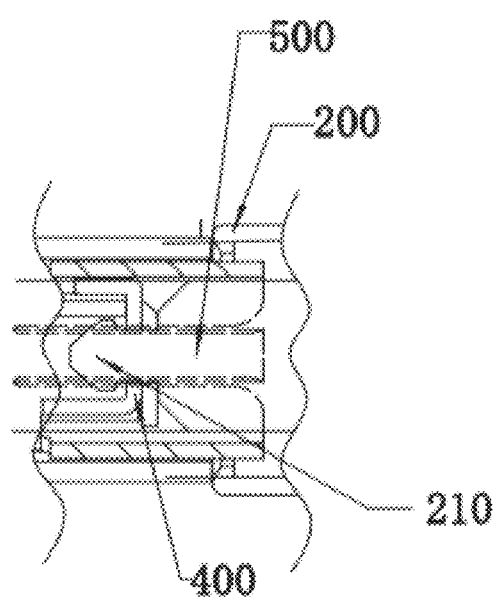
Figure 48:
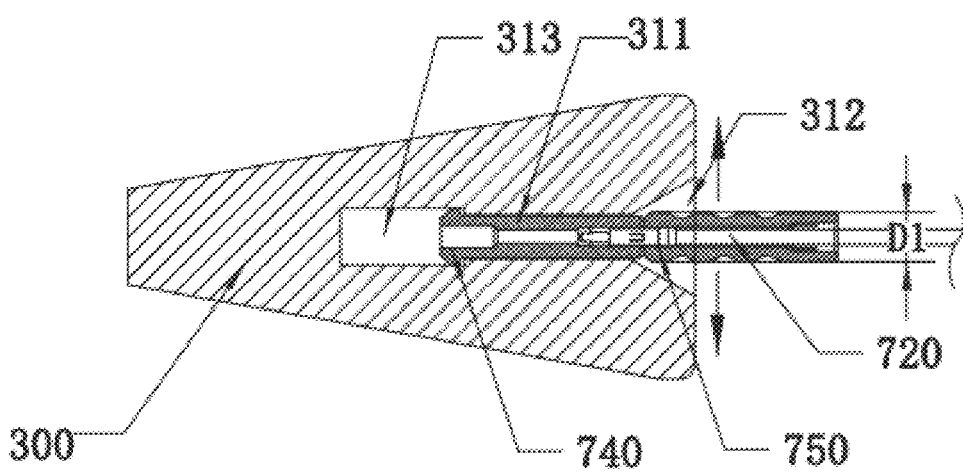
Figure 49:
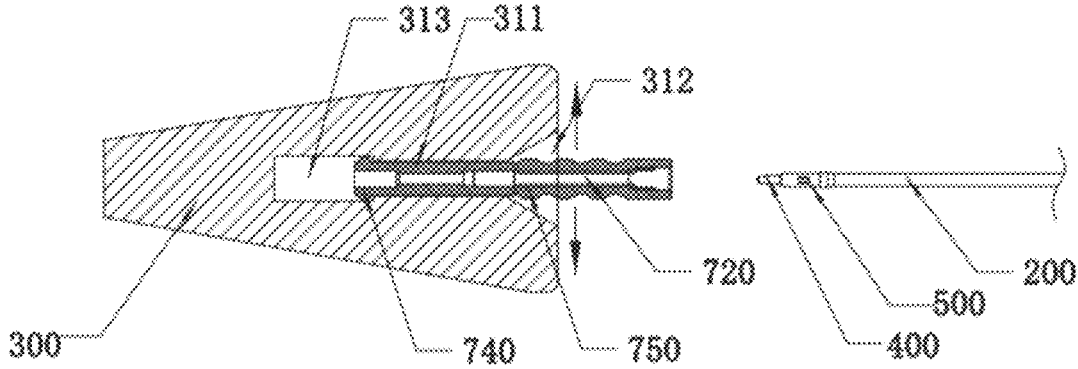
Figure 50:
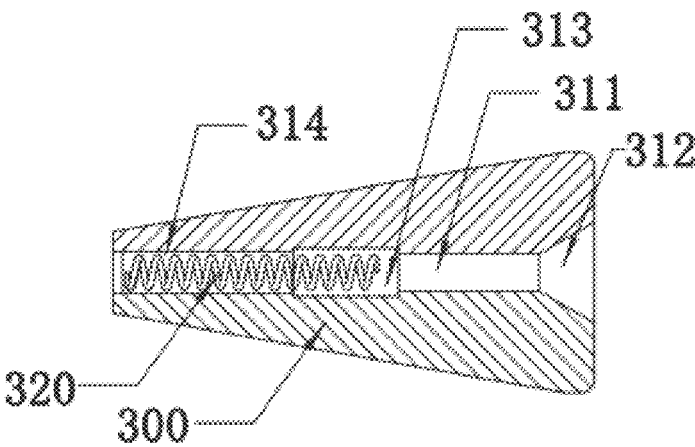
Figure 51:
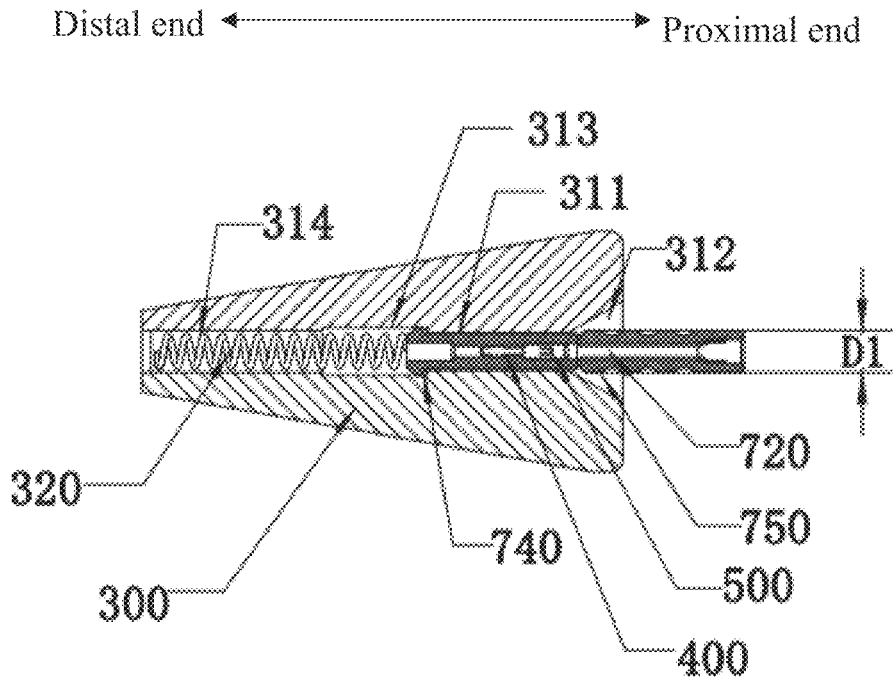
Figure 52:
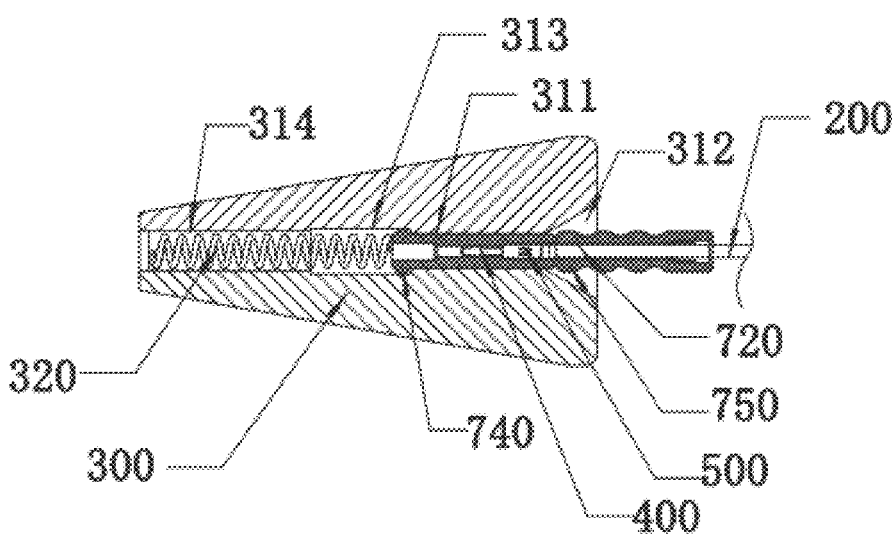
Figure 53:
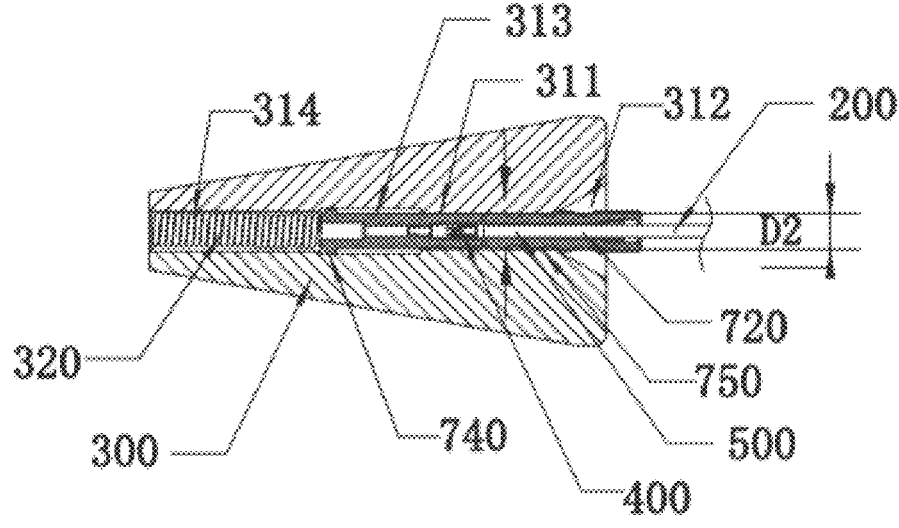
Figure 54:
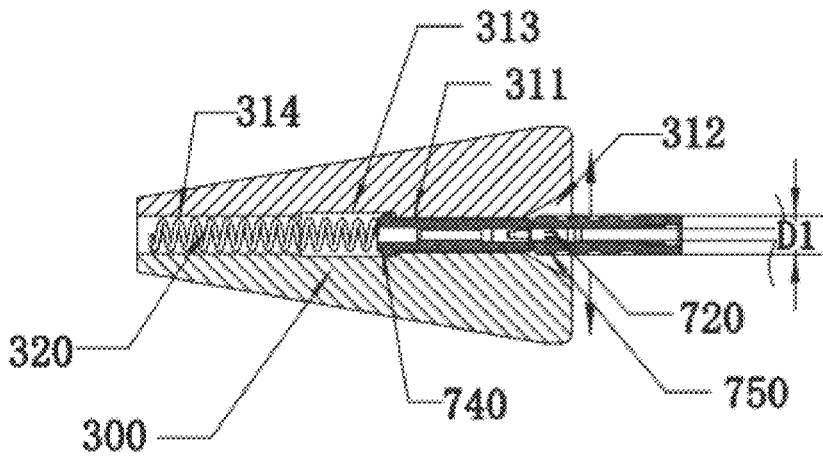
Figure 55:
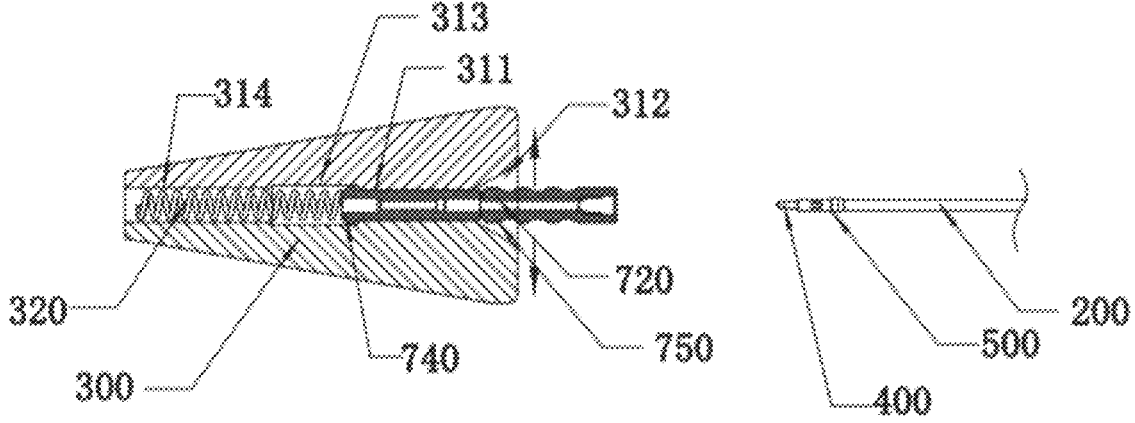
Figure 56:
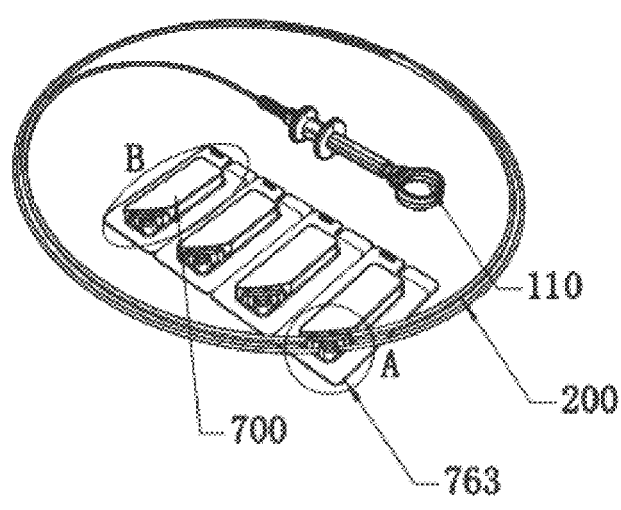
Figure 57:
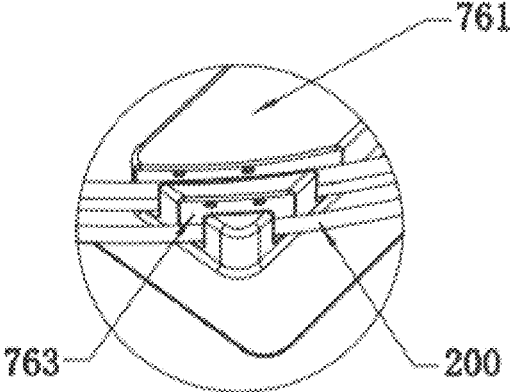
Figure 58:
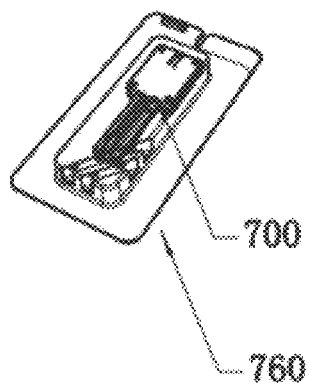
Figure 59:
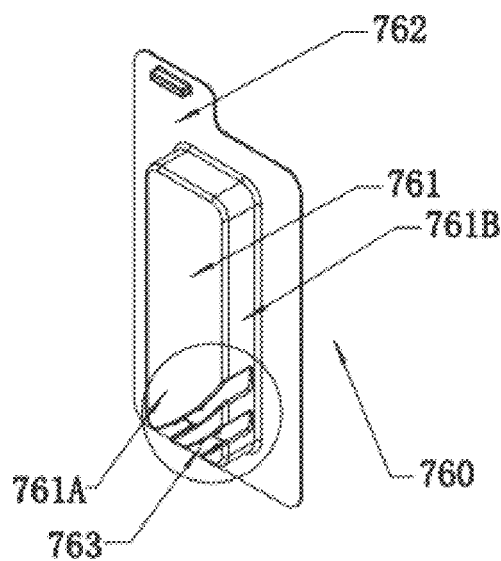
Figure 60:
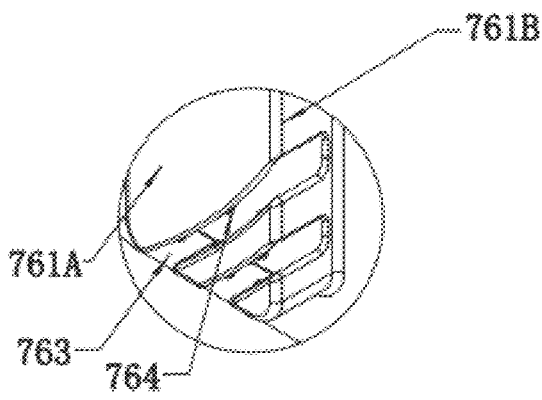
Figure 61:
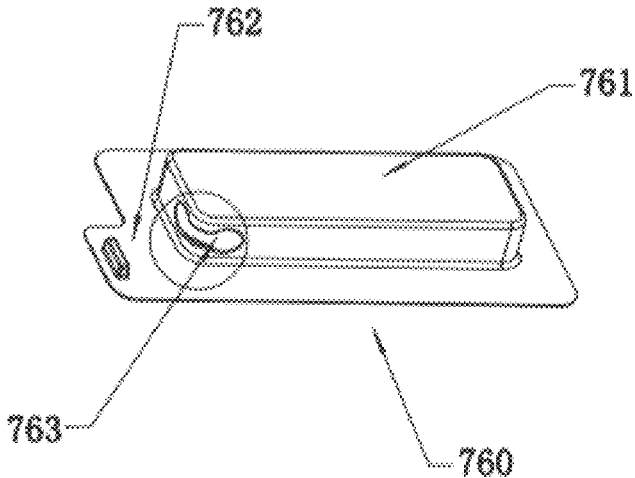
Figure 62:
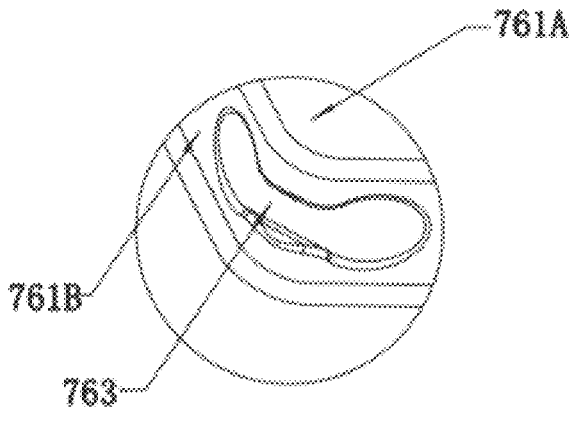
Figure 63:
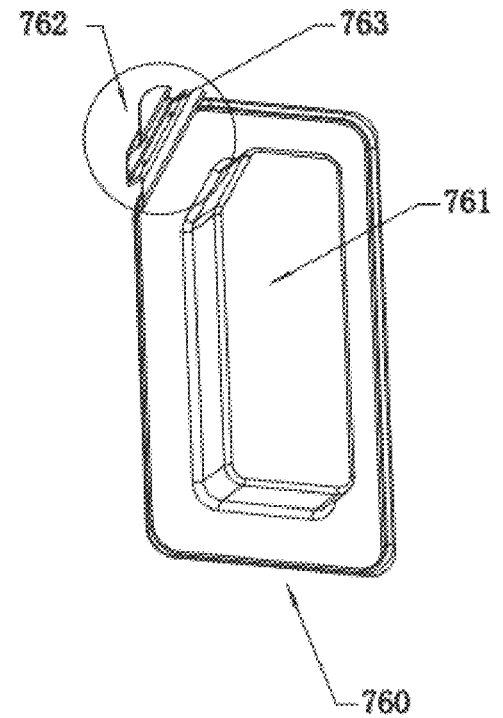
Figure 64:
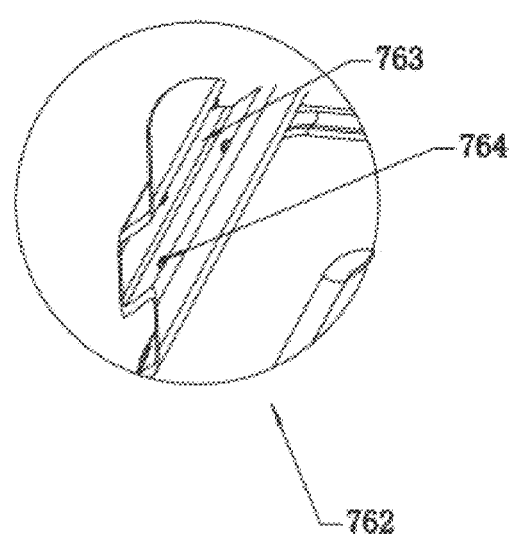
Figure 65:
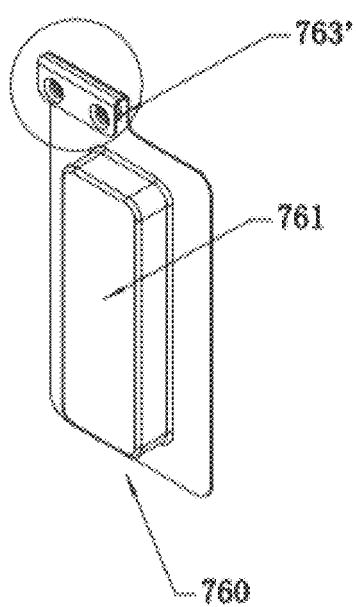
Figure 66:
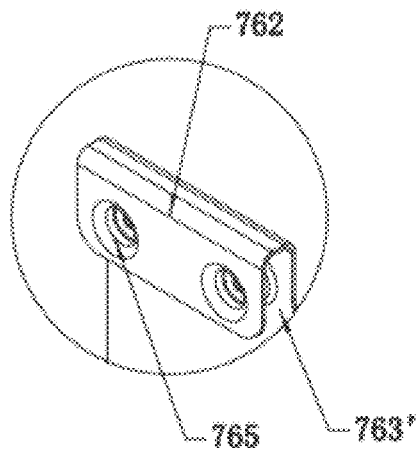
Figure 67:
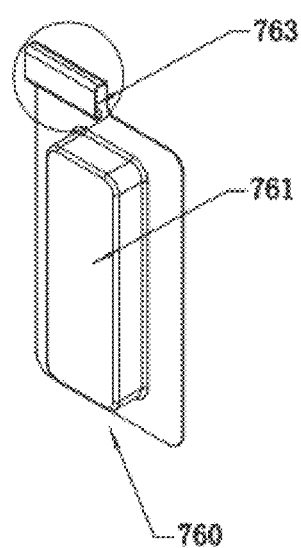
Figure 68:
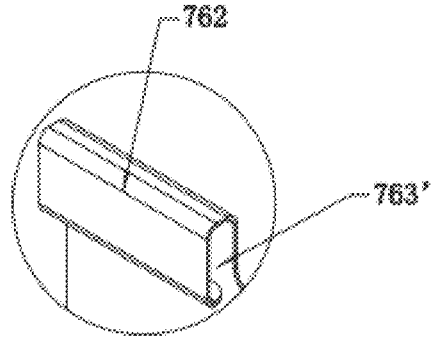
Figure 69:
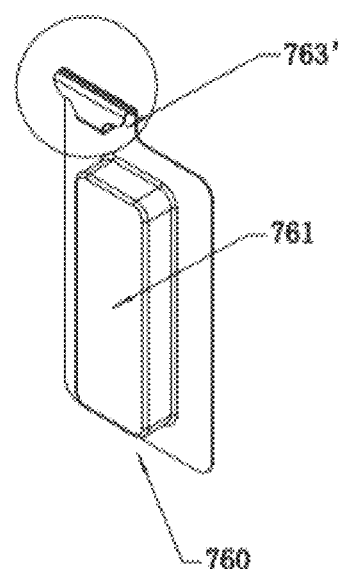
Figure 70:
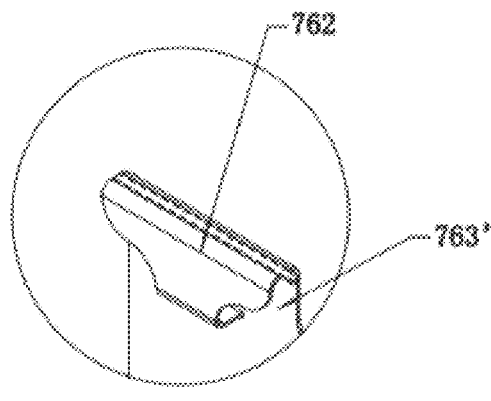
Figure 71:
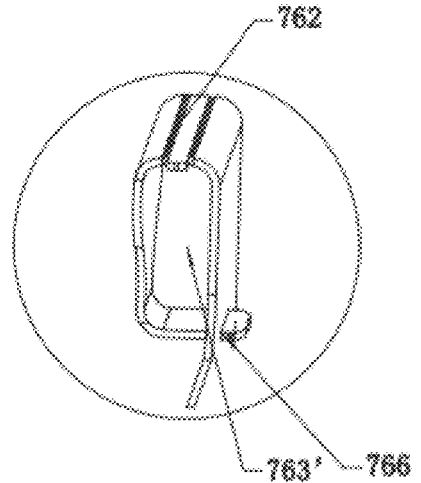
Figure 72:
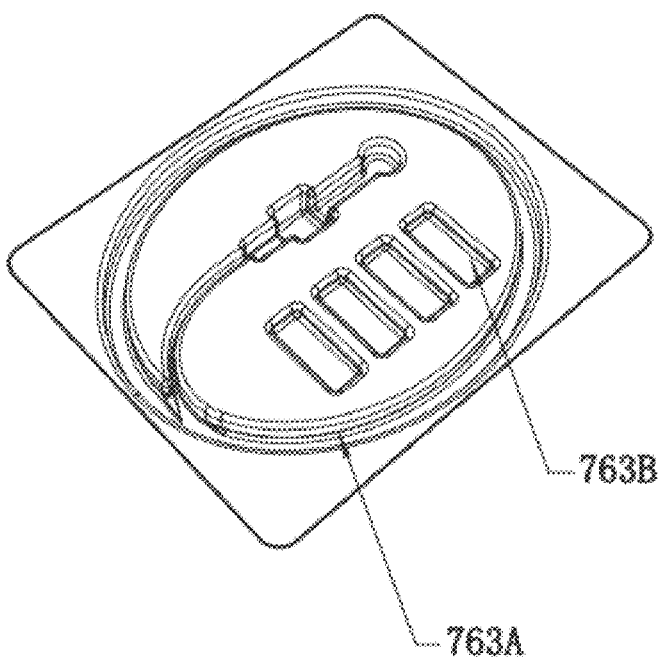
Figure 73:
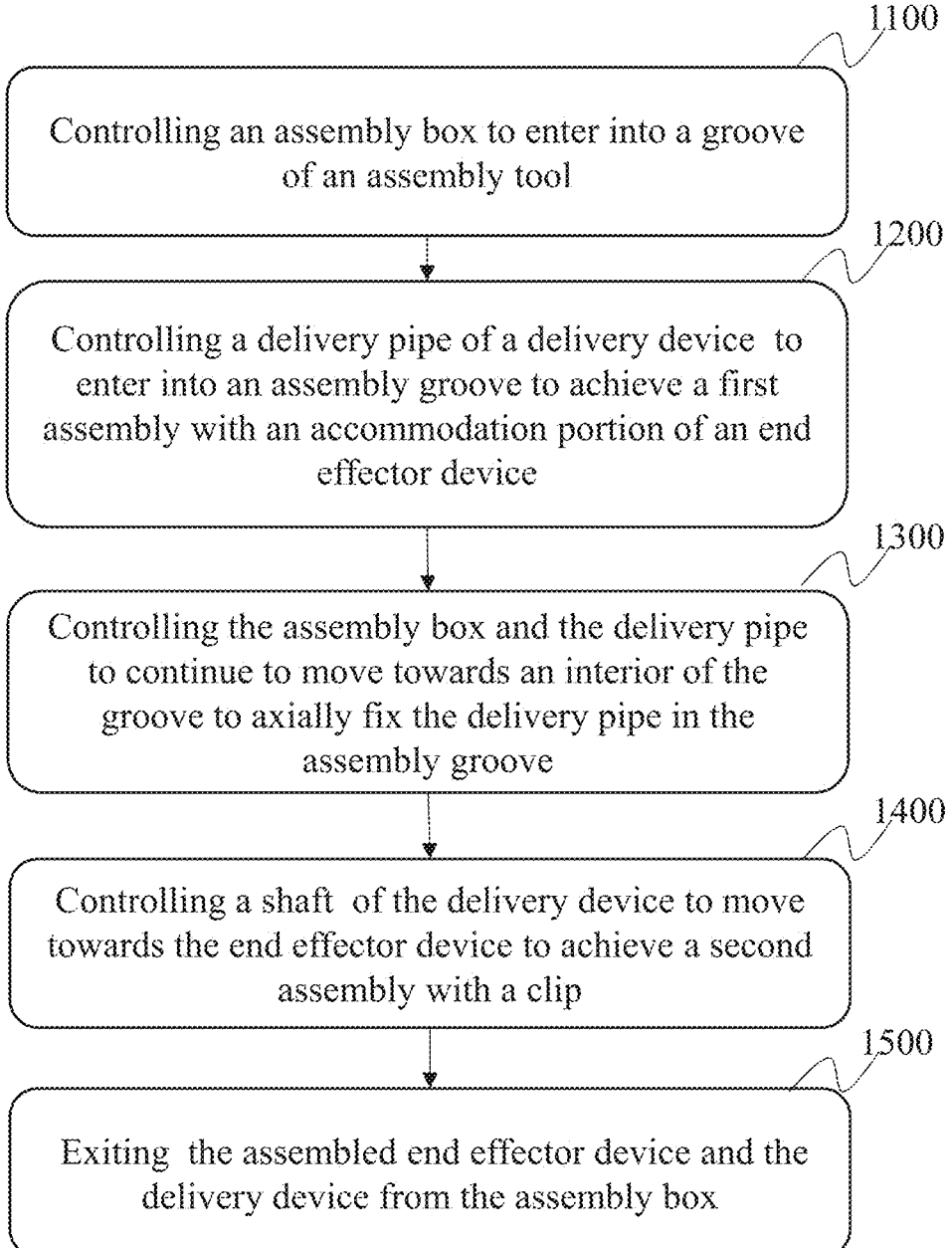
Figure 74:
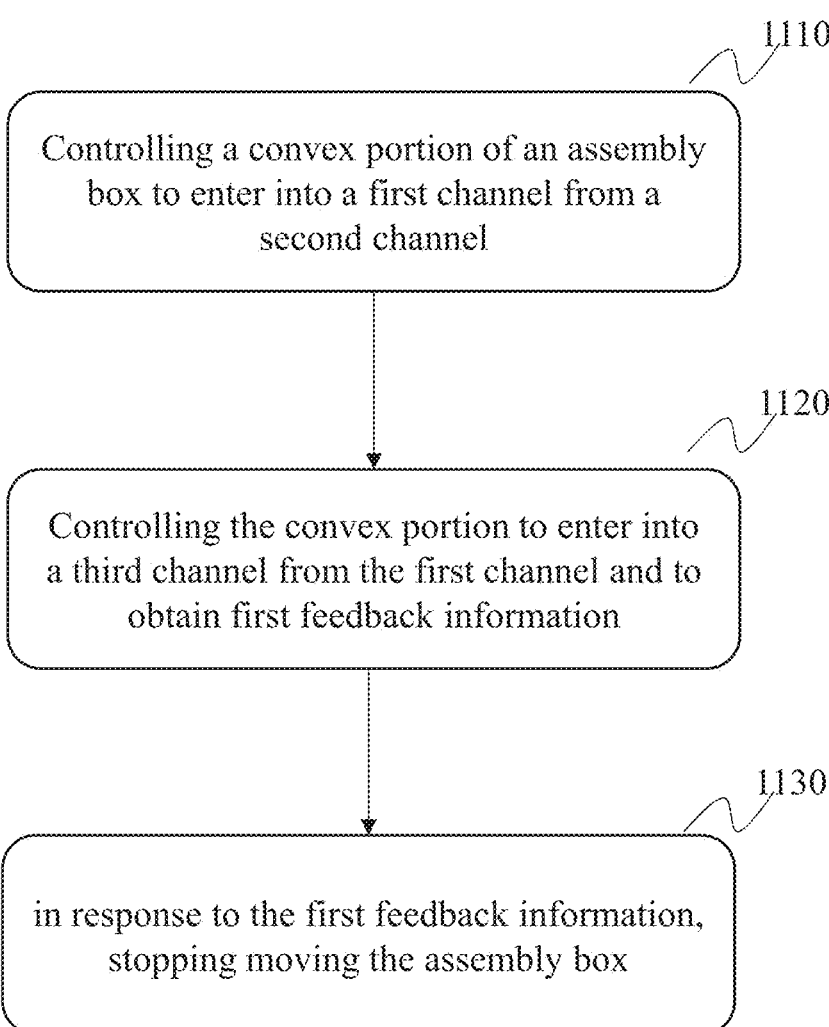

FIG. 3 is a schematic diagram illustrating a cross-sectional view of an end effector instrument according to some embodiments of the present disclosure;

FIG. 4 is a structure diagram of a clip according to some embodiments of the present disclosure;

FIG. 5 is a schematic diagram illustrating a cross-sectional view of a clip according to some embodiments of the present disclosure;

FIG. 6 is a schematic diagram illustrating a top view of an end effector device according to some embodiments of the present disclosure;

FIG. 7 is a structure diagram of an outer pipe according to some embodiments of the present disclosure;

FIG. 8 is a structure diagram of an inner pipe according to some embodiments of the present disclosure;

FIG. 9 is a structure diagram of a positioning convex according to some embodiments of the present disclosure;

FIG. 10 is a schematic diagram illustrating a cross-sectional view of a distal end of a delivery device according to some embodiments of the present disclosure;

FIG. 11 is a schematic diagram illustrating disassembly of an assembly box according to some embodiments of the present disclosure;

FIG. 12 is a diagram illustrating a structure of a first housing of an assembly box according to some embodiments of the present disclosure;

FIG. 13 is a structure diagram of an assembly box according to some embodiments of the present disclosure;

FIG. 14 is a first schematic diagram illustrating a cross-sectional view of a limiting slot according to some embodiments of the present disclosure;

FIG. 15 is a second schematic diagram illustrating a cross-sectional view of a limiting slot according to some embodiments of the present disclosure;

FIG. 16 is a first schematic diagram illustrating an assembly according to some embodiments of the present disclosure;

FIG. 17 is a second schematic diagram illustrating an assembly according to some embodiments of the present disclosure;

FIG. 18 is a third schematic diagram illustrating an assembly according to some embodiments of the present disclosure;

FIG. 19 is an enlarged view of a portion of FIG. 16;

FIG. 20 is a fourth schematic diagram illustrating an assembly according to some embodiments of the present disclosure;

FIG. 21 is an enlarged view of a portion of FIG. 18;

FIG. 22 is a fifth schematic diagram illustrating an assembly according to some embodiments of the present disclosure;

FIG. 23 is a sixth schematic diagram illustrating an assembly according to some embodiments of the present disclosure;

FIG. 24 is a first schematic diagram illustrating ligation according to some embodiments of the present disclosure;

FIG. 25 is a second schematic diagram illustrating ligation according to some embodiments of the present disclosure;

FIG. 26 is a third schematic diagram illustrating ligation according to some embodiments of the present disclosure;

FIG. 27 is a structure diagram of an end effector device according to some embodiments of the present disclosure;

FIG. 28 is a structure diagram illustrating an assembly box according to some embodiments of the present disclosure;

FIG. 29 is a front view of an assembly box according to some embodiments of the present disclosure;

FIG. 30 is a cross-sectional view of A-A in FIG. 29;

FIG. 31 is a cross-sectional view of B-B in FIG. 29;

FIG. 32 is a structure diagram illustrating a connection between a clip and an expanding portion according to some embodiments of the present disclosure;

FIG. 33 is an overall schematic diagram illustrating an assembly of an end effector device and a delivery device according to some embodiments of the present disclosure;

FIG. 34 is an overall schematic diagram illustrating an assembly tool according to some embodiments of the present disclosure;

FIG. 35 is an overall exploded view illustrating an assembly tool according to some embodiments of the present disclosure;

FIG. 36 is a front view of an assembly tool according to some embodiments of the present disclosure;

FIG. 37 is a cross-sectional view of A-A in FIG. 36;

FIG. 38 is an overall schematic diagram illustrating an assembly box according to some embodiments of the present disclosure;

FIG. 39 is an overall exploded view illustrating an assembly box according to some embodiments of the present disclosure;

FIG. 40 is a side view of an assembly box according to some embodiments of the present disclosure;

FIG. 41 is a cross-sectional view of B-B in FIG. 40;

FIG. 42 is an overall schematic diagram illustrating an assembly box and an end effector device according to some embodiments of the present disclosure;

FIG. 43 is a cross-sectional view of an assembly box and an end effector device according to some embodiments of the present disclosure;

FIG. 44 is a first schematic diagram illustrating an assembly processing according to some embodiments of the present disclosure;

FIG. 45 is a second schematic diagram illustrating an assembly processing according to some embodiments of the present disclosure;

FIG. 46 is a third schematic diagram illustrating an assembly processing according to some embodiments of the present disclosure;

FIG. 47 is an enlarged view of a portion F of FIG. 46;

FIG. 48 is a fourth schematic diagram illustrating an assembly processing according to some embodiments of the present disclosure;

FIG. 49 is a fifth schematic diagram illustrating an assembly processing according to some embodiments of the present disclosure;

FIG. 50 is a cross-sectional view of an assembly tool according to some embodiments of the present disclosure;

FIG. 51 is a first schematic diagram illustrating an assembly processing according to some embodiments of the present disclosure;

FIG. 52 is a second schematic diagram illustrating an assembly processing according to some embodiments of the present disclosure;

FIG. 53 is a third schematic diagram illustrating an assembly processing according to some embodiments of the present disclosure;

FIG. 54 is a fourth schematic diagram illustrating an assembly processing according to some embodiments of the present disclosure;

FIG. 55 is a fifth schematic diagram illustrating an assembly processing according to some embodiments of the present disclosure;

FIG. 56 is an overall schematic diagram illustrating an end effector instrument according to some embodiments of the present disclosure;

FIG. 57 is an enlarged view of portion A of FIG. 56;

FIG. 58 is an enlarged and perspective view illustrating B in FIG. 6;

FIG. 59 is an overall schematic diagram illustrating a housing according to some embodiments of the present disclosure;

FIG. 60 is an enlarged view of a portion of FIG. 59;

FIG. 61 is an overall schematic diagram illustrating a housing according to some embodiments of the present disclosure;

FIG. 62 is an enlarged view of a portion of FIG. 61;

FIG. 63 is an overall schematic diagram illustrating a housing according to some embodiments of the present disclosure;

FIG. 64 is an enlarged view of a portion of FIG. 63;

FIG. 65 is an overall schematic diagram illustrating a housing according to some embodiments of the present disclosure;

FIG. 66 is an enlarged view of a portion of FIG. 65;

FIG. 67 is an overall schematic diagram illustrating a housing according to some embodiments of the present disclosure;

FIG. 68 is an enlarged view of a portion of FIG. 67;

FIG. 69 is an overall schematic diagram illustrating a housing according to some embodiments of the present disclosure;

FIG. 70 is an enlarged view of a portion of FIG. 69;

FIG. 71 is a side view of FIG. 70;

FIG. 72 is a schematic diagram illustrating a limiting portion according to some embodiments of the present disclosure;

FIG. 73 is a flowchart illustrating an assembly and operation method of an end effector instrument according to some embodiments of the present disclosure; and FIG. 74 is a sub-flowchart illustrating an assembly and operation method of an end effector instrument according to some embodiments of the present disclosure.

DESCRIPTION OF REFERENCE NUMERALS
IN THE FIGURES 110, handle; 120, sliding portion;
200, sheath; 201, end cover; 202, limiting concave; 210, shaft; 211, connecting end; 212, large-diameter portion; 213, small-diameter portion;
300, assembly tool; 300A, first assembly housing; 300B, second assembly housing; 310, groove; 311, first channel; 312, second channel; 313, third channel; 314, fourth channel; 320, elastic component;
400, clip; 402, elastic ring; 410, first clip arm; 411, first bending portion; 412, first hole; 420, second clip arm; 421, second bending portion; 422, second hole; 432, connecting hole;
500, accommodation pipe; 501, outer pipe; 502, inner pipe; 503, guiding groove; 505, positioning convex; 506, fixed end; 507, free end; 508, retaining portion; 510, elastic piece; 511, locking portion; 513, blocking portion; 520, limiting convex; 550, expanding window;
601, connecting pin; 602, locking convex;
700, assembly box; 701, first-half box; 702, second-half box; 705, operating window; 710, effector device chamber; 720, assembly groove; 721, limiting slot; 722, groove slot; 730 assembly convex; 740, convex portion; 750, joint portion; 751, convex; 752, first portion; 753, second portion; 760, housing; 761, convex portion; 761A, surface of a convex portion; 761B, side surface of a convex portion; 762, non-convex portion; 763, limiting groove; 763', limiting channel; 763A, first limiting groove; 763B, second limiting groove; 764, convex point; 765, buckle; 766, groove; 800, human tissue;

900, expanding portion; 910, concave portion.

DETAILED DESCRIPTION

In order to more clearly illustrate the technical solutions of the embodiments of the present disclosure, the accompanying drawings that need to be used in the description of the embodiments may be briefly introduced below. Obviously, the drawings in the following description are only some examples or embodiments of the present disclosure for those of ordinary skill in the art, on the premise of no creative effort, the present disclosure can also be applied to other similar situations according to these drawings. Unless obvious from the locale or otherwise specified, the same reference numbers in the figures represent the same structure or operation.

It will be understood that the term "system," "device," "unit," and/or "module," and "block" used herein are one method to distinguish different components, elements, parts, sections or assembly of different levels. However, the terms may be displaced by another expression if they achieve the same purpose.

The terminology used herein is to describe particular example embodiments only and is not intended to be limiting. As used herein, the singular forms "a," "an," and "the," may be intended to include the plural forms as well, unless the context indicates otherwise. It will be further understood that the terms "comprise" and/or "include," when used in this specification, specify the presence of stated operations and elements, but do not preclude the presence or addition of one or more operations and elements in a method or a device.

A flowchart is used in the present disclosure to illustrate the operation performed by the system according to the embodiment of the present disclosure. It should be understood that the previous or subsequent operations are not necessarily performed accurately in order. Instead, the steps may be processed in reverse order or simultaneously. These steps may be added to or removed from another procedure.

The present disclosure may provide an end effector instrument. The end effector instrument may be configured to perform a surgical operation in minimally invasive surgery, such as surgical hemostasis, ligation, or the like. In some embodiments, the end effector instrument may include an end effector device and a delivery device. For example, the end effector device may be configured to clamp human tissue to achieve the function of the surgical hemostasis or the ligation. The delivery device may be configured to deliver the end effector device to a lesion in a patient. The end effector device may be maintained at the lesion to keep the lesion ligated.

In some embodiments, the end effector device and the delivery device may be an integrated design (also referred to as "an integral end effector instrument"). However, the integrated design of the end effector device and the delivery device may be all for one-time use, which may lead to a higher cost and more medical waste, and in turn be not economical or environmentally friendly.

In some embodiments, the end effector device and delivery device may be a disintegrated design (also referred to as "a disintegrated end effector instrument"). The end effector device may be for one-time use, and the delivery device may be reused, which may further save the cost, reduce the generation of medical waste, and be economical and environmentally friendly.

In some embodiments, in order to connect the end effector device to the delivery device during an assembly, the end effector device may include an accommodation pipe. The accommodation pipe may include a positioning groove configured to establish the connection to the delivery device. However, for a fine structure such as the accommodation pipe, it may be difficult to manufacture the accommodation pipe with the positioning groove.

Some embodiments of the present disclosure may provide an end effector instrument. An accommodation pipe of the end effector instrument may include an inner pipe and an outer pipe. The inner pipe may replace the role of a positioning groove to establish a connection to and release with a delivery device. The accommodation pipe may be divided into the inner pipe and the outer pipe. After fine structures are made on the inner pipe and the outer pipe, respectively, the outer pipe may fit snugly over the inner pipe, such that the inner pipe and the outer pipe may form the accommodation pipe, which may be convenient for production and manufacture, and particularly be beneficial to the manufacture of a small device for an endoscopic operation such as the end effector instrument.

In some embodiments, the assembly between the end effector device and the delivery device needs to be completed manually by an operator, and the assembly efficiency and success rate may be relatively low. In order to facilitate the assembly between the end effector device and the delivery device, the end effector instrument of some embodiments of the present disclosure may further provide an assembly device. The assembly device may include an assembly box and an assembly tool which may be configured to complete the assembly between the end effector device and the delivery device, improving the assembly efficiency.

Figure 1:
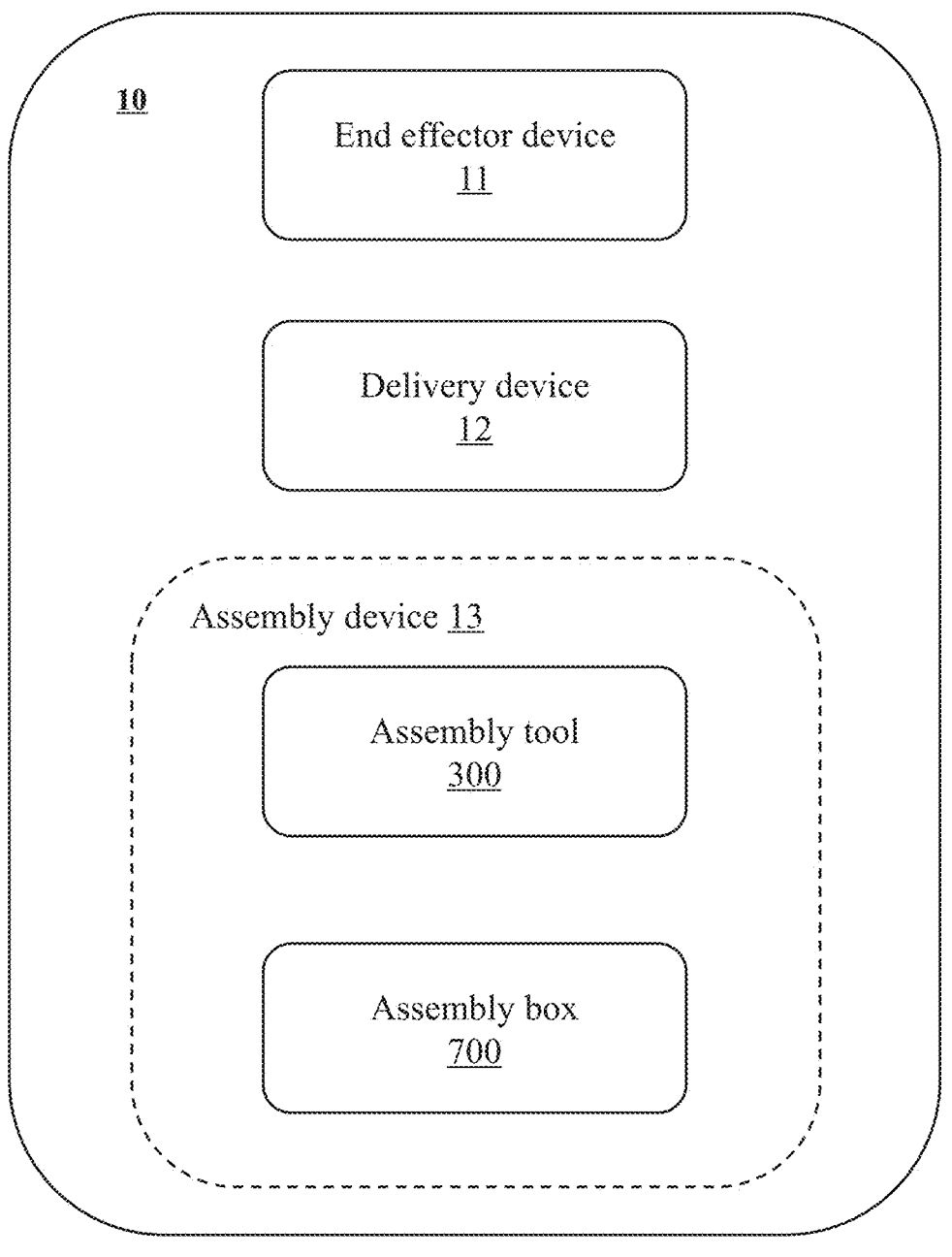
FIG. 1 is a block diagram illustrating an end effector instrument according to some embodiments of the present disclosure.
Figure 2:
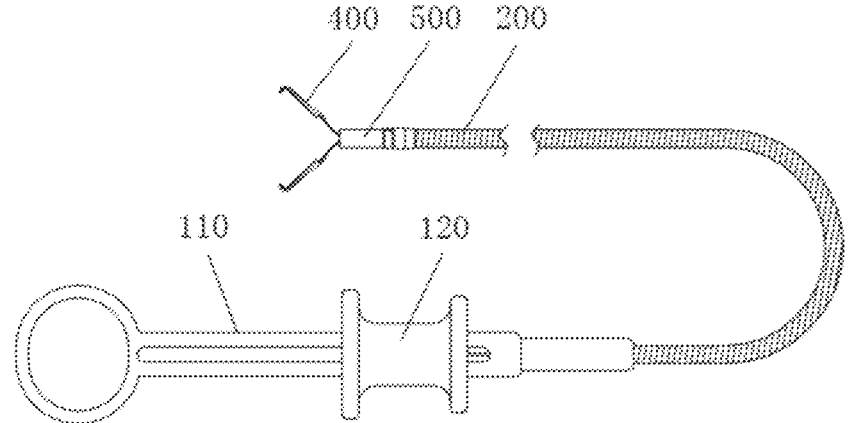
FIG. 2 is an overall structural diagram illustrating an end effector instrument according to some embodiments of the present disclosure.

FIG. 1 is a block diagram illustrating an end effector instrument according to some embodiments of the present disclosure.

As shown in FIG. 1, the end effector instrument 10 may include an end effector device 11 and a delivery device 12. The end effector device 11 may include an effector portion configured to perform a specified operation. The delivery device 12 may be connected to the end effector device 11. The delivery device 12 may be configured to deliver the end effector device 11 to a target area where the specified operation is to be performed. The delivery device 23 may include an operation portion. The operation portion may drive the effector portion to perform the specified operation. In some embodiments, the specified operation may be a medical operation in minimally invasive surgery, such as surgical hemostasis, ligation, etc. The effector portion of the end effector device 11 may be a medical instrument for performing a related operation, such as a hemostatic clip, a ligature clip, etc. In some embodiments, the target area may be an area within a target object where the specified operation needs to be performed. In some embodiments, the target object may include a biological object and a non-biological object. The biological object may include a human being, an animal, a plant, etc. The non-biological object may include an experimental model (e.g., an organ model, etc.). In some embodiments, the area within the target object where the specified operation needs to be performed may be a lesion area in the human being or the animal. In some embodiments, an operating portion of the delivery device 12 may include an operating handle. Specifically, an operator (e.g., a doctor) may operate the operating handle to control the end effector device 11 to perform an operation such as surgical hemostasis, ligation, etc.

In some embodiments, the end effector device 11 and the delivery device 12 may be integrally designed or fixedly connected for direct usage.

In some embodiments, the end effector device 11 and the delivery device 12 may be a disintegrated design, which may be assembled to complete the connection during usage. In some embodiments, the end effector device 11 may include an accommodation portion configured to partially accommodate the effector portion. The delivery device 12 may include a delivery pipe. The accommodation portion and the delivery pipe may be releasably connected to complete the assembly of the end effector device 11 and the delivery device 12. For example, the accommodation portion and the delivery pipe may be magnetically attracted together. Specifically, at least one of the accommodation portion and the delivery pipe may include an electromagnet or a coil, and another one may include a magnetic material or an electromagnet and a coil to power the accommodation portion and/or the delivery pipe respectively, which may make the accommodation portion and/or the delivery pipe magnetic. Therefore, the accommodation portion and the delivery pipe may be attracted together to establish the connection between the accommodation portion and the delivery pipe. When the accommodation portion and the delivery pipe are not powered on, the accommodation portion and/or the delivery pip may be not magnetic, the accommodation portion may be separated from the delivery pipe. As another example, the accommodation portion and the delivery pipe may be connected by a threaded connection. Specifically, the delivery pipe may have an internal thread. The accommodation portion may have an external thread corresponding to the internal thread. The delivery pipe may be screwed into the accommodation portion. The connection or separation between the end effector device 11 and the delivery device 12 may be realized by tightening or loosening the delivery pipe.

In some embodiments, the end effector instrument 10 may also include an assembly device 13. The assembly device 13 may be configured to assemble the end effector device 11 and the delivery device 12 to establish the connection between the end effector device 11 and the delivery device 12. In some embodiments, the assembly device 13 may include an assembly box configured to fix the end effector device 11 and the delivery device 12 when the end effector device 11 and the delivery device 12 are assembled. For example, the assembly box may include a joint portion configured to fix the end effector device 11 and the delivery device 12 after the joint portion is pressed. The operator may press the joint portion to fix the end effector device 11 and the delivery device 12. In some embodiments, the assembly device 13 may also include an assembly tool configured to facilitate the assembly box achieving the assembly and fixation of the end effector device 11 and the delivery device 12. For example, the assembly tool may include at least one groove. The assembly box may enter into or retract from the at least one groove to achieve the assembly of the delivery device 12 and the end effector device 11 in the assembly box to complete the assembly of the end effector instrument 10. When the assembly tool includes a plurality of grooves, a plurality of delivery devices 12 may be assembled with end effector devices 11 in a plurality of assembly boxes simultaneously to complete the assembly of a plurality of end effector instruments 10. It should be noted that the end effector instrument 10 may also omit the assembly device 13. The operator may assemble the end effector instrument 10 manually to establish the releasable connection between the end effector device 11 and the delivery device 12.

In some embodiments, for the separated end effector instrument 10, in order to realize the releasable connection between the end effector device 11 and the delivery device 12, a limiting convex (e.g., a limiting convex 520) may be positioned on the accommodation portion in the end effector device 11. A limiting concave may be positioned on a delivery pipe of the delivery device 12. The operator may push a shaft of the delivery device 12 to make a connecting end on the shaft abut the limiting convex. The limiting convex may be pressed to extend into the limiting concave on the delivery pipe. The connection between the limiting convex and the limiting concave may prevent a relative movement between the delivery pipe and the accommodation portion to complete the connection between the end effector device 11 and the delivery device 12. When the operator pulls the shaft, the connecting end of the shaft may be relieved from abutting the limiting convex. The limiting convex may retract from the limiting concave, thereby completing the separation of the end effector device 11 and the delivery device 12.

In some embodiments, the accommodation portion on the end effector device 11 may include a first connecting portion. The delivery pipe on the delivery device 12 may include a second connecting portion. The second connecting portion may connect the first connecting portion to complete the connection between the delivery device 12 and the end effector device 11. In some embodiments, the accommodation portion and the first connecting portion may be an integrated design. The delivery pipe and the second connecting portion may also be an integrated design. For example, the first connecting portion may be an external thread on the accommodation portion. The second connecting portion may be an internal thread on the delivery pipe corresponding to the external thread of the accommodation portion. The first connecting portion and the second connecting portion may be connected or separated through a thread connection manner. As another example, the first connecting portion may be a convex structure on the accommodation portion. The second connecting portion may be a concave structure on the delivery pipe corresponding to the convex structure. The convex structure and the concave structure may be formed on the accommodation portion and the delivery pipe by a stamping mold, respectively. In some embodiments, the accommodation portion and the first connecting portion may also be a disintegrated design. The delivery pipe and the second connecting portion may also be a disintegrated design. For example, the first connecting portion may be an elastic ring arranged inside the accommodation portion or fitting snugly over the accommodation portion. The elastic ring may have a concave structure or a convex structure, which may be used for identifying the position of the accommodation portion and also for connecting the second connecting portion (a convex structure or a concave structure). As another example, the first connecting portion may be a shaft sleeve. One end of the shaft sleeve may be configured to assemble the accommodation portion. Another end of the shaft sleeve may be configured to assemble the delivery pipe.

As shown in FIGS. 2-10, in some embodiments, the accommodation portion may include an accommodation pipe 500. The accommodation pipe 500 may include an inner pipe 502 and an outer pipe 501. At least a portion of the outer pipe 501 may fit snugly over the inner pipe 502. In some embodiments, the first connecting portion may be positioned on the inner pipe 502. In some embodiments, an inner diameter of the outer pipe 501 and an outer diameter of the inner pipe 502 may be substantially the same. The outer pipe 501 and the inner pipe 502 may be connected by way of an interference fit to form the accommodation portion. In some embodiments, the first connecting portion and the inner pipe 502 may be an integrated design. For example, the first connecting portion may be an internal thread positioned on the inner pipe 502. As another example, the first connecting portion may be a convex structure stamped on the inner pipe 502. In some embodiments, the inner pipe 502 and the outer pipe 501 may be fabricated from two pipe structures and then the inner pipe 502 and the outer pipe 501 may be assembled together, or the inner pipe 502 and the outer pipe 501 may be processed on a single pipe structure, respectively. In some embodiments, the material of the outer pipe 501 may include but be not limited to, stainless steel, titanium, tantalum, platinum, palladium, etc. In some embodiments, the material of the inner pipe 502 may include but be not limited to, stainless steel, titanium, tantalum, platinum, palladium, etc. In some embodiments, the material of the outer pipe 501 may be the same as that of the inner pipe 502. In some embodiments, the material of the outer pipe 501 may also be different from that of the inner pipe 502. For example, the outer pipe 501 may be made of titanium with a relatively high strength, and the inner pipe 502 may be made of stainless steel with a high toughness.

In some embodiments, the delivery pipe may include a sheath 200. In some embodiments, the second connecting portion may be positioned at a distal end of the sheath 200. It should be understood that the "proximal end" and "distal end" referred to in the present disclosure may represent an orientation. The orientation may refer to a length direction of the end effector instrument 10 (since the end effector device 11 may be transported, through the delivery device 12, to a human body for implementing surgical ligation, and the delivery device 12 may usually have a long line shape), or be along a direction that the end effector instrument 10 enters into the human body. A side close to the operator may be the "proximal end." A side extending into the human body to perform an operation may be the "distal end." The "proximal end" and the "distal end" should not be understood as only representing ends.

Referring to FIGS. 2-10, in some embodiments, the first connecting portion may include a limiting convex 520. The second connecting portion may include a limiting concave 202. The limiting convex 520 may enter into or retract from the limiting concave 202. The limiting concave 202 may correspond to the limiting convex 520 one by one. The limiting concave 202 and the limiting convex 520 may limit each other. In some embodiments, the limiting convex 520 may be integrally formed with the accommodation portion. For example, the limiting convex 520 may be a convex structure integrally formed on the accommodation portion. In some embodiments, the limiting convex 520 may also be a convex structure integrally formed on the inner pipe 502. In some embodiments, the limiting convex 520 may have a certain bending elasticity. When the delivery pipe is connected to the accommodation portion, an operation portion of the delivery device may press the limiting convex 520. The limiting convex 520 may be elastically deformed and extend into an interior of the limiting concave 202 of the delivery pipe. When a compressing force of the operation portion applied on the limiting convex 520 disappears, the limiting convex 520 may automatically rebound due to an elastic effect, so that the limiting convex 520 may retract from the limiting concave 202. For example, the operation portion may include a shaft connected to an operation handle, and the shaft may press the limiting convex 520. In some embodiments, the limiting convex 520 may also include other structures that may move towards the limiting concave 202, which may be non-limiting in the present disclosure. For example, the limiting convex 520 may include a convex structure rotatable axially along the inner pipe 502. As another example, the limiting convex 520 may include a telescopic structure retractable along a radial direction of the inner pipe 502. In some embodiments, the limiting concave 202 may be a blind hole, a through-hole, or a groove configured on a side wall of the delivery pipe. A step extending towards a central axis of the delivery pipe may be arranged on an inner wall of the delivery pipe. The limiting concave 202 may be formed between the step and the inner wall of the delivery pipe to limit the limiting concave 520. When the limiting convex 520 extends into the limiting concave 202, the delivery pipe and the accommodation portion may be connected, and the end effector device 11 may be connected to the delivery device 12. When the limiting convex 520 moves out of the limiting concave 202, the delivery pipe and the accommodation portion may be separated, and the end effector device 11 may be disconnected from the delivery device 12. In some embodiments, the first connecting portion may include the limiting concave 202 and the second connecting portion may include the limiting convex 520.

In some embodiments, the effector portion in the end effector device 11 may be configured to perform a specified operation during surgery, such as surgical hemostasis, ligation, etc. In some embodiments, the effector portion may include a clip 400, such as a hemostatic clip, ligation clip, or the like. In some embodiments, as shown in FIGS. 2-10, the end effector device 11 may include a clip 400 and an accommodation pipe 500. The accommodation pipe 500 may be configured with a channel. The inner pipe 502 and the outer pipe 501 may be configured with a channel, respectively. The channels of the inner pipe 502 and the outer pipe 501 may be connected to form the channel of the accommodation pipe 500. The clip 400 may be accommodated into the channel of the accommodation pipe 500 from a distal end. An outer wall of the inner pipe 502 may be configured with a limiting convex 520. The limiting convex 520 may be configured to cooperate with the limiting concave 202 to complete the connection and release between the sheath 200 and the inner pipe 502. The accommodation pipe 500 may be divided into the inner pipe 502 and the outer pipe 501. After fine structures are made on the inner pipe 502 and the outer pipe 501 respectively, the outer pipe 501 may fit snugly over the inner pipe 502, so that the inner pipe 502 and the outer pipe 501 may form the accommodation pipe 500, which may be convenient for production and manufacturing, and particularly be beneficial to the manufacture of a small device for an endoscopic operation such as the end effector instrument 10. The inner pipe 502 may be configured with the channel, and the outer pipe 501 may also be configured with the channel. As long as the inner pipe 502 and the outer pipe 501 are connected together, a depth of the inner pipe 502 inserted into the outer pipe 501 may be set arbitrarily according to actual needs. The channel of the inner pipe 502 may be connected to the channel of the outer pipe 501. The channel of the inner pipe 502 and the channel of the outer pipe 501 may constitute a movement channel of the clip 400 together. The clip 400 may enter into the movement channel from the distal end.

In some embodiments, the effector portion may include a lock connecting portion. The accommodation portion may include a locking portion 511 connecting to the lock connecting portion. When the locking portion 511 is connected to the lock connecting portion, the effector portion may be relatively fixed with respect to the accommodation portion to maintain an operation position or an operation state of the effector portion, for example, maintain the clip 400 in a clamping state. It should be noted that the lock connecting portion may be an independent structure on the effector portion and fixedly connected to other structures on the effector portion to complete the connection to the locking portion 511, thereby realizing the relative fixation between the effector portion and the accommodation portion. Alternatively, the lock connecting portion may also be a structure in the effector portion. In addition to realizing the relative fixation between the effector portion and the accommodation portion, the lock connecting portion may also play other roles in the effector portion. For example, when the effector portion is the clip 400, the lock connecting portion may also be configured to connect two clip arms of the clip 400.

As shown in FIGS. 3-5, in some embodiments, the lock connecting portion may be a structure in the effector portion. Specifically, the effector portion may include the clip 400. The clip 400 may include a first clip arm 410, a second clip arm 420, and a connecting pin 601. The first clip arm 410 and the second clip arm 420 may be pinned through the connecting pin 601. In some embodiments, one end of the connecting pin 601 may form the lock connecting portion. In some embodiments, both ends of the connecting pin 601 may form the lock connecting portion, respectively.

In some embodiments, the lock connecting portion may be a locking convex 602. The clip 400 may include a first clip arm 410, a second clip arm 420, and a connecting pin 601. The first clip arm 410 and the second clip arm 420 may be connected through the connecting pin 601. In this embodiment, both ends of the connecting pin 601 may form the locking convex 602, respectively, which may be non-limiting. In other embodiments, one end of the connecting pin 601 may form the locking convex 602. The connecting pin 601 may not only connect the first clip arm 410 and the second clip arm 420 but also lock the clip 400, and the structure may be simple.

In some embodiments, the effector portion may also include an elastic ring 402. The elastic ring 402 may fit snugly over the connecting pin 601 and be positioned between the first clip arm 410 and the second clip arm 420. In some embodiments, the elastic ring 402 may be a spring or any structure having elastic. In some embodiments, when the clip 400 may be clamped (or an opening and closing angle becoming smaller), the elastic ring 402 may be compressed by the first clip arm 410 and the second clip arm 420; when the clip 400 is released, the elastic ring 402 may provide an elastic force for the first clip arm 410 and the second clip arm 420, so that the first clip arm 410 and the second clip arm 420 may be away from each other at a position abutting the elastic ring (or the opening and closing angle becoming larger). A direction of the elastic force of the elastic ring 402 may refer to a direction in which the first clip arm 410 and the second clip arm 420 are away from each other at the position abutting the elastic ring 402. Preferably, the elastic ring 402 may be a helicoidal spring. The helicoidal spring may fit snugly over the connecting pin 601 through its helicoidal circle. In some embodiments, the effector portion may omit the elastic ring, and the first clip arm 410 and the second clip arm 420 may be away from each other by their elastic force.

In some embodiments, the locking portion 511 may include an elastic piece 510. One end of the elastic piece 510 may be fixedly connected to the accommodation portion, and another end of the elastic piece 510 may extend into an interior of the accommodation portion. In some embodiments, the accommodation pipe 500 may be an integrated pipe body. In some embodiments, the elastic piece 510 may be arranged on the accommodation pipe 500. In some embodiments, one end of the elastic piece 510 may be fixedly connected to a side wall of the accommodation pipe 500, and another end of the elastic piece 510 may extend into the channel of the accommodation portion. It should be understood that the channel of the accommodation portion may be an internal space of the accommodation pipe 500. In some embodiments, the locking portion 511 may be integrally formed with the accommodation portion. For example, the elastic piece 510 may be formed on the side wall of the accommodation pipe 500 by laser cut, which may require that the material of the outer pipe 501 has a certain elasticity. In some embodiments, the locking portion 511 and the accommodation portion may be a disintegrated design. For example, a groove hole capable of accommodating the elastic piece 510 may be cut on the side wall of the accommodation pipe 500, and then one end of the elastic piece 510 may be fixed at an edge of the groove hole in a gluing manner, a welding manner, or a fastener fixation manner, while another end of the elastic piece 510 may be in a free state, so that the elastic piece 510 may extend into the channel of the accommodation portion. In some embodiments, an end of the elastic piece 510 fixedly connected to the accommodation portion may be a proximal end, i.e., an end close to the operator.

In some embodiments, the accommodation pipe 500 may include the outer pipe 501 and the inner pipe 502. The outer pipe 501 may be configured with the elastic piece 510. The inner pipe 502 and the outer pipe 501 may be configured with a channel, respectively. The channels of the inner pipe 502 and the outer pipe 501 may be connected to form a channel of the accommodation pipe 500. At least a portion of the elastic piece 510 may extend into the channel of the accommodation pipe 500 and form the locking portion 511. In some embodiments, when both ends of the connecting pin 601 form the locking convex 602, there are two elastic pieces 510 corresponding to two ends of the connecting pin 601, respectively. In this embodiment, the clip 400 may be configured with a locking convex 602, i.e., both ends of the connecting pin 601 may form the locking convex 602, which may respectively correspond to the locking portion 511 on the two elastic pieces 510. The locking convex 602 may be configured to lock a positional relationship between the clip 400 and the accommodation pipe 500 to prevent the clip 400 from opening by moving from the distal end of the accommodation pipe 500.

In some embodiments, the clip 400 may enter into the channel of the accommodation pipe 500 from the distal end of the accommodation pipe 500. When the locking convex 602 is positioned at a distal end of the locking portion 511, the clip 400 may move towards the distal end of the accommodation pipe 500. When the clip 400 is moved from the distal end to the proximal end, the clip 400 may be gradually closed under the compressing of the accommodation pipe 500. When the clip 400 moves to the locking portion 511 or near the locking portion 511, the locking convex 602 may press the locking portion 511 outward. The elastic piece 510 may deform to make the locking portion 511 bulge to make room for the locking convex 602, so that the locking convex 602 may move to a proximal end of the locking portion 511 through the locking portion 511. At this time, the clip 400 may be closed and the locking portion 511 may be positioned at a distal end of the locking convex 602. When the locking convex 602 passes over the locking portion 511, the locking portion 511 may rebound. The locking portion 511 may extend into the accommodation pipe 500. The locking portion 511 may be positioned on a path of the locking convex 602 moving to the distal end to prevent the locking convex 602 from moving to the distal end. In this way, the clip 400 may be locked by the locking convex 602 and the locking portion 511. The clip 400 may be unable to move to the distal end of the accommodation pipe 500, avoiding reopening after the clip 400 is closed. The structure of the elastic piece 510 and the locking portion 511 may be simple. The rebounding of the elastic piece 510 may refer to that: during the compressing of the locking convex 602, the locking portion 511 may be bulged; after the locking convex 602 passes over the locking portion 511, the locking portion 511 may rebound to block the locking portion 511. It may not mean that the elastic piece 510 must be made of an elastic material. The elastic piece 510 may be made of any material. Preferably, the material of the elastic piece 510 may be the same as that of the accommodation pipe 500. The elastic piece 510 may be a part of the side wall of the accommodation pipe 500 after cutting. One end of the elastic piece 510 may be connected to the side wall of the accommodation pipe 500, and another end of the elastic piece 510 may extend into the channel of the accommodation pipe 500.

In some embodiments, in order to facilitate the movement of the effector portion relative to the accommodation portion, the accommodation portion may be configured with a guiding groove 503 along an axial direction. In some embodiments, the guiding groove 503 may be opened on the inner pipe 502 of the accommodation portion. For example, the guiding groove 503 may be formed on a side wall of the inner pipe 502 by laser cut. In some embodiments, the lock connecting portion may slide in the guiding groove 503. The locking portion 511 may extend into the guiding groove 503. The guiding groove 503 may guide the lock connecting portion to move to a position where the locking portion 511 is positioned to complete the connection between the locking portion 511 and the lock connecting portion.

In some embodiments, an end of the guiding groove 503 away from the effector portion may be configured with a positioning convex 505. A distance between the positioning convex 505 and the effector portion may be greater than a distance between the locking portion 511 and the effector portion, i.e., the locking portion 511 may be positioned between the positioning convex 505 and the effector portion. It should be understood that a distance between the positioning convex 505 and the effector portion and a distance between the locking portion 511 and the effector portion may be distances of the positioning convex 505 and the locking portion 511 to a nearest end of the effector portion. In some embodiments, when the lock connecting portion moves to a proximal end along the guiding groove 503, the locking portion 511 may be connected to the lock connecting portion to prevent the lock connecting portion from not moving to the distal end, and the positioning convex 505 may prevent the further movement of the lock connecting portion to the proximal end, i.e., a position of the effector portion may be constrained by the locking portion 511 and the positioning convex 505 at the same time, and may not move to the proximal end or the distal end to maintain at a usage state (e.g., a closed state) when the effector portion performs the specified operation, and maintain the stability of the effector portion in the usage state.

In some embodiments, the inner pipe 502 may be configured with the guiding groove 503. The locking convex 602 may slide in the guiding groove 503. The guiding groove 503 may guide the locking convex 602 to move to the position of the locking portion 511, facilitating the locking. Preferably, the locking portion 511 may extend into the guiding groove 503. The guiding groove 503 may be configured with a positioning convex 505. The positioning convex 505 may be positioned at the proximal end of the locking portion 511. When the locking portion 511 prevents the locking convex 602 from moving to the distal end, the locking convex 602 may be positioned between the positioning convex 505 and the locking portion 511. In some embodiments, as shown in FIG. 3, a height of the locking convex 602 may be H2, a height of the locking portion may be H1, and a height of the positioning convex may be H3. When the locking convex 602 is positioned between the positioning convex 505 and the locking portion 511, H2>H1, and H2>H3. Thus, the locking portion 511 may restrict the locking convex 602 from moving to the distal end, and the positioning convex 505 may restrict the locking convex 602 from moving to the proximal end, so that the position of the clip 400 may be constrained by the locking portion 511 and the positioning convex 505 at the same time, and may not move to the proximal or the distal end, so that the clip 400 may be in the closed state, and the closed state of the clip 400 may be stable.

In some embodiments, the accommodation portion may omit the inner pipe 502 and the outer pipe 501 but may be arranged as an accommodation pipe structure with an internal channel. At this time, the locking portion 511 may be arranged on the accommodation pipe, and the guiding groove 503 may be arranged on an inner wall of the accommodation pipe. For example, the guiding groove 503 may be a groove opened along an internal thickness direction on the inner wall of the accommodation pipe. The depth of the groove may be smaller than the thickness of the inner wall of the accommodation pipe. The locking portion 511 may be an elastic piece 510. A free end 507 of the elastic piece 510 may extend into an interior of the guiding groove 503.

In some embodiments, the guiding groove 503 may also include a retaining portion 508. In some embodiments, as shown in FIG. 9, the retaining portion 508 may be arranged on the positioning convex 505. The retaining portion 508 may include a fixed end 506 and a free end 507. The fixed end 506 may be fixedly connected to the positioning convex 505. The free end 507 may face an interior of the guiding groove 503. In some embodiments, the free end 507 may include an elastic structure for providing an elastic force that hinders the movement of the lock connecting portion. In some embodiments, the lock connecting portion (e.g., the locking convex 602) may move towards the proximal end in the guiding groove 503 and abut the free end 507. The free end 507 may provide a feedback force that may prevent the lock connecting portion from moving towards the proximal end. In some embodiments, the feedback force may be configured to provide an operator with reminder feedback information. The reminder feedback information may be configured to signify the operator if the lock connecting portion continues to move towards the proximal end, the lock connecting portion may be locked by the locking portion 511. In some embodiments, the fixed end 506 of the retaining portion 508 may be fixed to the positioning convex 505 by gluing, welding, a fastener, etc. In some embodiments, the retaining portion 508 may be integrally formed with the positioning convex 505. For example, the retaining portion 508 may be a spring fixedly connected to the positioning convex 505. As another example, the retaining portion 508 may be a convex structure of the positioning convex 505 facing an interior of the guiding groove 503.

In some embodiments, the delivery device 12 may include a handle 110, a sliding portion 120, the sheath 200, and a shaft 210. The shaft 210 may be arranged in a channel of the sheath 200. A proximal end of the shaft 210 may be connected to the sliding portion 120. A proximal end of the sheath 200 may be connected to the handle 110. The sliding portion 120 may slide on the handle 110 to drive the shaft 210 to move towards the proximal end or the distal end. In some embodiments, the handle 110, the sliding portion 120, and the shaft 210 may constitute an operation portion of the delivery device 12. In some embodiments, the sheath 200 and an internal space of the sheath 200 may form the delivery pipe of the delivery device.

In some embodiments, a releasable connection between the end effector device 11 and the delivery device 12 may be performed by the operation portion. In some embodiments, one end of the shaft 210 may extend into or retract from the accommodation portion, and another end of the shaft 210 may be connected to the sliding portion 120. An end on the shaft 210 for connecting the sliding portion 120 may become a proximal end of the shaft 210, and another end without connecting the sliding portion 120 may become the distal end of the shaft 210. In some embodiments, the distal end of the shaft 210 may include a connecting end 211. When the distal end of the shaft 210 extends into the accommodation portion, due to the elasticity of the limiting convex 520, the limiting convex 520 may be subjected to a compressing force applied by the connecting end 211 towards the limiting concave 202, so that the limiting convex 520 may be compressed by the connecting end 211 and extend into the limiting concave 202. An outer diameter of the connecting end 211 may be greater than an inner diameter of the limiting convex 520. The inner diameter of the limiting convex 520 may be an inner diameter of the inner pipe 502 or an inner diameter of the elastic ring. When the distal end of the shaft 210 retracts from the accommodation portion, the limiting convex 520 may be relieved from being compressed by the connecting end 211, such that the limiting convex 520 may be elastically restored, and then retract from the limiting concave 202. In some embodiments, the distal end of the shaft 210 may omit the connecting end 211. The outer diameter of the shaft 210 may be greater than the inner diameter of the limiting convex 520. After the shaft 210 extends into the limiting convex 520, the limiting convex 520 may be directly compressed to extend the limiting convex 520 into the limiting concave 202.

In some embodiments, the connecting end 211 may be integrally formed with the shaft 210. For example, the connecting end 211 may be machined at one end of the shaft 210. In some embodiments, the connecting end 211 may be detachably connected to the shaft 210. For example, a threaded hole may be positioned along one axial direction of the connecting end 211 or the shaft 210, and an external thread corresponding to the threaded hole may be positioned along another axial direction of the connecting end 211 or the shaft 210. The connecting end 211 and the shaft 210 may be detachably connected through a thread. As another example, the connecting end 211 and the shaft 210 may be detachably connected by a magnetic connection.

In some embodiments, the distal end of the shaft 210 may be configured with the connecting end 211. The distal end of the sheath 200 may be configured with an end cover 201. An inner wall of the end cover 201 may be configured with the limiting concave 202. The limiting concave 202 may be configured to cooperate with the limiting convex 520 to complete the connection and release of the sheath 200 and the inner pipe 502. When the sheath 200 may fit snugly over the limiting convex 520. The connecting end 211 may extend into or retract from the inner pipe 502. When the connecting end 211 extends into the inner pipe 502, the limiting convex 520 may be compressed by the connecting end 211 and extend into the limiting concave 202. The inner pipe 502 and the sheath 200 may be connected to push the sheath 200 to the distal end. The accommodation pipe 500 may also be pushed to the distal end. If the sheath 200 pulls to the proximal end, the accommodation pipe 500 may also be brought to the proximal end. When the connecting end 211 retracts from the inner pipe 502, the limiting convex 520 may retract from the limiting concave 202. A connection between the accommodation pipe 500 and the sheath 200 may be released. For example, after the clip 400 is ligated, the sheath 200 may be taken out separately and the clip 400 may be left at the lesion to remain ligated.

As shown in FIGS. 3-5, in some embodiments, a proximal end of the first clip arm 410 may be configured with a first bending portion 411 bending towards the second clip arm 420. The first bending portion 411 may be configured with a first hole 412. A proximal end of the second clip arm 420 may be configured with a second bending portion 421 bending towards the first clip arm 410. The second bending portion 421 may be configured with a second hole 422. In some embodiments, a bending angle between the first bending portion 411 and the first clip arm 410 may be 85°~95°. A bending angle between the second bending portion 421 and the second clip arm 420 may be 85°~95°. In some embodiments, a sum of the bending angles of the first bending portion 411 and the second bending portion 421 may be 180°. In some embodiments, the first hole 412 and the second hole 422 may at least partially overlap and communicate, and the overlapping and communicating part of the first hole 412 and the second hole 422 may form a connecting hole 432. The "at least partially overlapping" may include a partially overlapping communication and a completely overlapping communication. The partially overlapping communication may refer to that the first hole 412 and the second hole 422 are slightly staggered without complete overlapping. The completely overlapping communication may refer to that the first hole 412 completely overlaps the range of the second hole 422, or the second hole 422 completely overlaps the range of the first hole 412. The overlapping may be understood as two holes connected to each other. After the first hole 412 and the second hole 422 are connected, the connection part between the first hole 412 and the second hole 422 may form the connecting hole 432.

In some embodiments, in order to realize the connection between the operation portion and the effector portion, the shaft 210 may fit snugly over the connecting hole 432. Specifically, the shaft 210 may include a large-diameter portion 212 and a small-diameter portion 213. A diameter of the large-diameter portion 212 of the shaft 210 may be larger than an inner diameter of the connecting hole 432. A diameter of the small-diameter portion 213 may be smaller than the inner diameter of the connecting hole 432. In some embodiments, the small-diameter portion 213 may be fixedly connected to the distal end of the shaft 210, and the large-diameter portion 212 may be fixedly connected to the small-diameter portion 213. In some embodiments, the distal end of the shaft 210 may be fixedly connected to the connecting end 211. A distal end of the connecting end 211 may be fixedly connected to the small-diameter portion 213. A distal end of the small-diameter portion 213 may be fixedly connected to the large-diameter portion 212. In some embodiments, the large-diameter portion 212 and the small-diameter portion 213 of the shaft 210 may be integrally formed, or the large-diameter portion 212 of the shaft 210 may be fixedly connected to the small-diameter portion 213 by gluing, a fastener, welding, etc.

In some embodiments, when the operator pushes the shaft 210 towards the distal end to the effector portion, after the large-diameter portion 212 passes through the first hole 412 and the second hole 422, the connection between the effector portion and the operation portion may be completed, so that the effector portion may be controlled by the operation portion to perform the specified operation, such as ligation operation, etc.

Specifically, when the large-diameter portion 212 of the shaft 210 enters into the connecting hole 432, since the diameter of the large-diameter portion 212 may be larger than the inner diameter of the connecting hole 432, the large-diameter portion 212 may press the connecting hole 432 to increase the inner diameter of the connecting hole 432. At this time, the elastic ring may be pressed and have the elastic force to make the large-diameter portion 212 traverse. When the large-diameter portion 212 passes through, the first clip arm 410 and the second clip arm 420 may be away from each other through the elastic force of the elastic ring, so that the first hole 412 and the second hole 422 may be staggered with each other, thereby reducing the inner diameter of the connecting hole 432, so that the large-diameter portion 212 may not move to the proximal end through the connecting hole 432 without an external force.

In some embodiments, as shown in FIG. 21, the distal end of the shaft 210 may be configured with the large-diameter portion 212 and the small-diameter portion 213. The large-diameter portion 212 may be positioned at the distal end of the small-diameter portion 213. The small-diameter portion 213 may be positioned at the distal end of the connecting end 211. The diameter of the large-diameter portion 212 may be larger than the diameter of the small-diameter portion 213. The distal end of the connecting end 211 may be configured with the large-diameter portion 212 and the small-diameter portion 213. The small-diameter portion 213 may be positioned between the large-diameter portion 212 and the connecting end 211. The diameter of the large-diameter portion 212 may be larger than the diameter of the small-diameter portion 213. The diameter of the small-diameter portion 213 may be the same as or different from the diameter of the connecting end 211. Alternatively, the small-diameter portion 213 may be a part of the distal end of the connecting end 211. The connecting portion between the first hole 412 and the second hole 422 of the clip 400 may form the connecting hole 432. The large-diameter portion 212 may need to traverse the first hole 412 and the second hole 422 to complete the connection. The elastic force of the elastic ring 402 may tend to keep the first clip arm 410 and the second clip arm 420 away from each other, so that the first hole 412 and the second hole 422 may tend to be staggered with each other and the diameter of the connecting hole 432 may tend to be reduced.

In some embodiments, when the large-diameter portion 212 passes through the connecting hole 432 to complete the connection between the effector portion and the operation portion, the effector portion may move in the accommodation portion under the operation of the operation portion. For example, the operator may push the sliding portion 120 to the distal end to move the clip 400 to the distal end under a drive of the shaft 210. The operator may also push the sliding portion 120 towards the proximal end to move the clip 400 towards the proximal end under a drive by the shaft 210.

As shown in FIG. 21, in some embodiments, a distal end of the outer pipe 501 may be configured with a blocking portion 513. The blocking portion 513 may extend into the channel of the accommodation pipe 500. The blocking portion 513 may be positioned at a distal end of the connecting pin 601. Due to the blocking of the blocking portion 513, the clip 400 may be prevented from retracting from the distal end of the accommodation pipe 500.

In some embodiments, the assembly of the end effector device 11 and the delivery device 12 may be performed manually by the operator. In some embodiments, in order to replace the manual operation of the operator and improve the assembly efficiency and accuracy of the end effector device 11 and the delivery device 12, the end effector instrument 10 may also include an assembly device 13 configured to assembly the end effector device 11 and the delivery device 12 to complete the connection between the end effector device 11 and the delivery device 12. In some embodiments, the assembly device 13 may also be referred to as an assembly system.

In some embodiments, the assembly device 13 may include an assembly box 700 configured to fix the end effector device 11 and the delivery device 12 when the end effector device 11 and the delivery device 12 are assembled. For example, the assembly box 700 may include a chamber for accommodating the end effector device 11 and the delivery device 112. During the assembly, the assembly box 700 may fix positions of the end effector device 11 and the delivery device 12 through the chamber so that the end effector device 11 and the delivery device 12 may not move relative to each other.

In some embodiments, as shown in FIGS. 11-13, the embodiment may also include the assembly box 700 configured to assemble the end effector device 11 with the delivery device 12. The assembly box 700 may include the connection between the sheath 200 and the accommodation pipe 500 and the connection between the shaft 210 and the clip 400.

The assembly box 700 may include a housing. The housing may be configured with an effector device chamber 710 and an assembly groove 720 that are axially communicated. In this embodiment, the housing may include a first-half box 701 and a second-half box 702. The first-half box 701 and the second-half box 702 may form the effector device chamber 710 and the assembly groove 720. The assembly groove 720 may be configured to place the delivery device 12. The effector device chamber 710 may be configured to place the end effector device 11. Preferably, the end effector device 11 may be sterilized and sealed in the assembly box 700 when the end effector device 11 leaves the factory to ensure the cleanliness of the end effector device 11.

In some embodiments, as shown in FIG. 13, the assembly box 700 may be configured with the assembly groove 720. The assembly groove 720 may be configured with a groove slot 722. The sheath 200 may be put into the assembly groove 720 through the groove slot 722, which may be convenient for operation. Preferably, the groove slot 722 of the assembly groove 720 may be positioned on a plane where the clip 400 opens. A proximal end of the assembly groove 720 may be configured with a limiting slot 721. The limiting slot 721 may be connected to the groove slot 722. A width of the limiting slot 721 may be smaller than a width of the assembly groove 720. The sheath 200 may be clamped into the limiting slot 721. The width of the limiting slot 721 may be by way of interference fit with the sheath 200. When there is no external force, the sheath 200 may be not easy to retract from the limiting slot 721, which may be convenient for positioning the sheath 200 to complete the assembly more easily.

The effector device chamber 710 may be configured with an assembly convex 730. The assembly convex 730 may be configured to abut the accommodation pipe 500. During the assembly, the accommodation pipe 500 may abut the assembly convex 730. The sheath 200 may be put into the assembly groove 720 to push the sheath 200 to move from the proximal end to the distal end, so that the sheath 200 may fit snugly over the inner pipe 502. At this time, by pushing the shaft 210 from the proximal end to the distal end, the connecting end 211 of the shaft 210 may be inserted into the channel of the inner pipe 502 to connect the inner pipe 502 to the sheath 200. By continuing to move the shaft 210 to the distal end, the shaft 210 may be inserted into the connecting hole 432 to connect the shaft 210 to the clip 400. In this process, since the assembly convex 730 may abut the accommodation pipe 500, when the sheath 200 or the shaft 210 moves from the proximal end to the distal end, the movement of the accommodation pipe 500 to the distal end may be bulged, which may be convenient for assembly.

In some embodiments, the assembly process of assembling the end effector device 11 and the delivery device 12 using the assembly box 700 may be as follows:

As shown in FIG. 16, the end effector device 11 may be pre-installed in the effector device chamber 710. A distal end of the outer pipe 501 of the clip 400 may abut the assembly convex. The clip 400 may be in an open state, and the clip 400 may not retract from the effector device chamber 710;

As shown in FIG. 17, the delivery device 12 may be put into the assembly groove 720 from the groove slot 722 on a side. The distal end of the sheath 200 may abut the proximal end of the accommodation pipe 500. The proximal end of the sheath 200 may be inserted into the limiting slot 721 as shown in FIGS. 16 and 17. Finally, the end cover 201 of the sheath 200 may fit snugly over the inner pipe 502. In this embodiment, a cross-section of the limiting slot 721 may be shown in FIG. 12. An area of the cross-section of the limiting slot 721 may gradually decrease along a direction from the groove slot 722 of the assembly groove 720 to a bottom of the assembly groove 720. During the process of putting the sheath 200 into the assembly groove 720 from the groove slot 722, the sheath 200 may be gradually clamped by the limiting slot 721. However, it may be not limited to this embodiment. The cross-section of the limiting slot 721 may be shown in FIG. 13. The area of the cross-section of the limiting slot 721 may successively include a narrow section and a wide section from the direction from the groove slot 722 of the assembly groove to the bottom of the assembly groove 720. A width L1 of the narrow section may be smaller than a width L2 of the wide section. In the process of putting the sheath 200 into the assembly groove 720 from the groove slot 722, the sheath 200 may traverse the narrow section and be stuck between the narrow section and the wide section.

As shown in FIGS. 20 and 21, by pushing the shaft 210 to the distal end, the connecting end 211 may be inserted into the channel of the inner pipe 502 and the large-diameter portion 212 may traverse the connecting hole 432. After the connecting end 211 is inserted into the channel of the inner pipe 502, the limit convex 520 may be compressed by the connecting end 211 and extend into the limiting concave 202. The inner pipe 502 and the sheath 200 may be connected to each other to push the sheath 200 to move to the distal end, and the accommodation pipe 500 may also be pushed to the distal end. The sheath 200 may be pulled to move to the proximal end, and the accommodation pipe 500 may also be moved to the proximal end. After the large-diameter portion 212 passes through the connecting hole 432, the connecting hole 432 may be stuck in the small-diameter portion 213. The clip 400 may be connected to the shaft 210. The movement of the shaft 210 may drive the clip 400 to move together. At this time, the clip 400 and the shaft 210 may be connected, and the sheath 200 and the accommodation pipe 500 may be connected.

As shown in FIG. 22, by pulling the shaft 210 to move towards the proximal end, the clip 400 may be driven to move towards the proximal end. The clip 400 may be compressed and closed by the accommodation pipe 500. After the clip 400 is closed, the clip 400 may be taken out of the effector device chamber 710 as shown in FIG. 21. Thus, the assembly of the delivery device 12 and the end effector device 11 may be completed. The assembled end effector instrument 10 may be used for surgery such as ligation. As shown in FIG. 24, the end effector instrument 10 may be transported to a lesion under an endoscope, and a human tissue 800 may be grabbed to prepare for the ligation.

As shown in FIG. 25, by pulling the shaft 210 to move towards the proximal end, the clip 400 may also move towards the proximal end. The clip 400 may be gradually closed for the ligation. When the clip 400 moves to the locking portion 511 or near the locking portion 511, the locking convex 602 may press the locking portion 511 outward. The elastic piece 510 may deform to make the locking portion 511 bulge the locking convex 602 outward and move the locking convex 602 to the proximal end of the locking portion 511 through the locking portion 511. At this time, the clip 400 may be closed and the locking portion 511 may be positioned at the distal end of the locking convex 602. When the locking convex 602 passes over the locking portion 511, the locking portion 511 may rebound. The locking portion 511 may extend into the accommodation pipe 500. The locking portion 511 may be positioned on a path of the locking convex 602 moving towards the distal end to prevent the locking convex 602 from moving to the distal end. In this way, the clip 400 may be locked by the locking convex 602 and the locking portion 511. The clip 400 may not move to the distal end of the accommodation pipe 500 to avoid reopening after the clip 400 is closed to ensure the stability of the ligation.

As shown in FIG. 26, after the ligation, by continuing to pull the shaft 210 to move towards the proximal end, the connecting end 211 may retract from the channel of the inner pipe 502, and the connection between the sheath 200 and the inner pipe 502 may be released. The large-diameter portion 212 may retract from the connecting hole 432, and the connection relationship between the shaft 210 and the clip 400 may be released. At this point, the connection between the delivery device 12 and the end effector device 11 may be released. The delivery device 12 may be taken out and the end effector device 11 may be left and in the ligated state.

In some embodiments, as shown in FIGS. 27-31, the end effector device 11 may include an expanding window 550 for providing an operation space for an opening operation of the first clip arm 410 and the second clip arm 420 on the accommodation portion. In some embodiments, the assembly box 700 may include an operation window 705 for providing the operation space for the opening operation on the assembly box 700. The operation window 705 may be connected to the expanding window 550. The expanding portion may extend into an interior of the end effector device 11 through the operation window 705 and the expanding window 550, facilitating the connection between the end effector device 11 and the delivery device 12.

In some embodiments, as shown in FIGS. 27-31, a side wall of the accommodation pipe 500 may be configured with the expanding window 550. The expanding window 550 may be connected to the channel of the accommodation pipe 500. The first clip arm 410 and the second clip arm 420 may be opened by the expanding window 550, so that the diameter of the connecting hole 432 may increase, which may facilitate the insertion of the large-diameter portion 212 of the shaft 210. The outer pipe 501 may be configured with the expanding window 550. The inner pipe 502 may be configured with the expanding window 550, or both the inner pipe 502 and the outer pipe 501 may be respectively configured with the expanding window 550 that may communicate with each other.

In some embodiments, as shown in FIG. 31, the housing may also be configured with the operation window 705. The operation window 705 may be connected to the effector device chamber 710. In this embodiment, both the first-half box 701 and the second-half box 702 may be configured with the operation window 705, respectively. Through the operation window 705, the end effector device 11 or the delivery device 12 may be operated during the assembly to facilitate the connection between the end effector device 11 and the delivery device 12. The diameter of the connecting hole 432 may be maintained by opening the first clip arm 410 and the second clip arm 420 through the operation portion, so that the distal end of the shaft 210 may be inserted into the connecting hole 432 to complete the connection between the shaft 210 and the clip 400.

In some embodiments, the assembly box 700 may also include an expanding portion 900. The expanding portion 900 may extend into the effector device chamber 710 through the operation window 705. The assembly box 700 may be configured with the expanding portion 900 to facilitate the expansion of the connecting hole 432. As shown in FIGS. 30-32, a head portion of the expanding portion 900 may be configured with a concave portion 910. The width of the concave portion 910 may gradually decrease from an opening of the concave portion 910 to a bottom of the concave portion 910. An inner wall of the concave portion 910 may form a compressing surface. When the first clip arm 410 and the second clip arm 420 move from the opening of the concave portion 910 to the bottom of the concave portion 910, the first clip arm 410 and the second clip arm 420 may be pressed and close to each other by the inner wall of the concave portion 910. An overlapping area of the first hole 412 and the second hole 422 may increase, i.e., the diameter of the connecting hole 432 may increase, which may facilitate the insertion of the large-diameter portion 212.

In some embodiments, when the assembly box 700 is configured to assemble the end effector device 11 and the delivery device 12 by the operator, the operator may need to manually press the assembly box 700 or manually operate the expanding portion 900 to perform the assembly operation. In order to reduce the manual operation of the operator when the end effector device 11 and the delivery device 12 are assembled, in some embodiments, the assembly device

13 may include the assembly box 700 and an assembly tool 300. The assembly tool 300 may press the assembly box 700 instead of the operator.

In some embodiments, the end effector instrument 10 may include the end effector device 11 and the delivery device 12. As shown in FIGS. 33-41, the delivery device 12 may include the operation portion (the handle 110, the sliding portion 120, and the shaft 210) and the delivery pipe (the sheath 200). The end effector device 11 may include an effector portion (the clip 400), an accommodation portion (the accommodation pipe 500), and a connecting device connecting the effector portion and the accommodation portion (not shown in the figure). The assembly system may include the assembly tool 300 and the assembly box 700 for assembling the end effector device 11 and the delivery device 12 to form the end effector instrument 10.

In some embodiments, as shown in FIGS. 39-42, the assembly box 700 may include the accommodation portion, the assembly groove 720, and a joint portion 750. The accommodation portion may be configured to accommodate the end effector device 11. The assembly groove 720 may be configured to accommodate the delivery device 12 to complete the assembly of the delivery device 12 and the end effector device 11. The joint portion 750 may be configured to fix the delivery device 12 in the assembly groove 720. In some embodiments, the accommodation portion may also be referred to as the effector device chamber 710 as described above.

Before the assembly, the end effector device 11 may be accommodated in the effector device chamber 710 of the assembly box 700. The delivery device 12 may enter into the assembly box 700 through the assembly groove 720 to complete the assembly process with the assistance of the assembly tool 300. In some embodiments, the whole assembly process may include but be not limited to two assembly processes: a first assembly that is the assembly of the sheath 200 and the accommodation pipe 500, and a second assembly that is the assembly of the shaft 210 and the clip 400.

In some embodiments, as shown in FIG. 39, in order to fix the delivery device 12 in the assembly groove 720, the joint portion 750 may include a first portion 752 and a second portion 753. The first portion may extend beyond an outer surface of the assembly groove. When the first portion 752 is pressed, the second portion 753 may enter into an interior of the assembly groove 720, thereby compressing a delivery pipe (the sheath) of the delivery device 12 positioned in the assembly groove 720 and limiting the axial movement of the delivery pipe relative to the assembly groove 720. In some embodiments, the joint portion 750 may include a wave-shaped structure, a wall-shaped structure, a tooth-shaped structure, or the like. In some embodiments, the application of a compressing force to the first portion 752 may be performed by manual hand pressing. In some embodiments, the press of the first portion may be accomplished by an assembly tool as described elsewhere in the present disclosure. In some embodiments, as shown in FIG. 39, the joint portion 750 may be a wave-shaped structure. The convex portion relative to the assembly groove 720 may be the first portion 752, and the concave portion relative to the assembly groove may be the second portion 753. In some embodiments, the joint portion 750 may include a plurality of convexes 751 as shown in FIG. 43, i.e., a part of the plurality of convexes 751 in a same direction may be used as the first portion, and the other part in a direction may be used as the second portion.

In some embodiments, the assembly box 700 may include the first-half box 701 and the second-half box 702. When the first-half box 701 and the second-half box 702 are separated, the end effector device 11 may be mounted in one of the first-half box 701 and the second-half box 702. When the first-half box 701 and the second-half box 702 are combined, the end effector device 11 may be mounted in the assembly box 700. In some embodiments, the assembly box 700 may be configured with the assembly groove 720 extending from the distal end to the proximal end. An exterior portion of the first-half box 701 and/or the second-half box 702 may be configured with the joint portion 750. The joint portion 750 may be elastic. The joint portion 750 may be arranged along a peripheral surface of the assembly groove 720. The first portion 752 of the joint portion 750 may be formed by a plurality of convexes 751 or a single convex 751. The joint portion 750 formed by the plurality of convexes 751 may have a large stress area, facilitating a stable stress and easily contacting with the sheath 200 in the assembly groove 720. As shown in FIG. 41, the joint portion 750 may be elastic. The height of the joint portion 750 may be D1 without force.

When the delivery pipe of the delivery device 12 is connected to the effector portion of the end effector device 11, in order to make the second portion 753 of the joint portion 750 press the delivery pipe and prevent the delivery pipe from being separated from the accommodation portion due to an axial movement along the assembly groove 720, in some embodiments, as shown in FIGS. 33-38, the assembly device 13 may also include the assembly tool 300. In some embodiments, the assembly tool 300 may include at least one groove 310. The assembly box 700 may enter into or retract from the at least one groove 310. When the assembly box 700 enters into the at least one groove 310, the end effector device 11 and the delivery device 12 may be assembled. More descriptions of the assembly process may be found elsewhere in the present disclosure. In some embodiments, after the end effector device 11 and the delivery device 12 are assembled, the assembly box 700 may drive the assembled end effector device 11 and delivery device 12 to retract from the groove 310. During surgery operation, the assembled end effector device 11 and delivery device 12 may be used only by removing the assembly box 700. In some embodiments, the assembly tool 300 may include a plurality of grooves 310. The plurality of grooves 300 may correspond to a plurality of assembly boxes 700. In this way, one assembly tool 300 may complete the assembly of a plurality of groups of the effector portion of the end effector device 11 and a shaft of an output device, thereby increasing the assembly efficiency.

In some embodiments, as shown in FIGS. 34-37, the assembly tool 300 may at least include a groove 310. The assembly tool 300 in FIG. 35 may include three grooves 310. Each of the three grooves 310 may separately accommodate the assembly box 700 to facilitate the assembly process. The assembly tool 300 may include a first assembly housing 300A and a second assembly housing 300B. The first assembly housing 300A and the second assembly housing 300B may be assembled from an upper housing and a lower housing, or a left housing and a right housing, or formed as a whole, which may only need to meet the requirements that the groove 310 in the housing meets the dimension and structure.

In some embodiments, in order to ensure that the assembly box 700 may enter into the groove 310 and the groove 310 may compress the joint portion 750, as shown in FIGS. 44-46, the groove 310 may include a first channel 311. A height of the first channel 311 may be smaller than or equal to a height of the joint portion 750. When the joint portion 750 enters into the first channel 311, the first channel 311 may compress the first portion 752. It should be noted that in some embodiments of the present disclosure, a height of a channel may represent a distance between an upper surface and a lower surface of the channel. In some embodiments, the joint portion 750 may be elastic and deform under the compressing of the first channel 311. In some embodiments, the groove 310 may also include a second channel 312. The second channel 312 may be connected to the first channel 311. A distal end of the second channel 312 may be connected to a proximal end of the first channel 311. A height of the second channel 312 may gradually decrease along a direction from the proximal end to the distal end. It may be understood that, as shown in FIG. 44, a proximal end may represent an end closer to the operator when the operator operates the assembly box 700 into the groove 310; and an end farther away from the operator may be a distal end. In some embodiments, a proximal end of the channel may be an entrance end of the channel, and a distal end of the channel may be an exit end of the channel. In some embodiments, the height of the first channel 311 may be equal to or smaller than a minimum height of the second channel 312. The height of the second channel 312 at the proximal end may be a maximum height, which may be greater than the height of the joint portion 750, so that the joint portion 750 may enter into the second channel 312 and the first channel 311 and be compressed by the first channel 311. In some embodiments, the groove 310 may also include a third channel 313. The third channel 313 may be connected to the first channel 311, and the third channel 313 may be arranged at the distal end of the first channel 311. In some embodiments, a minimum height of the third channel 313 may be greater than the maximum height of the first channel 311.

In some embodiments, the groove 310 of the assembly box 700 may extend from the proximal end to the distal end along an axis. The second channel 312, the first channel 311, and the third channel 313 may be respectively configured from the proximal end to the distal end. The height of the second channel 312 may gradually decrease from the proximal end to the distal end. A height of the third channel 313 may be greater than the height of the first channel 311.

In some embodiments, an exterior portion of the assembly box 700 may be configured with a convex portion 740. The convex portion 740 may be elastic. When the assembly box 700 enters into the first channel 311, the first channel 311 may compress the convex portion 740. The convex portion 740 may be elastically deformed to make the convex portion 740 in a compressed state, so that the assembly box 700 may traverse the first channel 311. When the assembly box 700 enters into the third channel 313, the convex portion 740 may be relieved from being compressed, the convex portion 740 may be restored to an original state due to elastic deformation. In some embodiments, the convex portion 740 may provide feedback information to the operator. The feedback information may be a change in the compressing force of the groove 310 on the convex portion 740. Specifically, when the operator pushes the assembly box 700 into the groove 310, it may need to traverse the second channel 312 first. The second channel 312 may not compress the convex portion 740. When the assembly box 700 enters into the first channel 311 from the second channel 312, the convex portion 740 may be compressed. The operator may sense a sharp increase of the compressing force on the convex portion 740 to know that the assembly box 700 has entered into the first channel 311 from the distal end of the second channel 312. When the operator senses that the compressing force on the convex portion 740 decreases sharply, it may be known that the convex portion 740 may be relieved from being compressed by the first channel 311 and enter into the third channel 313.

In some embodiments, as shown in FIGS. 38-41, a farthest end of the first-half box 701 and/or the second-half box 702 may be configured with a first groove 741 and a second groove 742. The first groove 741 and the second groove 742 may be hollow grooves arranged on an outer housing of the first-half box 701 and/or the second-half box 702, respectively. The convex portion 740 may be a convex portion arranged between the first groove 741 and the second groove 742. The convex portion 740 may be elastic.

When the joint portion 750 is pressed from outside to inside, a part of the joint portion 750 may enter into the assembly groove 720. If the assembly groove 720 is configured with the sheath 200 at this time, the joint portion 750 may compress the sheath 200 so that the sheath 200 and the assembly groove 720 may be axially fixed; conversely, when the compressing force of the joint portion 750 from outside to inside disappears, the joint portion 750 may be elastically restored and retract from the channel of the assembly groove 720. The sheath 200 may move axially in the assembly groove 720.

In some embodiments, the first channel 311 may be elastic. When the joint portion 750 is positioned within the first channel 311, the height of the first channel 311 may increase. After the joint portion 750 enters into the first channel, the first channel 311 may be expanded. At the same time, the first channel 311 may exert a reaction force from outside to inside on the joint portion 750. The joint portion 750 may compress the sheath 200 positioned in the assembly groove 720 to fix the sheath 200 by a compressing force with a controllable direction and magnitude.

In some embodiments, the assembly of the end effector device 11 and the delivery device 12 using the assembly box 700 and the assembly tool 300 may include the following assembly process.

Preparation Before Assembly:

As shown in FIGS. 42 and 43, the effector device chamber 710 of the assembly box 700 may accommodate the end effector device 11 (the clip 400 and the accommodation pipe 500). The joint portion 750 arranged outside the assembly groove 720 may be elastic. At this time, the joint portion 750 may be subjected to no force. The height of the joint portion 750 may be D1.

Fixing of the Assembly Box:

As shown in FIG. 44, the assembly box 700 may be pushed from the proximal end to the distal end into the groove 310 of the assembly tool 300. Firstly, the convex portion 740 arranged at the farthest end of the assembly box 300 may enter into the second channel 312. The height of the second channel 312 may gradually decrease from the proximal end to the distal end, forming a suitable guiding surface to guide the convex portion 740 into the first channel 311. Then the convex portion 740 arranged at the farthest end of the assembly box 300 may enter into the first channel 311. The convex portion 740 may shrink inward under a compressing force from the groove. Since the height of the first channel 311 is H (as shown in FIG. 37), the height of the convex portion 740 may be equal to the height H of the first channel 311. Finally, the convex portion 740 arranged at the farthest end of the assembly box 300 may enter into the third channel 313. Since the height of the third channel 313 is larger than the height of the first channel 311, the compressing force from the groove in the third channel 313 may decrease relative to that in the first channel 311. Since the height of the third channel 313 is C, the height of the convex portion 740 in the third channel 313 may be equal to the height C of the third channel 313. Since C>H, the height of the convex portion 740 in the third channel 313 may be greater than that of the convex portion 740 in the first channel 311. Therefore, when the convex portion 740 passes from the first channel 311 to the third channel 313, the convex portion 740 may suddenly change (or decrease) due to the compressing force to provide first feedback information. The first feedback information may indicate that the joint portion 750 may be positioned at the distal end of the second channel 312 and about to enter into the first channel 311. In the process of pushing the assembly box 700 into the groove 310, the first feedback information may signify the operator if the assembly box continues to move from the proximal end to the distal end when the first feedback information is generated, the joint portion 750 may enter into the first channel 311. The first feedback information may be set to signify the operator to stop pushing the assembly box 700 into the groove 310 from the distal end to the proximal end and to complete a first assembly process instead.

In some embodiments, the first assembly may refer to an assembly process of combining the delivery portion of the delivery device 12 with the accommodation portion of the end effector device 11. In some embodiments, the first assembly may include the followings.

As shown in FIG. 45, the assembly box 700 may be partially accommodated in the groove 310 of the assembly tool 300. At this time, the assembly box 700 may be temporarily fixed in the groove 310. The sheath 200 of the delivery device 12 may approach the assembly box 700 from the proximal end to the distal end. The sheath 200 may enter into the assembly groove 720 and continue to push sheath 200 from the proximal end to the distal end until the distal end of the sheath 200 of the delivery device 12 is combined with the proximal end of the accommodation pipe 500 of the end effector device 11, thus completing the first assembly process of the sheath 200 and the accommodation pipe 500.

In some embodiments, the second assembly may refer to an assembly process of establishing a connection between the delivery device 12 and the end effector device 11. In some embodiments, the second assembly may include the followings.

As shown in FIG. 46, the sheath 200 and the assembly box 700 may be continuously pushed into the groove 310 from the proximal end to the distal end at the same time. The convex portion 740 may enter into the third channel 313. The joint portion 750 may enter into the first channel 311. The joint portion 750 may be compressed from outside to inside in the first channel. The height of the joint portion 750 may be reduced from D1 to D2 (the height of the joint portion 750 positioned outside the first channel 311 may be D1; the height of the joint portion 750 positioned inside the first channel 311 may be D2). The joint portion 750 may be elastically deformed to compress the sheath 200 positioned in the assembly groove 720. The sheath 200 may be axially fixed with respect to the assembly box 700. As shown in FIG. 47, at this time, the shaft 210 may traverse the channel of the sheath 200 from the proximal end to the distal end to approach the clip 400. The sliding portion 120 may be pushed from the proximal end to the distal end until the distal end of the shaft 210 of the delivery device 12 is combined with a proximal end of the clip 400 of the end effector device 11, thus completing the second assembly process of the shaft 210 and the clip 400.

Extraction of the End Effector Instrument 10 from the Assembly Box:

After the above operations, the first assembly of the sheath 200 of the delivery device 12 and the accommodation pipe 500 of the end effector device 11 may be completed. The second assembly of the shaft 210 of the delivery device 12 and the clip 400 of the end effector device 11 may be completed. Therefore, the end effector device 11 and the delivery device 12 may be completely assembled into the end effector instrument 10 to form a whole.

The assembly box 700 may be pushed from the distal end to the proximal end. The assembly box 700 may be pushed out from the distal end to the proximal end along the groove 310. When the convex portion 740 is about to traverse the third channel 313 and enter into the first channel 311, the convex portion 740 may suddenly change (becoming larger) due to the compressing force. When the convex portion 740 becomes stuck at a step formed due to different heights of the third channel 313 and the first channel 311, the second feedback information may be generated. The second feedback information may indicate that the joint portion 750 may have just been extracted from the first channel 311 and be positioned outside the first channel 311.

As shown in FIG. 48, the joint portion 750 may be positioned outside the first channel 311. A compressing force subjected to the joint portion 750 from outside to inside may disappear, the joint portion 750 may be elastically restored. The joint portion 750 may retract from the assembly groove 720. A compressing force of the joint portion 750 on the sheath 200 from outside to inside may disappear. The sheath 200 may restore free axial movement in the assembly groove 720. As shown in FIG. 49, the end effector instrument 10 (the end effector device 11 and the delivery device 12) may be pushed from the distal end to the proximal end. The end effector instrument 10 may retract from the assembly groove 720 of the assembly box 700.

The above assembly operations may include but be not limited to the first assembly and the second assembly, and a portion thereof may be adjusted. For example, the first assembly may be completed first and then the assembly box may be fixed. After the first assembly of the sheath 200 and the accommodation pipe 500 is completed, the assembly box 700 may be fixed with the assembly tool 300, and then the second assembly may be completed.

In some embodiments, as shown in FIGS. 50-55, the third channel 313 may be configured with an elastic component 320. The elastic component 320 may provide a bias pressure to the assembly box 700 along a first direction X (see FIG. 51), so that the assembly box 700 may retract from the third channel 313. In some embodiments, a bias force may be an elastic force generated by the elastic component when the assembly box 700 contacts the elastic component 320. The first direction X of the bias force may be the same as a direction along which the assembly box 700 may retract from the third channel 313. In some embodiments, the first direction X may be understood as an axial direction from the distal end to the proximal end in the third channel. In some embodiments, the elastic component 320 may provide feedback information for the operator. The feedback information may include that a normal force from the distal end to the proximal end may be generated for the contact between the convex portion 740 and the proximal end of the elastic component 320. The feedback information provided by the elastic component 320 may signify the operator that the assembly box 700 may enter into the third channel 313 or a certain position in the third channel 313. For example, the greater the normal force felt by the operator, the further a distance that the assembly box 700 may enter into the third channel 313. In some embodiments, as shown in FIG. 51, the assembly tool 300 may also include a fourth channel 314. One end of the elastic component 320 may be fixedly arranged in the fourth channel 314. The fourth channel 314 may be connected to the first channel 311, the second channel 312, and the third channel 313. The fourth channel 314 may be arranged at a distal end of the third channel 313, and another end of the elastic component 320 may extend from the distal end to the proximal end into an interior of the third channel 313. In some embodiments, the assembly tool may omit the fourth channel. One end of the elastic component 320 may be directly fixed to the distal end of the third channel 313, and another end may extend into the interior of the third channel 313. In some embodiments, the elastic component may be a spring.

In some embodiments, the groove 310 of the assembly tool 300 may also be configured with the fourth channel 314. The fourth channel 314 may be connected to the first channel 311, the second channel 312, and the third channel 313. The fourth channel may be arranged at the distal end of the third channel. The elastic component 320 may be fixedly arranged in the third channel. The elastic component 320 may extend from the distal end to the proximal end as shown in FIG. 50.

A difference in the assembly process of an assembly system configured with the elastic component 320 may include that the processes of fixing the assembly box, the first assembly, the second assembly, and the retraction of the end effector instrument 10 from the assembly box may be different, which are described in detail below.

Preparation Before Assembly:

There is no difference in this process. More descriptions of the preparation before assembly may be found elsewhere in the present disclosure.

Fixing of the Assembly Box:

As shown in FIG. 51, when the convex portion 740 passes from the first channel 311 into the third channel 313, the convex portion 740 may suddenly change (or decrease) due to a compressing force, and first feedback information may be provided. At the same time, the convex portion 740 may abut the proximal end of the elastic component 320 to generate a normal force from the distal end to the proximal end, thereby providing third feedback information. The first feedback information and the third feedback information may be generated simultaneously or continuously, or only the third feedback information may be generated without the generation of the first feedback information. The purpose of the first feedback information and the third feedback information may be to signify the operator to stop pushing the assembly box 700 from the distal end to the proximal end into the groove 310 and to complete the first assembly process instead.

The First Assembly:

As shown in FIG. 52, the assembly box 700 may be partially accommodated in the groove 310 of the assembly tool 300. Due to the configuration of the elastic component 320, if the assembly box 700 needs to continue to enter into the groove 310 from the proximal end to the distal end, a pushing force may need to be large enough to overcome the resistance from the elastic force exerted by the elastic component 320. At this time, the assembly box 700 may be temporarily fixed in the groove 310. The sheath 200 of the delivery device 12 may approach the assembly box 700 from the proximal end to the distal end. The sheath 200 may enter into the assembly groove 720 and continue to push sheath 200 from the proximal end to the distal end until the distal end of the sheath 200 of the delivery device 12 is combined with the proximal end of the accommodation pipe 500 of the end effector device 11, thus completing the first assembly process of the sheath 200 and the accommodation pipe 500.
The Second Assembly:

As shown in FIG. 53, the sheath 200 and the assembly box 700 may be simultaneously pushed from the proximal end to the distal end to enter into the groove 310. A pushing force from the proximal end to the distal end may need to be large enough to overcome the resistance from the elastic force exerted by the elastic component 320. The elastic component 320 may be compressed. The convex portion 740 may enter into the third channel 313 and the joint portion 750 may enter into the first channel 311. The joint portion 750 may be pressed from outside to inside in the first channel. The height of the joint portion 750 may be reduced from D1 to D2 (the height of the joint portion 750 outside the first channel 311 may be D1; the height of the joint portion 750 inside the first channel 311 may be D2). The joint portion 750 may be elastically deformed to press the sheath 200 in the assembly groove 720. The sheath 200 may be axially fixed relative to the assembly box 700. At this time, the shaft 210 may traverse the channel of the sheath 200 from the proximal end to the distal end to approach the clip 400. The sliding portion 120 may be pushed from the proximal end to the distal end until the distal end of the shaft 210 of the delivery device 12 is combined with the proximal end of the clip 400 of the end effector device 11, thus completing the second assembly process of the shaft 210 and the clip 400.
Retraction of the End Effector Instrument 10 from the Assembly Box:

In some embodiments, the elastic component 320 may be elastically restored to provide fourth feedback information. The elastic component 320 may provide a pushing force from the distal end to the proximal end to force the assembly box 700 to move from the distal end to the proximal end. At this time, the first assembly of the sheath 200 and the accommodation pipe 500 and the second assembly of the shaft 210 and the clip 400 have been completed, i.e., the end effector device 11 and the delivery device 12 have been assembled to form the end effector instrument 10. At this time, the fourth feedback information may indicate that it is necessary to separate the end effector instrument 10 from the assembly box and the assembly tool.

As shown in FIG. 54, the joint portion 750 may be positioned outside the first channel 311. A compressing force subjected to by the joint portion 750 from outside to inside may disappear, and the joint portion 750 may be elastically restored. The joint portion 750 may retract from the assembly groove 720. The compressing force of the joint portion 750 on the sheath 200 may disappear. The sheath 200 may restore free axial movement in the assembly groove 720. As shown in FIG. 55, the end effector instrument 10 (the end effector device 11 and the delivery device 12) may be pushed from the distal end to the proximal end. The end effector instrument 10 may retract from the assembly groove 720 of the assembly box 700.

The elastic component 320 may be elastically restored to apply a pushing force to the assembly box 700 from the distal end to the proximal end. If the pushing force is too large, the assembly box 700 may completely retract from the groove 311. At this time, the convex portion 740 positioned at a distal end of the assembly box 700 may become stuck at a step formed due to different heights of the third channel 313 and the first channel 311. A certain normal force from the proximal end to the distal end may be generated. Therefore, by arranging the elastic component 320 and the convex portion 740 at the same time, the assembly box 700 may easily retract from the groove 310, and a speed of the retraction may be safe and controllable.

It should be noted that the assembly box 700 of the present disclosure may not only be used to fix the end effector device 11 and the delivery device 12 when the end effector device 11 and the delivery device 12 are assembled. In some embodiments, since the end effector device 11 may be installed in the assembly box 700 after factory disinfection, the assembly box 700 may also be configured to package the end effector device 11.

In some embodiments, in order to limit a relative movement between the delivery device 12 and the assembly box, the assembly box 700 may also include a limiting portion. The limiting portion may be configured to limit the relative movement between the delivery device 12 and the assembly box 700. In some embodiments, the assembly box 700 may include a housing 760. The limiting portion may be positioned at the housing 760. The delivery device 12 may include the delivery pipe (e.g., the sheath 200). The limiting portion may limit the relative movement between the delivery device and the housing 760. In some embodiments, the limiting portion may include one of a groove body, a limiting channel, or a buckle. For example, a part of the delivery pipe may be clamped in the groove body, the limiting channel, or the buckle. In some embodiments, at least one convex point may be arranged in the limiting portion. When a part of the delivery pipe is connected to the limiting portion, a friction between the limiting portion and the delivery pipe may increase, thereby increasing a limiting effect. In some embodiments, the limiting portion may exclude the at least one convex point. A roughness of the surface connected to the delivery pipe may increase to achieve the same effect of the at least one convex point.

In some embodiments, as shown in FIG. 56, the end effector instrument 10 may include the end effector device 11 and the delivery device 12. The delivery device 12 may include the handle 110 and the sheath 200 extending from the distal end to the proximal end. A count of the end effector device 11 may be multiple. The multiple end effector devices 11 may be sterilized and separately sealed in multiple assembly boxes 700. During surgery operation, the individually sealed assembly boxes 700 may be opened one by one as required, and then the assembly of the delivery device 12 and the end effector device 11 may be completed to assemble the end effector instrument 10.

The count of the end effector devices 11 and the count of the delivery devices 12 may be matched as required. As shown in FIG. 56, four end effector devices 11 (the end effector devices 11 may be separately stored in the assembly box 700, and the assembly boxes 700 may be sealedly stored in the housing 760 as shown in FIG. 58) and one delivery device 12 (including the handle 110 and the sheath 200) may be selected. The distal end of the delivery device 12 has been assembled with the end effector device 11 to form the end effector instrument 10 before factory packaging.

As shown in FIG. 57, the limiting portion may include a plurality of limiting grooves 763. The sheath 200 of the delivery device 12 may clamp with the limiting grooves 763. The limiting grooves 763 may limit a relative movement between the delivery device 12 and the housing 760 configured with the assembly box 700.

As shown in FIG. 59, the housing 760 may include a convex portion 761 and a non-convex portion 762. The convex portion 761 may be convex relative to a plane of the non-convex portion 762. The accommodation box 700 may be accommodated inside the convex portion 761. The convex portion 761 may include a surface of a convex portion 761A and a side surface of a convex portion 761B. The limiting groove 763 may be formed by traversing the surface of the convex portion 761A and the side surface of the convex portion 761B.

As shown in FIG. 60, a plurality of convex points 764 may be arranged in the limiting groove 763. The convex points 764 may increase a friction between the limiting groove 763 and the sheath 200 to make a limiting effect between the limiting groove 763 and the sheath 200 firmer, i.e., to complete the limiting between the delivery device 12 and the assembly box 700.

In some embodiments, as shown in FIGS. 61 and 62, the convex portion 760 may include the surface of the convex portion 761A and a plurality of side surfaces of the convex portion 761B. The limiting groove 763 traversing the plurality of side surfaces of the convex portion 761B may be formed.

In some embodiments, as shown in FIGS. 63 and 64, the housing 760 may include the convex portion 761 and the non-convex portion 762. The convex portion 761 may be convex relative to a plane of the non-convex portion 762. The accommodation box 700 may be accommodated inside the convex portion 761. The limiting portion may be arranged at the non-convex portion 762 and include the plurality of limiting grooves 763.

In some embodiments, as shown in FIGS. 65 and 66, the housing 760 may include the convex portion 761 and the non-convex portion 762. The convex portion 761 may be convex relative to a plane of the non-convex portion 762. The accommodation box 700 may be accommodated inside the convex portion 761. The limiting portion may be arranged at the non-convex portion 762. The limiting portion may be folded by the non-convex portion 762 to form a limiting channel 763'. The limiting portion may also include a buckle 765. When the sheath 200 enters into the limiting channel 763', the buckle 765 may fix the limiting channel 763', so that the limiting channel 763' and the sheath 200 complete a bulking connection, i.e., a limiting between the delivery device 12 and the assembly box 700 may be completed.

In some embodiments, as shown in FIG. 67 and FIG. 68, the limiting portion may include the limiting channel 763'. A cooperation between the sheath 200 and the limiting channel 763' may be completed by relying on a material elasticity of the non-convex portion 762, i.e., a limiting between the delivery device 12 and the assembly box 700 may be completed.

In some embodiments, as shown in FIGS. 69-71, the limiting portion may include the limiting channel 763' and a groove 766. After the sheath 200 enters into the limiting channel 763', the non-convex portion 762 may enter into the groove 766, so that a limiting relationship between the limiting channel 763' and the sheath 200 may be firmer, i.e., a limiting between the delivery device 12 and the assembly box 700 may be completed.

In some embodiments, as shown in FIG. 72, the limiting portion may be a groove body. The limiting portion may include a first limiting groove 763A and a second limiting groove 763B. The end effector instrument 10 may be accommodated in the first limiting groove 763A. The assembly box 700 may be accommodated in the second limiting groove 763B. The limiting portion may complete a limiting between the delivery device 12 and the assembly box 700.

With regard to the assembly of the end effector device 11 and the delivery device 12 using the assembly device 13, some embodiments of the present disclosure may also provide an assembly operation method of the end effector instrument 10, which may be used for the end effector instrument 10 described in any embodiment of the present disclosure. FIG. 73 is a flowchart illustrating an assembly and operation method of an end effector instrument according to some embodiments of the present disclosure. In some embodiments, process 1000 may include the following operations.

In operation 1100, the assembly box 700 may be controlled to enter into the groove 310 of the assembly tool 300.

In some embodiments, as shown in FIG. 74, the operation 1100 may include the followings.

In sub-operation 1110, the convex portion 740 of the assembly box 700 may be controlled to enter into the first channel 311 from the second channel 312. In some embodiments, the operator may push the assembly box 700 into the groove 310 of the assembly tool 300 so that the convex portion 740 at the distal end of the assembly box 700 may enter into the first channel 311 from the second channel 312.

In sub-operation 1120, the convex portion 740 may be controlled to enter into the third channel 313 from the first channel 311 and to obtain the first feedback information. In some embodiments, when the operator pushes the convex portion 740 of the assembly box 700 to move in the first channel 311, the convex portion 740 may be compressed by the first channel 311, and a compressing force may be generated and perceived by the operator. When the convex portion 740 extracts from the first channel 311 and enters into the third channel 313, the convex portion 740 may be relieved from being compressed, and the compressing force may disappear. The operator may perceive a sudden change of compressing force and know that the convex portion 740 has entered into the third channel 313. That is, the first feedback information may be the compressing force or a change of the compressing force perceived by the operator. The first feedback information may signify the operator of the position of the assembly box 700 in the groove 310.

In sub-operation 1130, in response to the first feedback information, the assembly box 700 may be stopped moving. In some embodiments, after the operator senses the change of the compressing force, i.e., the first feedback information may signify the operator that the convex portion 740 of the assembly box 700 has entered into the third channel 313, the assembly box 700 may be stopped pushing.

It should be noted that the sub-operation 1110, the sub-operation 1120, and the sub-operation 1130 may be only exemplary embodiments of one of the operation methods of operation 1100 and should not be understood as restrictions on operation 1100. In some embodiments, the operation 1100 may also include other sub-operations. For example, the operation 1100 may include the following operations. The convex portion 740 of the assembly box 700 may be controlled to enter into the first channel 311 from the second channel 312. The convex portion 740 may be controlled to enter into the third channel 313 from the first channel 311. In response to the third feedback information, the assembly box 700 may be stopped moving. The third feedback information may be provided by the elastic component 320 arranged in the third channel 313, i.e., when the operator senses the elastic force provided by the elastic component 320, the operator may know that the convex portion 740 has entered into the third channel 313.

In operation 1200, the delivery pipe of the delivery device 12 may be controlled to enter into the assembly groove and achieve the first assembly with the accommodation portion of the end effector device 11.

In some embodiments, the operator may push the delivery pipe from a proximal end to a distal end to combine the distal end of the delivery pipe with the proximal end of the accommodation portion to complete the first assembly. It should be noted that after the operation 1200 is completed, the accommodation portion of the assembly box 700 may enter into a sliding groove of the assembly tool 300. However, the assembly groove 720 and the joint portion 750 of the assembly box 700 may be still outside the assembly tool 300. More descriptions of the first assembly may be found elsewhere in the present disclosure (for example, FIG. 45 and the descriptions thereof), which are not repeated here.

In operation 1300, the assembly box 700 and the delivery pipe may be controlled to continue to move inside the groove 310 so that the delivery pipe may be axially fixed in the assembly groove 720.

In some embodiments, the operator may continue to push the assembly box 700 so that the joint portion of the assembly box 700 and the delivery pipe positioned in the assembly groove may move towards an interior the groove 310 and enter into the first channel 311 after passing through the second channel 312. Since the height of the first channel 311 is smaller than the height of the joint portion and the joint portion may be elastic, the first channel 311 may compress the first portion 752 of the joint portion 750 to allow the second portion 753 of the joint portion to enter into the assembly groove 720. The second portion 753 may compress the delivery pipe, so that the joint portion may clamp the delivery pipe along a radial direction of the delivery pipe to fix the delivery pipe axially in the assembly groove 720. In some embodiments, the operator may manually compress the joint portion 750 to fix the delivery pipe axially in the assembly groove 720.

In operation 1400, the shaft of the delivery device 12 may be controlled to move towards the end effector device 11 to achieve the second assembly with the clip 400.

In some embodiments, after the first assembly is completed, the delivery pipe and the accommodation portion may be combined with each other. Axial fixation of the delivery pipe and the assembly groove may be realized. The operator may continue to push the shaft in the delivery pipe, so that the connecting end 211 of the shaft 210 may enter into the accommodation portion and compress the limiting convex 520 of the accommodation portion, so that the limiting convex 520 of the accommodation portion may extend into the limiting concave 202 of the delivery pipe to achieve a releasable connection between the delivery pipe and the accommodation portion. The shaft 210 may be further pushed, so that the large-diameter portion 212 of the shaft 210 may enter into the connecting hole 432 of the clip 400 to establish the connection between the shaft 210 and the clip 400, i.e., the second assembly. More descriptions of the second assembly may be found elsewhere (for example, FIG. 46 and the descriptions thereof) in the present disclosure.

In operation 1500, the assembled end effector device 11 and delivery device 12 may retract from the assembly box 700.

In some embodiments, the operator may pull the assembly box 700 to move from the inside (the distal end) of the groove 310 to the outside (the proximal end) of the groove 310 and obtain the second feedback information. In some embodiments, the second feedback information may be a normal force felt by the operator when the convex portion 740 becomes stuck at a step formed due to different heights of the third channel 313 and the first channel 311. In some embodiments, the operator may determine that the joint portion 750 may retract from the first channel 311 based on the second feedback information. At this time, the operator may retract the end effector device 11 and the delivery device 12 from the assembly groove 720.

In some embodiments, since the elastic component is arranged in the third channel 313 of the groove 310, during the second assembly, the assembly box 700 may abut the elastic component 320. At this time, the assembly box 700 may receive a pushing force applied by the operator from the proximal end to the distal end and an elastic force applied by the elastic component from the distal end to the proximal end, so that the assembly box 700 may not move in the third channel 313. After the second assembly is completed, the operator may stop pushing the assembly box 700, such that an elastic force generated by the elastic component may be large enough to drive the assembly box 700 to move from the inside (the distal end) of the groove 310 to the outside (the proximal end) of the groove 310. In some embodiments, when the joint portion 750 of the assembly box 700 retracts from the first channel 311, the elastic component 320 may provide fourth feedback information to the operator. For example, the operator may feel that the elastic component 320 has lost the elastic force. In some embodiments, when the joint portion 750 retracts from the first channel 311, i.e., when the operator receives the fourth information feedback, the operator may retract the end effector device 11 and the delivery device 12 from the assembly groove 720.

In some embodiments, the operator may also directly pull the assembly box 700 out of the groove 310. After that, the operator may directly open the assembly box 700, and then take out the assembled end effector device 11 and the delivery device 12 for usage in surgery.

The possible beneficial effects of the embodiments of the present disclosure may include but be not limited to the followings.

1. An end effector instrument may include an end effector device and a delivery device.

The end effector device may include a clip and an accommodation pipe. The accommodation pipe may be configured with a channel. An inner pipe and an outer pipe may be configured with a channel, respectively. The channels of the inner pipe and the outer pipe may be connected to form the channel of the accommodation pipe. The clip may be accommodated into the channel of the accommodation pipe from a distal end. An outer wall of the inner pipe may be configured with a limiting convex. The limiting convex may be configured to cooperate with a limiting concave to establish a connection and release of a sheath and the inner pipe. The accommodation pipe may be divided into the inner pipe and the outer pipe. After fine structures are made on the inner pipe and the outer pipe, respectively, the outer pipe may fit snugly over the inner pipe, so that the inner pipe and the outer pipe may form the accommodation pipe, which may be convenient for production and manufacturing, especially for the production and manufacturing of a small device for an endoscopic operation such as an end effector instrument. The inner pipe may be configured with the channel, and the outer pipe may also be configured with the channel. The inner pipe and the outer pipe may only need to be connected together. A depth of the inner pipe inserting into the outer pipe may be set arbitrarily according to actual needs. The channel of the inner pipe may be connected to the channel of the outer pipe. The channel of the inner pipe and the channel of the outer pipe may together constitute a movement channel of the clip, and the clip may be accommodated in the movement channel from a distal end.

The delivery device may include a sheath and a shaft. The shaft may be arranged in a channel of the sheath. A distal end of the shaft may be configured with a connecting end. An inner wall of the sheath may be configured with a limiting concave. The limiting concave may be configured to cooperate with the limiting convex to establish a connection and release of the sheath and the inner pipe.

When the sheath fits snugly over the limiting convex, the connecting end may enter into or retract from the inner pipe. When the connecting end enters into the inner pipe, the limiting convex may be compressed by the connecting end and extend into the limiting concave. The inner pipe and the sheath may be connected to each other to push the sheath to move to the distal end. The accommodation pipe may also be pushed to the distal end. When the sheath is pulled to move to a proximal end, the accommodation pipe may also be moved to the proximal end. When the connecting end extracts from the inner pipe, the limiting convex may extract from the limiting concave. A connection relationship between the accommodation pipe and the sheath may be released. For example, after the clip is ligated, the sheath may be taken out separately, and the clip may be left at a lesion to remain ligated.

2. The clip may be configured with a locking convex. The locking convex may be configured to lock a position relationship between the clip and the accommodation pipe to prevent the clip from moving from a distal end of the accommodation pipe to open. The outer pipe may be configured with an elastic piece. The inner pipe and the outer pipe may be configured as the channel, respectively. The channels of the inner pipe and the outer pipe may be connected to form the channel of the accommodation pipe. The elastic piece may at least partially extend into the channel of the accommodation pipe. A part of the elastic piece extending into the channel of the accommodation pipe may form a locking portion. The clip may be received into the channel of the accommodation pipe from the distal end of the accommodation pipe. When the locking convex is positioned at the distal end of the locking portion, the clip may move towards the distal end of the accommodation pipe. When the clip is moved from the distal end to the proximal end, the clip may gradually close under the compressing of the accommodation pipe. When the clip moves to the locking portion or near the locking portion, the locking convex may compress the locking portion outward. The elastic piece may deform to make the locking portion bulge the locking convex outward such that the locking convex may be moved to the proximal end of the locking portion through the locking portion. At this time, the clip may close and the locking portion may be positioned at the distal end of the locking convex. When the locking convex passes over the locking portion, the locking portion may rebound. The locking portion may extend into the accommodation pipe. The locking portion may be positioned on a path of the locking convex moving to the distal end to prevent the locking convex from moving to the distal end. In this way, the clip may be locked by the locking convex and the locking portion. The clip may be unable to move to the distal end of the accommodation pipe to avoid reopening after the clip is closed. Moreover, the structure of the spring and the locking portion may be simple.

The rebounding of the elastic piece may meet the following requirements. The locking portion may be bulged during a compressing of the locking convex. The locking portion may rebound after the locking convex passes over the locking portion to block the locking portion, which does not mean that the elastic piece must be an elastic material. In fact, the elastic piece may be made of any material. Preferably, the material of the elastic piece may be the same as a material of the accommodation pipe. The elastic piece may be a part of a side wall of the accommodation pipe after cutting. One end of the elastic piece may be connected to the side wall of the accommodation pipe, another end may extend into the channel of the accommodation pipe.

3. The inner pipe may be configured with a guiding groove. The locking convex may slide in the guiding groove. The guiding groove may guide the locking convex to move to a position of the locking portion, facilitating the locking. Preferably, the locking portion may extend into the guiding groove.

4. The guiding groove may be configured with a positioning convex. The positioning convex may be positioned at a proximal end of the locking portion. When the locking portion prevents the locking convex from moving to the distal end, the locking convex may be positioned between the positioning convex and the locking portion. The locking portion may restrict the locking convex from moving towards the distal end, and the positioning convex may restrict the locking convex from moving towards the proximal end, so that a position of the clip may be constrained by the locking portion and the positioning convex at the same time, and be unable to move towards the proximal end or the distal end. A closed state of the clip may be maintained, and the closed state of the clip may be stable.

5. The clip may include a first clip arm, a second clip arm, and a connecting pin. The first clip arm and the second clip arm may be connected through the connecting pin. One end or both ends of the connecting pin may form a locking convex. The connecting pin may not only connect the first clip and the second clip but also lock the clip. The structure may be simple. When both ends of the connecting pin form the locking convex, there may be two elastic pieces, which may correspond to both ends of the connecting pin respectively.

6. The clip may also include an elastic ring. The elastic ring may fit snugly over the connecting pin. The elastic ring may be positioned between the first clip arm and the second clip arm. The elastic ring may be compressed by the first clip arm and the second clip arm. The elastic ring may provide an elastic force. An elastic direction of the elastic force of the elastic ring may refer to a direction in which the first clip arm and the second clip arm may be far away from each other at a position abutting the elastic ring. Preferably, the elastic ring may be a helicoidal spring. The helicoidal spring may fit snugly over the connecting pin through its helicoidal coil.

7. The proximal end of the first clip arm may be configured with a first bending portion bending towards the second clip arm. The first bending portion may be configured with a first hole. A proximal end of the second clip arm may be configured with a second bending portion bending towards the first clip arm. The second bending portion may be configured with a second hole. The first hole and the second hole may at least partially overlap and communicate, and the overlapping and communicating part of the first hole and the second hole may form a connecting hole. The "At least partially overlapping" may include a partially overlapping communication and a completely overlapping communication. The partially overlapping communication may refer to that the first hole and the second hole may be slightly staggered without complete overlapping. The completely overlapping communication may refer to that the first hole completely overlaps the range of the second hole or the second hole completely overlaps the range of the first hole. After the first hole and the second hole are connected, the connection part between the first hole and the second hole may form the connecting hole. A large-diameter portion may need to traverse the first hole and the second hole to establish the connection. The elastic force of the elastic ring may make the first clip arm and the second clip arm tend away from each other, so that the first hole and the second hole may be staggered with each other, and an aperture of the connecting hole may tend to be reduced. A distal end of the shaft may be configured with a large-diameter portion and a small-diameter portion. The large-diameter portion may be positioned at a distal end of the small-diameter portion. A diameter of the large-diameter portion may be greater than a diameter of the small-diameter portion. A distal end of the connecting end may be configured with a large-diameter portion and a small-diameter portion. The small-diameter portion may be positioned between the large-diameter portion and the connecting end. The diameter of the large-diameter portion may be greater than a diameter of the small-diameter portion. The diameter of the small-diameter portion may be the same as or different from the diameter of the connecting end. Alternatively, the small-diameter portion may be a part of the distal end of the connecting end.

8. The side wall of the accommodation pipe may be configured with an expanding window. The expanding window may be connected to the channel of the accommodation pipe. The first clip arm and the second clip arm may be expanded through the expanding window to increase an aperture of the connecting hole and facilitate insertion of the large-diameter portion of the shaft. The outer pipe may be configured with the expanding window, or the inner pipe may be configured with the expanding window, or both the inner pipe and the outer pipe may be configured with a mutually connected expanding window.

9. The assembly box may be configured to assemble the end effector device with the delivery device. The assembly box may include a connection between the sheath and the accommodation pipe and a connection between the shaft and the clip. The assembly box may include a housing. The housing may be configured with an effector device chamber and an assembly groove. A side of the assembly groove may be configured with a groove slot. The sheath may be put into the assembly groove through the groove slot, which may be convenient for operation. Preferably, the groove slot of the assembly groove may be positioned on a plane where the clip is open. The distal end of the assembly groove may be connected to the effector device chamber. A proximal end of the assembly groove may be configured with a limiting slot. The limiting slot may be connected to the groove slot. A width of the limiting slot may be smaller than a width of the assembly groove. The sheath may be clamped into the limiting slot. The width of the limiting slot may be by way of interference fit with the sheath. When there is no external force, the sheath may be not easy to retract from the limiting slot, which may be convenient for positioning the sheath and more easily to complete the assembly.

10. A cross-section of the limiting slot may successively include a narrow section and a wide section along a direction from the groove slot to a bottom of the assembly groove. A width of the narrow section may be smaller than a width of the wide section. During an assembly, the sheath may traverse the narrow section of the limiting slot and be clamped between the narrow section and the wide section of the limiting slot. Vibration or sound when the sheath traverses the narrow section may be felt, which may signify an operator that the sheath may be installed in place and a handling feel may be good.

11. The housing may also be configured with an operating window. The operating window may be connected to the effector device chamber. The effector device chamber may be configured to place the end effector device. Preferably, the end effector device may be disinfected and sealed in the assembly box when the end effector device leaves a factory, ensuring the cleanliness of the end effector device. Through the operating window, the end effector device or the delivery device may be operated during the assembly to facilitate a connection between the end effector device and the delivery device. For example, the first clip arm and the second clip arm may be expanded and the diameter of the connecting hole may be maintained by an operating portion, facilitating the distal end of the shaft being inserted into the connecting hole and establishing a connection between the shaft and the clip.

12. The assembly box may also include an expanding portion. The expanding portion may extend into the effector device chamber through the operating window. The assembly box may be equipped with the expanding portion to facilitate the expansion of the connecting hole.

13. A head portion of the expanding portion may be configured with a concave portion. A width of the concave portion may gradually decrease from an opening of the concave portion to a bottom of the concave portion. An inner wall of the concave portion may form a compressing surface. When the first clip arm and the second clip arm move from the opening of the concave portion to the bottom of the concave portion, the first clip arm and the second clip arm may be pressed by the inner wall of the concave portion and close to each other. An overlapping area of the first hole and the second hole may increase, i.e., an aperture of the connecting hole may increase, which may be convenient for insertion of the large-diameter portion.

14. The effector device chamber may be configured with an assembly convex. The assembly convex may be configured to abut the accommodation pipe. During assembly, the accommodation pipe may abut the assembly convex. The sheath may be put into the assembly groove to push the sheath to move from the proximal end to the distal end, so that the sheath may fit snugly over the inner pipe. At this time, by pushing the shaft to move from the proximal end to the distal end, the connecting end of the shaft may be inserted into the channel of the inner pipe. The inner pipe may be connected to the sheath. By continuing to move the shaft to the distal end, the shaft may be inserted into the connecting hole. The shaft may be connected to the clip. During this process, since the assembling convex abuts the accommodation pipe, when the sheath or the shaft moves from the proximal end to the distal end, the movement of the accommodation pipe to the distal end may be bulged, which may be convenient for assembly.

15. The joint portion of the assembly box may be positioned outside a first channel of the assembly tool. The sheath of the delivery device may move axially in the assembly groove of the assembly box. The joint portion of the assembly box may be positioned in the first channel of the assembly tool. The sheath of the delivery device may be axially fixed in the assembly groove of the assembly box. By utilizing a cooperation between components of the assembly tool and the assembly box, the sheath may be controlled to be axially moved or axially fixed in the assembly groove according to the needs of the assembly process, replacing the manual operation of an assembly personnel, and improving the assembly efficiency and the success rate of assembly.

16. The distal end of the shaft may be releasably connected to the proximal end of the clip. The distal end of the sheath may be releasably connected to the proximal end of the accommodation pipe. The assembly of the end effector device and the delivery device may include a first assembly of the sheath and the accommodation pipe and a second assembly of the shaft and the clip. The assembly of the end effector device and the delivery device may be divided into the first assembly and the second assembly. The first assembly and the second assembly may be independent from each other. A respective assembly sequence of the first assembly and the second assembly may be adjusted and optimized according to a specific structure of the assembly tool and the assembly box. The adjustment and optimization of different assembly operations may be realized by improving the assembly box and/or the assembly tool, which may be more suitable for industrial production and user operation.

17. The assembly tool may include at least one groove. The at least one groove may extend axially relative to an assembly direction of the assembly box. When the assembly tool includes a plurality of grooves, a plurality of delivery devices may be assembled with end effector devices in a plurality of assembly boxes at the same time to complete the assembly of the plurality of end effector devices, increasing utilization space of the assembly tool. A dimension and shape of the at least one groove may only need to accommodate the assembly box and facilitate the assembly process of the end effector device and the delivery device. No matter what forming method of the at least one groove of the assembly tool is, the assembly tool with the at least one groove meeting the assembly requirements has simple manufacture and low cost.

18. A height of the first channel of the groove of the assembly tool may be H. The joint portion of the assembly box may be elastic. The joint portion may be positioned outside the first channel. The height of the joint portion may be D1. The joint portion may be positioned in the first channel. A height of the joint portion may be D2. D1>H≥D2. An elastic joint portion may be a convex arranged outside the assembly groove. After the joint portion enters into the first channel, the joint portion may be elastically deformed under a compressing force from outside to inside and compress the sheath positioned in the assembly groove, so that the sheath may be axially fixed relative to the assembly box. A direction and magnitude of the compressing force required to fix the sheath may be controlled by controlling the length of the joint portion, a height of the convex, a material elasticity, or other factors of the joint portion.

19. The assembly tool may be elastic. When the joint portion is positioned in the first channel, the height of the first channel may increase. As an alternative or supplementary scheme of the elastic joint portion, in the scheme that the assembly tool has elastic, a material forming the groove of the assembly tool may be elastic. After the joint portion enters into the first channel, the groove may be stretched. At the same time, the joint portion may receive a reaction force from outside to inside by the first channel. The joint portion may compress the sheath positioned in the assembly groove to fix the sheath by a compressing force with a controllable direction and magnitude.

20. The groove may also be configured with a second channel. The second channel and the first channel may be connected to each other. The second channel may be arranged at a proximal end of the first channel. A height of the second channel may gradually decrease from the proximal end to the distal end. When the assembly box moves into the groove of the assembly tool from the distal end to the proximal end, it may traverse the second channel (i.e. an opening with a changing height) whose height decreases.

The second channel may have a function of guiding the assembly box into the groove.

21. The groove may also be configured with a third channel. The third channel and the first channel may be connected to each other. The third channel may be arranged at the distal end of the first channel. The height of the third channel may be greater than that of the first channel. An exterior of the assembly box may be configured with a convex portion. The convex portion may be elastic. The height of the convex in the first channel may be smaller than the height of the convex in the third channel. When the convex portion enters into the channels with different heights and dimensions, resistance felt by the operator may be different, which may signify the operator of different stages of the entry of the assembly box into the groove, thereby allowing the operator to adjust the assembly operations.

22. The convex portion may move from the proximal end to the distal end. When the convex portion enters into the third channel from the first channel, a normal force received by the convex portion may change to provide first feedback information. The first feedback information may be if the convex portion continues to move from the proximal end to the distal end to the third channel, the joint portion may enter into the first channel. The first feedback information may be converted to an audio prompt generated when the convex portion enters into different channels of the groove. Alternatively, the first feedback information may be a feel sensed by the operator in response to a sudden decrease in the resistance. Therefore, the operator may stop pushing the assembly box from the distal end to the proximal end to enter into the groove, but connect the sheath with the accommodation pipe along the assembly groove to complete the first assembly process.

23. The convex portion may move from the distal end to the proximal end. When the convex portion enters the first channel from the third channel. A normal force received by the convex portion may change to provide second feedback information. The second feedback information may be that: the joint portion has just retracted from the first channel and is positioned outside the first channel. The second feedback information may be converted to an audio prompt generated when the convex portion enters into different channels of the groove. Alternatively, the second feedback information may be a feeling sensed by the operator in response to a sudden increase of the normal force.

24. The groove may also be configured with a fourth channel. An elastic component may be arranged in the fourth channel. The elastic component, such as a spring, may be arranged in the groove. An elasticity of the elastic component may be controlled by controlling a count of turns or a length of the spring, such that the operation may be simple and convenient.

25. When the assembly box enters into the groove from the distal end to the proximal end, the distal end of the assembly box may abut the elastic component to provide third feedback information. The third feedback information may be that: the assembly box may continue to move from the proximal end to the distal end, and the joint portion may enter into the first channel. The third feedback information may be converted to a visual prompt that the elastic component and the distal end of the assembly box contact through a transparent groove. Alternatively, the third feedback information may be a hand feeling of the operator in response to a normal force generated by the abutting between the distal end of the assembly box and the elastic component. Therefore, the operator may stop pushing the assembly box from the distal end to the proximal end to enter into the groove, but may connect the sheath with the accommodation pipe along the assembly groove to complete the first assembly process.

26. The joint portion may be positioned in the first channel. The elastic component may be compressed by the assembly box. The elastic component may be elastically restored to provide fourth feedback information. The fourth feedback information may be that: a pushing force from the distal end to the proximal end may be provided to force the assembly box to move from the distal end to the proximal end; at this time, the first assembly of the sheath and the accommodation pipe and the second assembly of the shaft and the clip have been completed, i.e., the end effector device and the delivery device have been assembled to form the end effector instrument. At this time, the fourth feedback information may prompt that the end effector instrument needs to be separated from the assembly box and assembly tool subsequently. At this time, the elastic component may generate a pushing force from the distal end to the proximal end due to the elastic recovery to facilitate the assembly box extracting from the groove to complete the subsequent process.

27. The groove may also be configured with a third channel and a fourth channel. The fourth channel may be configured with the elastic component. The height of the third channel may be greater than the height of the first channel. The assembly box may be configured with a convex portion. The convex portion may be elastic. The height of the convex portion in the first channel may be smaller than the height of the convex portion in the third channel. The convex portion and the elastic component may be set at the same time to prevent an excessive pushing force in the direction from the distal end to the proximal end generated by the elastic component due to the elastic recovery, in which the pushing force facilitates the assembly box to retract from the groove. By setting the convex portion and the third channel to the first channel of different heights and dimensions, a certain buffer may be generated, so that the assembly box may retract safely from the groove.

28. The assembly box may move axially from the distal end to the proximal end. A part of the assembly box may enter into the groove. The joint portion may be positioned outside the first channel. The sheath may move axially from the distal end to the proximal end through the assembly groove. The first assembly of the sheath and the accommodation pipe may be completed. The assembly box may continue to move from the distal end to the proximal end. The joint portion may enter into the first channel. The sheath may be axially fixed in the assembly groove. The shaft may move from the distal end to the proximal end. The second assembly of the shaft and the clip may be completed. The end effector device and the delivery device may be assembled. A restoring force of the elastic component may push the assembly box to move from the distal end to the proximal end. The assembly box may retract from the groove. Then the joint portion may retract from the first channel, so that the end effector device and the delivery device may retract from the assembly groove from the distal end to the proximal end. The assembly of the end effector device and the delivery device may be divided into the first assembly and the second assembly. The first assembly and the second assembly may be independent from each other. A respective assembly sequence of the first assembly and the second assembly may be adjusted and optimized according to a specific structure of the assembly tool and the assembly box. The adjustment and optimization of different assembly operations may be realized by improving the assembly box and/or assembly tool, which may be more suitable for industrial production and user operation.

29. A single end effector device may be sterilized and sealed in the assembly box. During surgery operation, the assembly box of the single sealed package may be opened one by one according to needs, and the end effector device may be taken out, then the assembly of the delivery device and the end effector device may be completed, which may be convenient to operate and reduce cross-infection.

30. A first end effector device and a second end effector device described herein are only for the purpose of indicating that the end effector device assembled with the delivery device may be multiple. A count of end effector devices may be at least two. The first end effector device may be assembled with the delivery device to form an end effector instrument before delivery packaging, or the first end effector device may be taken out of a packaging box during surgery operation and then assembled with the delivery device to form an end effector instrument. After the first end effector device and the delivery device are released during the surgery operation, the second end effector device may be taken out of the packaging box and assembled with the delivery device to form an end effector instrument. More of the assembly of end effector device and the delivery device may be completed according to the actual needs to avoid waste of medical resources.

31. A package may include a plurality of assembly boxes for accommodating end effector devices and delivery devices. By setting the limiting portion, a relative movement between the delivery devices and the assembly boxes may be limited, avoiding product failure caused by collision and other factors during transportation and accommodation, and ensuring the use safety of the product.

32. The delivery device may include a sheath extending from the distal end to the proximal end. The limiting portion may fix the sheath by wrapping the sheath in or around the limiting portion, which may effectively solve the problem of inconvenient packaging caused by a long length of the sheath.

33. The limiting portion may be arranged at the assembly box, which may simplify the structure, integrate the functions of the assembly box, and reduce the cost.

34. The housing may also include a convex portion and a non-convex portion. The limiting portion may be arranged on the convex portion or the non-convex portion. The limiting portion may be arranged at the convex portion of the housing to save the overall space. Alternatively, the limiting portion may be arranged at the non-convex portion of the housing, so that the overall package and the package of the assembly box may be independent from each other. The position of the limiting portion may be freely selected according to the dimension of the assembly box, which may be flexible and free.

35. The limiting portion may be a limiting groove arranged at the housing, which has a simple structure and is convenient for mass production.

36. The limiting portion may form a limiting channel through a buckle, an elastic material, or a groove, which may be freely selected or combined according to the firmness of the fixation between the end effector device and the housing, a material of the housing material, etc., to complete a limiting function of different needs.

37. The limiting portion may include a first limiting groove and a second limiting groove. The end effector instrument may be accommodated in the first limiting groove. The assembly box may be accommodated in the second limiting groove. Compared to local position limiting, the end effector instrument and the assembly box may be fixed in the first limiting groove and the second limiting groove, respectively, such that the position limiting so achieved may be firmer and the stability of the position limiting may be improved.

38. One or more convex points may be arranged in the limiting groove. The one or more convex points may increase a friction between the limiting groove and the sheath of the end effector instrument, so that a limiting firmness between the end effector instrument and the assembly box (or the housing accommodating the assembly box) may be better.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by this disclosure and are within the spirit and scope of the exemplary embodiments of this disclosure.

Meanwhile, certain terminology has been used to describe embodiments of the present disclosure. For example, the terms "one embodiment," "an embodiment," and/or "some embodiments" mean that a particular feature, structure, or characteristic described in connection with the embodiment is in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in smaller than all features of a single foregoing disclosed embodiment.

In some embodiments, the numbers expressing quantities, properties, and so forth, configured to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present disclosure are not limited to that precisely as shown and described.

What is claimed is:

1. An end effector instrument, comprising:
an end effector device, the end effector device comprising an effector portion configured to perform a specified operation and an accommodation portion configured to partially accommodate the effector portion, the accommodation portion comprising a first connecting portion and an outer pipe, the first connecting portion extending outward from an outer side of a proximal end of the outer pipe along an axial direction of the accommodation portion, and
a delivery device connected to the end effector device, the delivery device being configured to deliver the end effector device to a target region where the specified operation is to be performed, wherein
the delivery device includes an operation portion and a delivery pipe, the operation portion being configured to drive the effector portion to perform the specified operation,
the delivery pipe includes a second connecting portion, the second connecting portion being positioned at a distal end of the delivery pipe, wherein
the operation portion is operable to move relative to the accommodation portion toward a distal end of the accommodation portion, during which the operation portion first causes the first connecting portion to connect to the second connecting portion and subsequently connects to the effector portion,
in response to the operation portion at least partially entering into the accommodation portion, the first connecting portion enters into the second connecting portion, thereby connecting the second connecting portion to the first connecting portion, and connecting the delivery device to the end effector device, and
in response to the operation portion at least partially retracting from the accommodation portion, the first connecting portion retracts from the second connecting portion, thereby disconnecting the second connecting portion from the first connecting portion, and disconnecting the delivery device from the end effector device.

2. The end effector instrument of claim 1, wherein
the accommodation portion includes an inner pipe, at least
a portion of the outer pipe fitting snugly over the inner
pipe,
when the accommodation portion is connected to the
delivery pipe, the outer pipe positions the delivery pipe
relative to the accommodation portion,
when the operation portion at least partially enters into the
inner pipe, the second connecting portion is connected
to the first connecting portion, and the delivery device
is connected to the end effector device, and
when the operation portion at least partially retracts from
the inner pipe, the second connecting portion is dis-
connected from the first connecting portion, and the
delivery device is disconnected from the end effector
device.

3. The end effector instrument of claim 2, wherein
the operation portion includes a shaft,
the first connecting portion includes a limiting convex,
the second connecting portion includes a limiting con-
cave,
in response to the shaft entering into the inner pipe, the
limiting convex is elastically deformed and extended
into the limiting concave to cause the second connect-
ing portion to connect the first connecting portion, and
in response to the shaft retracting from the inner pipe, the
limiting convex is elastically restored and retracted
from the limiting concave to cause the second connect-
ing portion to disconnect the first connecting portion.

4. The end effector instrument of claim 3, wherein the
limiting convex and the accommodation portion are inte-
grally formed.

5. The end effector instrument of claim 2, wherein
the effector portion includes a lock connecting portion,
the accommodation portion includes a locking portion,
the locking portion being configured to connect the
lock connecting portion, and
when the locking portion connects the lock connecting
portion, the effector portion and the accommodation
portion are fixed relative to each other.

6. The end effector instrument of claim 5, wherein
the locking portion is positioned on the outer pipe,
the inner pipe includes a guiding groove located along an
axial direction of the inner pipe, and the guiding groove
is a groove opened along a thickness direction on an
inner wall of the accommodation pipe, and
the lock connecting portion is configured to slide within
the guiding groove.

7. The end effector instrument of claim 6, wherein
the locking portion includes an elastic piece, one end of
the elastic piece being fixedly connected to the outer
pipe, and another end of the elastic piece extending into
an interior of the inner pipe.

8. The end effector instrument of claim 6, wherein
an end of the guiding groove away from the effector
portion has a positioning convex,
a distance between the positioning convex and the effector
portion exceeds a distance between the locking portion
and the effector portion,
a retaining portion is located on the positioning convex,
the retaining portion includes a fixed end and a free end,
the fixed end of the retaining portion is fixedly connected
to the positioning convex, and
the free end of the retaining portion faces an interior of the
guiding groove.

9. The end effector instrument of claim 5, wherein
the effector portion includes a clip, the clip comprising a
first clip arm, a second clip arm, and a connecting pin,
the first clip arm and the second clip arm are connected
through the connecting pin, and
the lock connecting portion is formed by one end or both
ends of the connecting pin.

10. The end effector instrument of claim 9, wherein
an end of the first clip arm close to the connecting pin has
a first bending portion that bends towards the second
clip arm,
the first bending portion has a first hole,
one end of the second clip arm close to the connecting pin
has a second bending portion that bends towards the
first clip arm,
the second bending portion has a second hole, and
the first hole and the second hole at least partially overlap.

11. The end effector instrument of claim 1, further includ-
ing:
an assembly device configured to assemble the end effec-
tor device and the delivery device to establish a con-
nection between the end effector device and the deliv-
ery device, wherein
the assembly device includes an assembly box config-
ured to fix the end effector device and the delivery
device when the end effector device and the delivery
device are assembled, the assembly box including:
an accommodation portion configured to accommo-
date the end effector device,
an assembly groove configured to accommodate the
delivery device to achieve an assembly of the
delivery device and the end effector device, and
a joint portion configured to fix the delivery device
in the assembly groove.

12. The end effector instrument of claim 11, wherein
the joint portion includes a first portion and a second
portion,
the first portion of the joint portion extends beyond an
outer surface of the assembly groove, and
after the first portion of the joint portion is pressed, the
second portion of the joint portion enters into an
interior of the assembly groove.

13. The end effector instrument of claim 12, wherein
the assembly device further includes an assembly tool,
the assembly tool includes at least one groove, and
the assembly box is configured to enter into or retract
from the at least one groove.

14. The end effector instrument of claim 13, wherein
one of the at least one groove of the assembly tool
includes a first channel,
a height of the first channel is smaller than or equal to a
height of the joint portion, and
when the joint portion enters into the first channel, the first
channel presses the first portion of the joint portion.

15. The end effector instrument of claim 14, wherein
the groove further includes a second channel,
the second channel is in communication with the first
channel,
the second channel is located at an entrance end of the first
channel, and
a height of the second channel gradually decreases along
a direction from a proximal end to a distal end.

16. The end effector instrument of claim 14, wherein
the groove further includes a third channel,
the third channel is in communication with the first
channel,
the third channel is located at an exit end of the first
channel, and a height of the third channel exceeds a height of the first
   channel.

17. The end effector instrument of claim 16, wherein
a convex portion is located outside the assembly box, the
   convex portion being elastic,
the convex portion is in a compressed state when the
   convex portion is positioned within the first channel,
   and
the convex portion is in an original state when the convex
   portion is positioned within the third channel.

18. The end effector instrument of claim 16, wherein
the third channel is configured with an elastic component,
   and
the elastic component is configured to apply a bias
   pressure to the assembly box along a first direction so
   as to cause the assembly box to retract from the third
   channel.

19. The end effector instrument of claim 11, wherein
the assembly box includes a housing and a limiting
   portion positioned at the housing, the limiting portion
   being configured to limit a relative movement between
   the delivery device and the assembly box, and
the limiting portion of the assembly box is configured to
   limit a relative movement between the delivery pipe
   and the housing.

* * * * *